(12) United States Patent
Ganesan et al.

(10) Patent No.: US 9,750,606 B2
(45) Date of Patent: Sep. 5, 2017

(54) SYSTEMS AND METHODS FOR HEART VALVE THERAPY

(71) Applicant: Caisson Interventional, LLC, Maple Grove, MN (US)

(72) Inventors: Kavitha Ganesan, Maple Grove, MN (US); Ramji Venkatasubramanian, Maple Grove, MN (US); Andrew T. Forsberg, Plymouth, MN (US); Cyril J. Schweich, Jr., Maple Grove, MN (US); Todd J. Mortier, Mound, MN (US); Erik O. Martz, Bloomington, MN (US); Douglas J. Krone, Rogers, MN (US)

(73) Assignee: Caisson Interventional, LLC, Maple Grove, MN (US)

(*) Notice: Subject to any disclaimer, the term of this patent is extended or adjusted under 35 U.S.C. 154(b) by 168 days.

(21) Appl. No.: 14/673,055

(22) Filed: Mar. 30, 2015

(65) Prior Publication Data

US 2016/0113766 A1    Apr. 28, 2016

Related U.S. Application Data

(63) Continuation of application No. 14/671,577, filed on Mar. 27, 2015.
(Continued)

(51) Int. Cl.
*A61F 2/24* (2006.01)

(52) U.S. Cl.
CPC .......... *A61F 2/2427* (2013.01); *A61F 2/2412* (2013.01); *A61F 2/2418* (2013.01);
(Continued)

(58) Field of Classification Search
CPC .... A61F 2/2403; A61F 2/2409; A61F 2/2412; A61F 2/2418; A61F 2/2427; A61F 2/243;
(Continued)

(56) References Cited

U.S. PATENT DOCUMENTS

| 4,680,031 A | 7/1987 | Alonso |
| 5,423,887 A | 6/1995 | Love et al. |

(Continued)

FOREIGN PATENT DOCUMENTS

| EP | 350302 | 1/1990 |
| EP | 0592410 | 4/1994 |

(Continued)

OTHER PUBLICATIONS

European Search Report in European Application No. 15170546.4, dated Apr. 12, 2016, 7 pages.
(Continued)

*Primary Examiner* — Ryan J Severson
(74) *Attorney, Agent, or Firm* — Fish & Richardson P.C.

(57) ABSTRACT

Prosthetic mitral valves described herein can be deployed using a transcatheter mitral valve delivery system and technique to interface and anchor in cooperation with the anatomical structures of a native mitral valve. This document describes prosthetic heart valve designs that interface with native mitral valve structures to create a fluid seal, thereby minimizing mitral regurgitation and paravalvular leaks. This document also describes prosthetic heart valve designs and techniques to manage blood flow through the left ventricular outflow tract. In addition, this document describes prosthetic heart valve designs and techniques that reduce the risk of interference between the prosthetic valves and chordae tendineae.

15 Claims, 29 Drawing Sheets

Related U.S. Application Data

(60) Provisional application No. 62/067,907, filed on Oct. 23, 2014.

(52) U.S. Cl.
CPC .......... *A61F 2/2436* (2013.01); *A61F 2/2439* (2013.01); *A61F 2250/006* (2013.01)

(58) Field of Classification Search
CPC .... A61F 2/2433; A61F 2/2436; A61F 2/2439; A61F 2/2448
See application file for complete search history.

(56) References Cited

U.S. PATENT DOCUMENTS

| | | | |
|---|---|---|---|
| 5,662,704 | A | 9/1997 | Gross |
| 5,855,601 | A | 1/1999 | Bessler et al. |
| 5,984,959 | A | 11/1999 | Robertson et al. |
| 6,113,631 | A | 9/2000 | Jansen |
| 6,296,662 | B1 | 10/2001 | Caffey |
| 6,309,417 | B1 | 10/2001 | Spence et al. |
| 6,332,893 | B1 | 12/2001 | Mortier et al. |
| 6,358,277 | B1 | 3/2002 | Duran |
| 6,425,916 | B1 | 7/2002 | Garrison et al. |
| 6,530,952 | B2 | 3/2003 | Vesely |
| 6,569,196 | B1 | 5/2003 | Vesely |
| 6,582,462 | B1 | 6/2003 | Andersen et al. |
| 6,629,534 | B1 | 10/2003 | St. Goar et al. |
| 6,730,118 | B2 | 5/2004 | Spenser et al. |
| 6,730,121 | B2 | 5/2004 | Ortiz et al. |
| 6,767,362 | B2 | 7/2004 | Schreck |
| 6,769,434 | B2 | 8/2004 | Liddicoat et al. |
| 6,790,229 | B1 | 9/2004 | Berreklouw |
| 6,883,522 | B2 | 4/2005 | Spence et al. |
| 6,893,459 | B1 | 5/2005 | Macoviak |
| 6,893,460 | B2 | 5/2005 | Spenser et al. |
| 6,908,481 | B2 | 6/2005 | Cribier |
| 6,949,122 | B2 | 9/2005 | Adams et al. |
| 7,011,681 | B2 | 3/2006 | Vesely |
| 7,018,406 | B2 | 3/2006 | Seguin et al. |
| 7,044,966 | B2 | 5/2006 | Svanidze et al. |
| 7,101,396 | B2 | 9/2006 | Artof et al. |
| 7,147,663 | B1 | 12/2006 | Berg et al. |
| 7,160,322 | B2 | 1/2007 | Gabbay |
| 7,175,656 | B2 * | 2/2007 | Khairkhahan ........ A61F 2/2403 606/200 |
| 7,217,287 | B2 | 5/2007 | Wilson et al. |
| 7,252,682 | B2 | 8/2007 | Seguin |
| 7,320,704 | B2 | 1/2008 | Lashinski et al. |
| 7,329,278 | B2 | 2/2008 | Seguin et al. |
| 7,381,218 | B2 | 6/2008 | Schreck |
| 7,381,220 | B2 | 6/2008 | Macoviak et al. |
| 7,393,360 | B2 | 7/2008 | Spenser et al. |
| 7,442,204 | B2 | 10/2008 | Schwammenthal et al. |
| 7,503,930 | B2 | 3/2009 | Sharkawy et al. |
| 7,510,575 | B2 | 3/2009 | Spenser et al. |
| 7,524,330 | B2 | 4/2009 | Berreklouw |
| 7,524,331 | B2 | 4/2009 | Birdsall |
| 7,578,843 | B2 | 8/2009 | Shu |
| 7,585,321 | B2 | 9/2009 | Cribier |
| 7,597,711 | B2 | 10/2009 | Drews et al. |
| 7,618,446 | B2 | 11/2009 | Andersen et al. |
| 7,625,403 | B2 | 12/2009 | Krivoruchko |
| 7,632,308 | B2 | 12/2009 | Loulmet |
| 7,708,775 | B2 | 5/2010 | Rowe et al. |
| 7,717,955 | B2 | 5/2010 | Lane et al. |
| 7,722,666 | B2 * | 5/2010 | Lafontaine ............ A61F 2/2418 623/2.11 |
| 7,727,276 | B2 | 6/2010 | Machiraju |
| 7,748,389 | B2 | 7/2010 | Salahieh et al. |
| 7,776,083 | B2 | 8/2010 | Vesely |
| 7,780,725 | B2 | 8/2010 | Haug et al. |
| 7,785,364 | B2 | 8/2010 | Styrc |
| 7,837,727 | B2 * | 11/2010 | Goetz ................... A61F 2/2418 623/1.15 |
| 7,896,915 | B2 | 3/2011 | Guyenot et al. |
| 7,914,569 | B2 | 3/2011 | Nguyen et al. |
| 7,935,144 | B2 | 5/2011 | Robin et al. |
| 7,947,072 | B2 | 5/2011 | Yang et al. |
| 7,947,075 | B2 | 5/2011 | Goetz et al. |
| 7,959,672 | B2 | 6/2011 | Salahieh et al. |
| 7,981,153 | B2 | 7/2011 | Fogarty et al. |
| 7,988,725 | B2 | 8/2011 | Gross et al. |
| 8,016,882 | B2 | 9/2011 | Macoviak et al. |
| 8,025,695 | B2 | 9/2011 | Fogarty et al. |
| 8,048,153 | B2 | 11/2011 | Salahieh et al. |
| 8,052,749 | B2 | 11/2011 | Salahieh et al. |
| 8,055,360 | B2 | 11/2011 | Park et al. |
| 8,057,540 | B2 | 11/2011 | Letac et al. |
| 8,062,355 | B2 | 11/2011 | Figulla et al. |
| 8,092,518 | B2 | 1/2012 | Schreck |
| 8,092,521 | B2 | 1/2012 | Figulla et al. |
| 8,092,524 | B2 | 1/2012 | Nugent et al. |
| 8,123,801 | B2 | 2/2012 | Milo |
| 8,133,270 | B2 | 3/2012 | Kheradvar et al. |
| 8,142,492 | B2 | 3/2012 | Forster et al. |
| 8,157,852 | B2 | 4/2012 | Bloom et al. |
| 8,157,853 | B2 | 4/2012 | Laske et al. |
| 8,163,011 | B2 | 4/2012 | Rankin |
| 8,172,898 | B2 | 5/2012 | Alferness et al. |
| 8,182,528 | B2 | 5/2012 | Salahieh et al. |
| 8,182,530 | B2 | 5/2012 | Huber |
| 8,206,437 | B2 | 6/2012 | Bonhoeffer et al. |
| 8,231,670 | B2 | 7/2012 | Salahieh et al. |
| 8,236,049 | B2 | 8/2012 | Rowe et al. |
| 8,246,677 | B2 | 8/2012 | Ryan |
| 8,252,051 | B2 | 8/2012 | Chau et al. |
| 8,262,724 | B2 | 9/2012 | Seguin et al. |
| 8,273,120 | B2 | 9/2012 | Dolan |
| 8,277,502 | B2 | 10/2012 | Miller et al. |
| 8,282,051 | B2 | 10/2012 | Nutaro et al. |
| 8,287,591 | B2 | 10/2012 | Keidar et al. |
| 8,292,938 | B2 | 10/2012 | Case |
| 8,308,796 | B2 | 11/2012 | Lashinski et al. |
| 8,308,798 | B2 | 11/2012 | Pintor et al. |
| 8,317,858 | B2 | 11/2012 | Straubinger et al. |
| 8,323,332 | B2 | 12/2012 | Agnew |
| 8,323,335 | B2 | 12/2012 | Rowe et al. |
| 8,348,998 | B2 | 1/2013 | Pintor et al. |
| 8,403,983 | B2 | 3/2013 | Quadri et al. |
| 8,449,599 | B2 | 5/2013 | Chau et al. |
| 8,454,686 | B2 | 6/2013 | Alkhatib |
| 8,460,366 | B2 | 6/2013 | Rowe |
| 8,500,798 | B2 | 8/2013 | Rowe et al. |
| 8,512,398 | B2 | 8/2013 | Alkhatib |
| 8,512,399 | B2 * | 8/2013 | Lafontaine ............ A61F 2/2418 623/2.11 |
| 8,568,477 | B2 | 10/2013 | Lashinski et al. |
| 8,579,964 | B2 | 11/2013 | Lane et al. |
| 8,585,755 | B2 | 11/2013 | Chau et al. |
| 8,623,080 | B2 | 1/2014 | Fogarty et al. |
| 8,628,569 | B2 | 1/2014 | Benichou et al. |
| 8,628,571 | B1 | 1/2014 | Hacohen et al. |
| 8,632,586 | B2 | 1/2014 | Spenser et al. |
| 8,641,757 | B2 | 2/2014 | Pintor et al. |
| 8,652,203 | B2 | 2/2014 | Quadri et al. |
| 8,657,872 | B2 | 2/2014 | Seguin |
| 8,685,085 | B2 | 4/2014 | Guyenot et al. |
| 8,685,086 | B2 | 4/2014 | Navia et al. |
| 8,696,742 | B2 | 4/2014 | Pintor et al. |
| 8,728,155 | B2 | 5/2014 | Montorfano et al. |
| 8,795,355 | B2 | 8/2014 | Alkhatib |
| 8,795,356 | B2 | 8/2014 | Quadri et al. |
| 8,808,371 | B2 | 8/2014 | Cartledge |
| 8,834,564 | B2 | 9/2014 | Tuval et al. |
| 8,840,662 | B2 | 9/2014 | Salahieh et al. |
| 8,840,663 | B2 | 9/2014 | Salahieh et al. |
| 8,845,720 | B2 * | 9/2014 | Conklin ................ A61F 2/2412 623/2.14 |
| 8,852,272 | B2 | 10/2014 | Gross et al. |
| 8,858,620 | B2 | 10/2014 | Salahieh et al. |
| 8,870,948 | B1 | 10/2014 | Erzberger et al. |
| 8,870,949 | B2 | 10/2014 | Rowe |
| 8,876,895 | B2 | 11/2014 | Tuval et al. |

(56) References Cited

U.S. PATENT DOCUMENTS

| | | |
|---|---|---|
| 8,894,702 B2 | 11/2014 | Quadri et al. |
| 8,911,493 B2 | 12/2014 | Rowe et al. |
| 8,926,690 B2 | 1/2015 | Kovalsky |
| 8,926,691 B2 | 1/2015 | Chau et al. |
| 8,932,358 B1 | 1/2015 | Nehls |
| 8,961,595 B2 | 2/2015 | Alkhatib |
| 8,968,395 B2 | 3/2015 | Hauser et al. |
| 8,986,370 B2 | 3/2015 | Annest |
| 8,986,373 B2 | 3/2015 | Chau et al. |
| 9,005,277 B2 | 4/2015 | Pintor et al. |
| 9,005,278 B2 | 4/2015 | Pintor et al. |
| 9,017,399 B2 | 4/2015 | Gross et al. |
| 9,023,100 B2 | 5/2015 | Quadri et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,050,188 B2 | 6/2015 | Schweich et al. |
| 9,066,801 B2 | 6/2015 | Kovalsky et al. |
| 9,072,604 B1 | 7/2015 | Melnick et al. |
| 9,084,676 B2 | 7/2015 | Chau et al. |
| 9,132,006 B2 | 9/2015 | Spenser et al. |
| 9,155,617 B2 | 10/2015 | Carpentier et al. |
| 9,168,130 B2 * | 10/2015 | Straubinger ............ A61F 2/2418 |
| 9,168,133 B2 | 10/2015 | Spenser et al. |
| 9,173,738 B2 | 11/2015 | Murray, III et al. |
| 9,192,466 B2 | 11/2015 | Kovalsky et al. |
| 9,226,826 B2 | 1/2016 | Rust |
| 9,241,792 B2 | 1/2016 | Benichou et al. |
| 9,248,016 B2 * | 2/2016 | Oba ....................... A61F 2/2418 |
| 9,259,315 B2 | 2/2016 | Zhou et al. |
| 9,265,631 B2 * | 2/2016 | Straubinger ............ A61F 2/2418 |
| 9,289,293 B2 | 3/2016 | Murad et al. |
| 9,295,547 B2 | 3/2016 | Costello et al. |
| 9,295,548 B2 | 3/2016 | Drews et al. |
| 9,295,550 B2 | 3/2016 | Nguyen et al. |
| 9,301,843 B2 | 4/2016 | Richardson et al. |
| 9,301,863 B2 | 4/2016 | Punga et al. |
| 9,331,328 B2 | 5/2016 | Eberhardt et al. |
| 9,339,377 B2 | 5/2016 | Quadri et al. |
| 9,339,378 B2 | 5/2016 | Quadri et al. |
| 9,339,379 B2 | 5/2016 | Quadri et al. |
| 9,339,380 B2 | 5/2016 | Quadri et al. |
| 9,339,382 B2 | 5/2016 | Tabor et al. |
| 9,345,573 B2 | 5/2016 | Nyuli et al. |
| 9,358,111 B2 | 6/2016 | Spence et al. |
| 9,370,423 B2 | 6/2016 | Ryan |
| 9,370,424 B2 | 6/2016 | Call et al. |
| 9,375,311 B2 | 6/2016 | Gloss et al. |
| 9,387,071 B2 | 7/2016 | Tuval et al. |
| 9,402,719 B2 | 8/2016 | Lane et al. |
| 9,402,721 B2 | 8/2016 | Buchbinder et al. |
| 9,414,913 B2 | 8/2016 | Beith et al. |
| 9,414,918 B2 | 8/2016 | Chau et al. |
| 9,433,503 B2 | 9/2016 | Tsukashina et al. |
| 9,439,757 B2 | 9/2016 | Wallace et al. |
| 9,456,896 B2 | 10/2016 | Quadri et al. |
| 9,468,525 B2 | 10/2016 | Kovalsky |
| 9,480,556 B2 | 11/2016 | Revuelta et al. |
| 9,480,559 B2 | 11/2016 | Vidlund et al. |
| 9,486,306 B2 | 11/2016 | Tegels et al. |
| 9,492,273 B2 | 11/2016 | Wallace et al. |
| 9,510,946 B2 | 12/2016 | Chau et al. |
| 9,522,062 B2 | 12/2016 | Tuval |
| 9,532,870 B2 | 1/2017 | Cooper et al. |
| 9,554,903 B2 | 1/2017 | Rowe et al. |
| 9,561,100 B2 | 2/2017 | Pintor et al. |
| 9,561,103 B2 | 2/2017 | Granada et al. |
| 9,572,662 B2 | 2/2017 | Morriss et al. |
| 9,579,194 B2 | 2/2017 | Elizondo et al. |
| 9,579,196 B2 | 2/2017 | Morriss et al. |
| 2001/0007956 A1 | 7/2001 | Letac et al. |
| 2001/0021872 A1 | 9/2001 | Bailey et al. |
| 2002/0151970 A1 | 10/2002 | Garrison et al. |
| 2003/0130726 A1 | 7/2003 | Thorpe et al. |
| 2004/0210307 A1 * | 10/2004 | Khairkhahan ........ A61F 2/2403 623/2.18 |
| 2005/0137689 A1 | 6/2005 | Salaheih et al. |
| 2005/0137690 A1 | 6/2005 | Salahieh et al. |
| 2005/0165479 A1 | 7/2005 | Drews et al. |
| 2006/0235509 A1 * | 10/2006 | Lafontaine ............ A61F 2/2418 623/2.11 |
| 2007/0027533 A1 | 2/2007 | Douk |
| 2007/0168024 A1 * | 7/2007 | Khairkhahan ........ A61F 2/2403 623/2.18 |
| 2008/0004697 A1 | 1/2008 | Lichtenstein et al. |
| 2008/0015671 A1 | 1/2008 | Bonhoeffer |
| 2008/0086164 A1 | 4/2008 | Rowe |
| 2008/0103586 A1 | 5/2008 | Styrc et al. |
| 2008/0140189 A1 | 6/2008 | Nguyen et al. |
| 2008/0183273 A1 * | 7/2008 | Mesana ................ A61F 2/2418 623/1.11 |
| 2008/0221672 A1 | 9/2008 | Lamphere et al. |
| 2009/0005863 A1 | 1/2009 | Goetz et al. |
| 2009/0216310 A1 * | 8/2009 | Straubinger .......... A61F 2/2418 623/1.15 |
| 2009/0216312 A1 * | 8/2009 | Straubinger .......... A61F 2/2418 623/1.16 |
| 2010/0049315 A1 | 2/2010 | Kirson |
| 2010/0100173 A1 | 4/2010 | Lafontaine |
| 2010/0161036 A1 * | 6/2010 | Pintor .................... A61F 2/2418 623/1.26 |
| 2010/0217382 A1 | 8/2010 | Chau et al. |
| 2010/0249894 A1 * | 9/2010 | Oba ....................... A61F 2/2418 623/1.11 |
| 2010/0249908 A1 * | 9/2010 | Chau .................... A61F 2/2418 623/1.26 |
| 2010/0262232 A1 | 10/2010 | Annest |
| 2010/0280606 A1 | 11/2010 | Naor |
| 2010/0298931 A1 | 11/2010 | Quadri et al. |
| 2010/0312333 A1 | 12/2010 | Navia et al. |
| 2010/0331972 A1 * | 12/2010 | Pintor ................... A61F 2/2409 623/2.11 |
| 2011/0004296 A1 | 1/2011 | Lutter et al. |
| 2011/0022168 A1 | 1/2011 | Cartledge |
| 2011/0040374 A1 * | 2/2011 | Goetz .................. A61F 2/2418 623/2.11 |
| 2011/0137397 A1 | 6/2011 | Chau et al. |
| 2011/0137410 A1 | 6/2011 | Hacohen |
| 2011/0166636 A1 | 7/2011 | Rowe |
| 2011/0208293 A1 | 8/2011 | Tabor |
| 2011/0218619 A1 | 9/2011 | Benichou et al. |
| 2011/0224785 A1 | 9/2011 | Hacohen |
| 2011/0245911 A1 | 10/2011 | Quill et al. |
| 2011/0257721 A1 | 10/2011 | Tabor |
| 2011/0282438 A1 | 11/2011 | Drews et al. |
| 2011/0295363 A1 | 12/2011 | Girard et al. |
| 2011/0301702 A1 | 12/2011 | Rust et al. |
| 2011/0319988 A1 | 12/2011 | Schankereli et al. |
| 2011/0319989 A1 | 12/2011 | Lane et al. |
| 2012/0010697 A1 | 1/2012 | Shin et al. |
| 2012/0016464 A1 | 1/2012 | Seguin |
| 2012/0035722 A1 | 2/2012 | Tuval |
| 2012/0053675 A1 | 3/2012 | Borock |
| 2012/0059458 A1 | 3/2012 | Buchbinder et al. |
| 2012/0078357 A1 * | 3/2012 | Conklin ................ A61F 2/2412 623/2.18 |
| 2012/0101571 A1 | 4/2012 | Thambar et al. |
| 2012/0136430 A1 | 5/2012 | Sochman et al. |
| 2012/0310328 A1 | 12/2012 | Olson et al. |
| 2013/0053949 A1 * | 2/2013 | Pintor ................... A61F 2/2418 623/2.18 |
| 2013/0079869 A1 * | 3/2013 | Straubinger .......... A61F 2/2418 623/1.26 |
| 2013/0090725 A1 * | 4/2013 | Pintor ................... A61F 2/2409 623/2.11 |
| 2013/0116777 A1 * | 5/2013 | Pintor ................... A61F 2/2409 623/2.11 |
| 2013/0172992 A1 | 7/2013 | Gross et al. |
| 2013/0184811 A1 | 7/2013 | Rowe et al. |
| 2013/0211508 A1 | 8/2013 | Lane et al. |
| 2013/0282110 A1 | 10/2013 | Schweich et al. |
| 2013/0282114 A1 | 10/2013 | Schweich et al. |

(56) References Cited

U.S. PATENT DOCUMENTS

| | | |
|---|---|---|
| 2013/0304200 A1 | 11/2013 | McLean et al. |
| 2013/0345799 A1* | 12/2013 | Lafontaine ............ A61F 2/2418 623/2.11 |
| 2014/0005778 A1 | 1/2014 | Buchbinder et al. |
| 2014/0012372 A1 | 1/2014 | Chau et al. |
| 2014/0012373 A1 | 1/2014 | Chau et al. |
| 2014/0039611 A1 | 2/2014 | Lane et al. |
| 2014/0052237 A1 | 2/2014 | Lane et al. |
| 2014/0200662 A1 | 7/2014 | Eftel et al. |
| 2014/0214156 A1 | 7/2014 | Navia et al. |
| 2014/0222136 A1 | 8/2014 | Geist et al. |
| 2014/0228946 A1 | 8/2014 | Chau et al. |
| 2014/0236291 A1 | 8/2014 | Schweich et al. |
| 2014/0257467 A1 | 9/2014 | Lane et al. |
| 2014/0316516 A1 | 10/2014 | Vidlund |
| 2014/0343669 A1 | 11/2014 | Lane et al. |
| 2014/0358223 A1 | 12/2014 | Rafiee et al. |
| 2014/0364943 A1* | 12/2014 | Conklin ................ A61F 2/2412 623/2.11 |
| 2015/0039083 A1 | 2/2015 | Rafiee |
| 2015/0094802 A1 | 4/2015 | Buchbinder et al. |
| 2015/0112433 A1 | 4/2015 | Schweich et al. |
| 2015/0127096 A1 | 5/2015 | Rowe et al. |
| 2015/0142103 A1 | 5/2015 | Vidlund |
| 2015/0150678 A1 | 6/2015 | Brecker |
| 2015/0157458 A1 | 6/2015 | Thambar et al. |
| 2015/0173897 A1 | 6/2015 | Raanani et al. |
| 2015/0196390 A1 | 7/2015 | Ma et al. |
| 2015/0216656 A1* | 8/2015 | Pintor .................... A61F 2/2418 623/2.11 |
| 2015/0216657 A1 | 8/2015 | Braido |
| 2015/0216660 A1* | 8/2015 | Pintor ................... A61F 2/2409 623/2.11 |
| 2015/0238312 A1 | 8/2015 | Lashinski |
| 2015/0238313 A1 | 8/2015 | Spence et al. |
| 2015/0265402 A1 | 9/2015 | Centola et al. |
| 2015/0320553 A1 | 11/2015 | Chau et al. |
| 2015/0327995 A1 | 11/2015 | Morin et al. |
| 2015/0327996 A1 | 11/2015 | Fahim et al. |
| 2015/0327999 A1 | 11/2015 | Board et al. |
| 2015/0335421 A1 | 11/2015 | Figulla et al. |
| 2015/0342733 A1 | 12/2015 | Alkhatib et al. |
| 2015/0351906 A1 | 12/2015 | Hammer et al. |
| 2015/0359629 A1 | 12/2015 | Ganesan et al. |
| 2016/0000564 A1 | 1/2016 | Buchbinder et al. |
| 2016/0008131 A1 | 1/2016 | Christianson et al. |
| 2016/0022417 A1 | 1/2016 | Karapetian et al. |
| 2016/0045307 A1 | 2/2016 | Yohanan et al. |
| 2016/0045309 A1 | 2/2016 | Valdez et al. |
| 2016/0051362 A1 | 2/2016 | Cooper et al. |
| 2016/0074160 A1 | 3/2016 | Christianson et al. |
| 2016/0106539 A1 | 4/2016 | Buchbinder et al. |
| 2016/0120646 A1 | 5/2016 | Dwork et al. |
| 2016/0158000 A1 | 6/2016 | Granada et al. |
| 2016/0158001 A1 | 6/2016 | Wallace et al. |
| 2016/0158003 A1 | 6/2016 | Wallace et al. |
| 2016/0184095 A1 | 6/2016 | Spence et al. |
| 2016/0193044 A1 | 7/2016 | Achiluzzi |
| 2016/0199180 A1 | 7/2016 | Zeng et al. |
| 2016/0220364 A1* | 8/2016 | Straubinger .......... A61F 2/2418 |
| 2016/0228251 A1 | 8/2016 | Nyuli et al. |
| 2016/0235529 A1 | 8/2016 | Ma et al. |
| 2016/0242906 A1 | 8/2016 | Morriss et al. |
| 2016/0270917 A1 | 9/2016 | Tuval et al. |
| 2016/0310268 A1 | 10/2016 | Oba et al. |
| 2016/0317290 A1 | 11/2016 | Chau et al. |
| 2016/0317304 A1 | 11/2016 | Spence et al. |
| 2016/0324631 A1 | 11/2016 | Lane et al. |
| 2016/0324633 A1 | 11/2016 | Gross et al. |
| 2016/0331523 A1 | 11/2016 | Chau et al. |
| 2016/0331531 A1 | 11/2016 | Quadri et al. |
| 2016/0331534 A1 | 11/2016 | Buchbinder et al. |
| 2016/0338826 A1 | 11/2016 | Chau et al. |
| 2016/0338829 A1 | 11/2016 | Call et al. |
| 2016/0346080 A1 | 12/2016 | Righini et al. |
| 2016/0354203 A1 | 12/2016 | Tuval et al. |
| 2016/0354204 A1 | 12/2016 | Braido et al. |
| 2016/0361162 A1 | 12/2016 | Richter et al. |
| 2016/0361163 A1 | 12/2016 | Yohanan et al. |
| 2016/0374801 A1 | 12/2016 | Jiminez et al. |
| 2017/0007398 A1 | 1/2017 | Drews et al. |
| 2017/0049564 A1 | 2/2017 | Board et al. |
| 2017/0056162 A1 | 3/2017 | Harewood |
| 2017/0056163 A1 | 3/2017 | Tayeb et al. |
| 2017/0056166 A1 | 3/2017 | Ratz et al. |
| 2017/0056176 A1 | 3/2017 | Rowe et al. |

FOREIGN PATENT DOCUMENTS

| | | |
|---|---|---|
| EP | 592410 | 4/1994 |
| EP | 705081 | 10/2001 |
| EP | 1338255 | 8/2003 |
| EP | 825841 | 10/2003 |
| EP | 833595 | 10/2003 |
| EP | 910313 | 11/2003 |
| EP | 910314 | 11/2003 |
| EP | 0910314 | 11/2003 |
| EP | 1006949 | 10/2004 |
| EP | 1233731 | 12/2004 |
| EP | 1251803 | 6/2005 |
| EP | 2674130 | 6/2005 |
| EP | 1267753 | 10/2005 |
| EP | 830112 | 11/2005 |
| EP | 1171059 | 11/2005 |
| EP | 1328215 | 11/2005 |
| EP | 1318775 | 11/2006 |
| EP | 1474077 | 2/2007 |
| EP | 1143882 | 12/2007 |
| EP | 1180987 | 8/2008 |
| EP | 1237509 | 12/2008 |
| EP | 1562522 | 12/2008 |
| EP | 2000115 | 12/2008 |
| EP | 1330213 | 3/2009 |
| EP | 1610727 | 4/2009 |
| EP | 1343438 | 7/2009 |
| EP | 2078498 | 7/2009 |
| EP | 1684667 | 8/2009 |
| EP | 1408850 | 9/2009 |
| EP | 1653888 | 9/2009 |
| EP | 1049425 | 11/2009 |
| EP | 1703865 | 2/2010 |
| EP | 1682048 | 3/2010 |
| EP | 1509171 | 6/2010 |
| EP | 1968491 | 7/2010 |
| EP | 1176913 | 10/2010 |
| EP | 1465554 | 12/2010 |
| EP | 1940321 | 12/2010 |
| EP | 2258312 | 12/2010 |
| EP | 1441672 | 9/2011 |
| EP | 2160150 | 10/2011 |
| EP | 1603493 | 12/2011 |
| EP | 2399549 | 12/2011 |
| EP | 2399550 | 12/2011 |
| EP | 1788984 | 2/2012 |
| EP | 2055266 | 2/2012 |
| EP | 2420205 | 2/2012 |
| EP | 1621162 | 5/2012 |
| EP | 2138132 | 6/2012 |
| EP | 2476394 | 7/2012 |
| EP | 2124824 | 10/2012 |
| EP | 2088965 | 11/2012 |
| EP | 2526895 | 11/2012 |
| EP | 2526898 | 11/2012 |
| EP | 2526899 | 11/2012 |
| EP | 2529696 | 12/2012 |
| EP | 2529697 | 12/2012 |
| EP | 2529698 | 12/2012 |
| EP | 2529699 | 12/2012 |
| EP | 2537487 | 12/2012 |
| EP | 1919397 | 1/2013 |
| EP | 2015709 | 1/2013 |
| EP | 1750622 | 2/2013 |
| EP | 2257242 | 2/2013 |
| EP | 2260796 | 2/2013 |

(56) References Cited

FOREIGN PATENT DOCUMENTS

| | | |
|---|---|---|
| EP | 1701668 | 3/2013 |
| EP | 2260797 | 3/2013 |
| EP | 2340075 | 3/2013 |
| EP | 2260798 | 6/2013 |
| EP | 2626040 | 8/2013 |
| EP | 1758523 | 9/2013 |
| EP | 2073756 | 10/2013 |
| EP | 2109417 | 11/2013 |
| EP | 2477555 | 12/2013 |
| EP | 1838241 | 2/2014 |
| EP | 1926455 | 4/2014 |
| EP | 2405966 | 4/2014 |
| EP | 2257243 | 5/2014 |
| EP | 2316381 | 5/2014 |
| EP | 2745805 | 6/2014 |
| EP | 2117469 | 7/2014 |
| EP | 2124826 | 7/2014 |
| EP | 2258316 | 7/2014 |
| EP | 2749254 | 7/2014 |
| EP | 1667604 | 8/2014 |
| EP | 2211779 | 8/2014 |
| EP | 2772228 | 9/2014 |
| EP | 2142143 | 11/2014 |
| EP | 2815723 | 12/2014 |
| EP | 2815724 | 12/2014 |
| EP | 2815725 | 12/2014 |
| EP | 2254515 | 1/2015 |
| EP | 1465555 | 5/2015 |
| EP | 2068767 | 7/2015 |
| EP | 1702247 | 8/2015 |
| EP | 1729688 | 8/2015 |
| EP | 2262447 | 8/2015 |
| EP | 2901966 | 8/2015 |
| EP | 1804686 | 9/2015 |
| EP | 2675396 | 9/2015 |
| EP | 1734903 | 10/2015 |
| EP | 2254513 | 10/2015 |
| EP | 2544626 | 10/2015 |
| EP | 2926766 | 10/2015 |
| EP | 2926767 | 10/2015 |
| EP | 1748745 | 12/2015 |
| EP | 1755459 | 12/2015 |
| EP | 1850796 | 12/2015 |
| EP | 1991168 | 1/2016 |
| EP | 2254512 | 1/2016 |
| EP | 2263609 | 1/2016 |
| EP | 2012712 | 2/2016 |
| EP | 1585463 | 3/2016 |
| EP | 2170416 | 3/2016 |
| EP | 2278944 | 3/2016 |
| EP | 1871300 | 4/2016 |
| EP | 2572676 | 4/2016 |
| EP | 2626041 | 4/2016 |
| EP | 2237746 | 5/2016 |
| EP | 2582326 | 5/2016 |
| EP | 2618784 | 5/2016 |
| EP | 1734902 | 6/2016 |
| EP | 1906884 | 6/2016 |
| EP | 2190379 | 6/2016 |
| EP | 2416739 | 6/2016 |
| EP | 2572675 | 6/2016 |
| WO | WO 2005/062980 | 7/2005 |
| WO | WO 2009/155561 | 12/2009 |
| WO | WO 2011/109813 | 9/2011 |
| WO | WO 2011/119101 | 9/2011 |
| WO | WO 2012/103204 | 8/2012 |

OTHER PUBLICATIONS

U.S. Appl. No. 61/266,774, filed Dec. 16, 2009, Chau et al.
U.S. Appl. No. 61/287,099, filed Dec. 4, 2009, Chau et al.
Supplementary European Search Report in Eurpoean Application No. 13778768, dated Jan. 12, 2016, 7 pages.
International Search Report and Written Opinion in International Application No. PCT/US2015/056935, dated Feb. 12, 2016, 14 pages.
US 9,532,869, 01/2017, Quadri et al. (withdrawn).
International Preliminary Report on Patentability in International Application No. PCT/US2015/035303, dated Dec. 15, 2016, 10 pages.

* cited by examiner

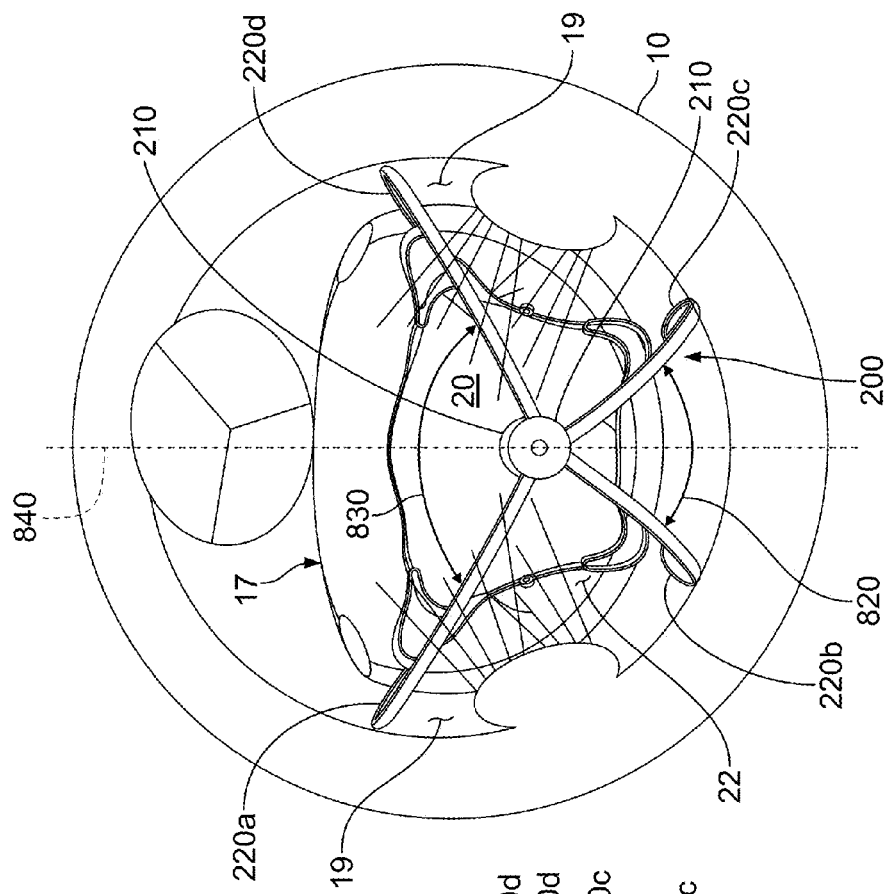
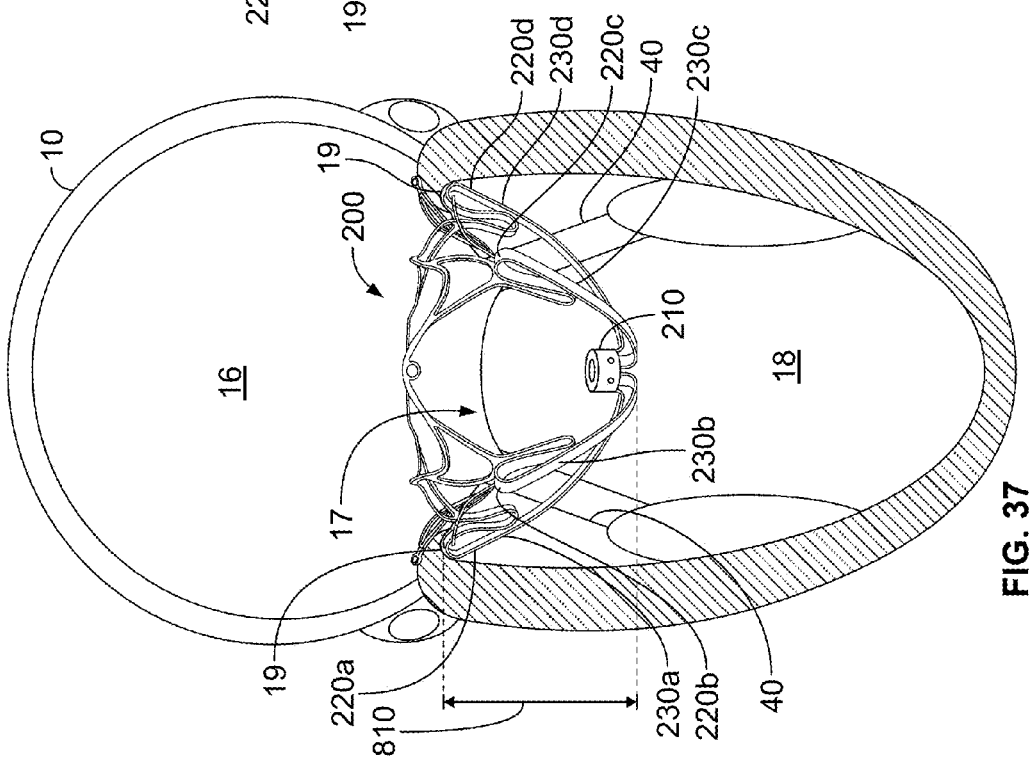

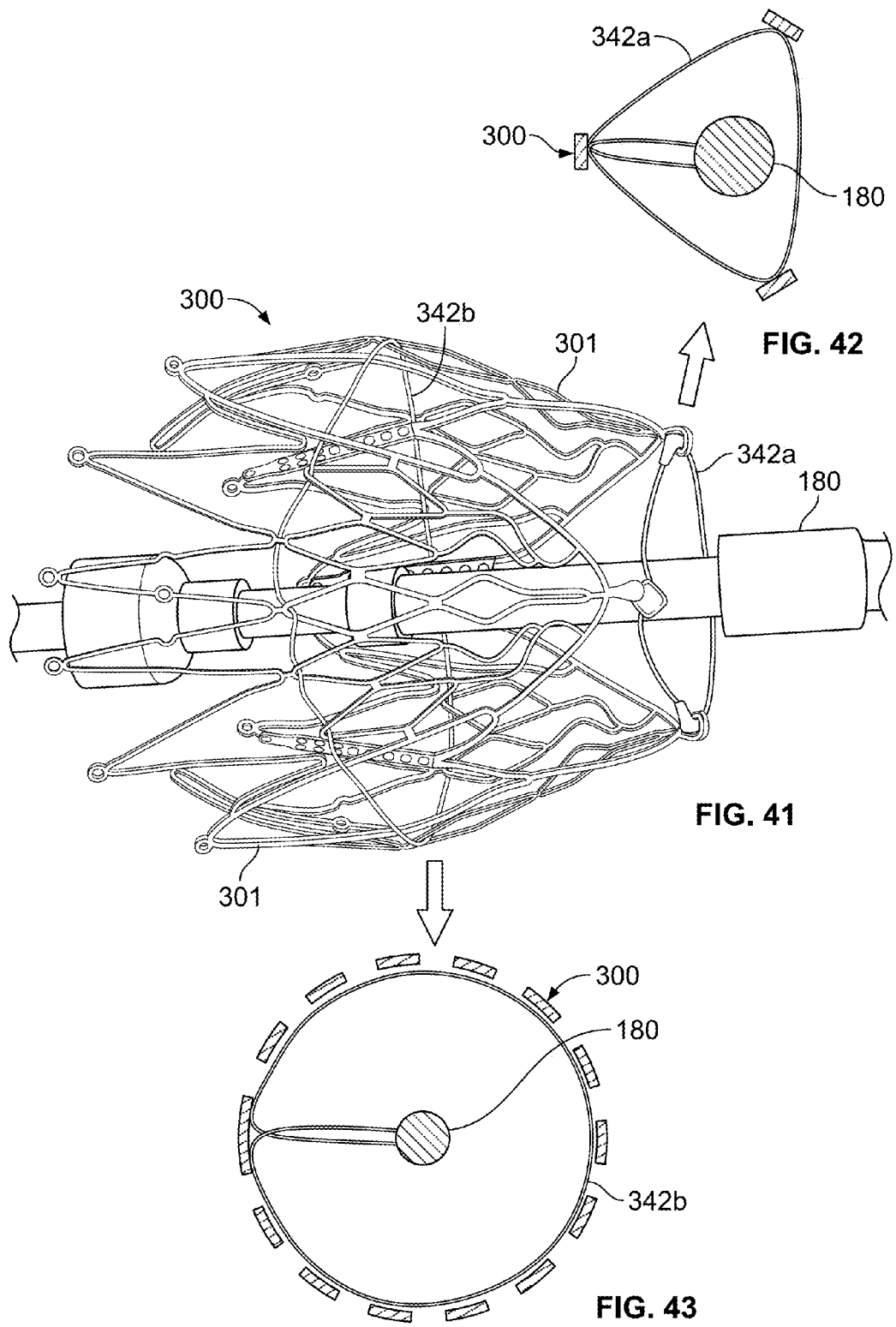

SYSTEMS AND METHODS FOR HEART VALVE THERAPY

CROSS REFERENCE TO RELATED APPLICATIONS

This application is a continuation of U.S. patent application Ser. No. 14/671,577 filed Mar. 27, 2015, which claims the benefit of U.S. Application Ser. No. 62/067,907, filed Oct. 23, 2014. The disclosure of the prior application is considered part of and is incorporated by reference in the disclosure of this application.

TECHNICAL FIELD

This document relates to prosthetic heart valves, such as prosthetic mitral valves that can be implanted using transcatheter techniques.

BACKGROUND

The long-term clinical effect of valve regurgitation is recognized as a significant contributor to cardiovascular related morbidity and mortality. Thus, for many therapies intended to treat the mitral valve, one primary goal is to significantly reduce or eliminate regurgitation. By eliminating the regurgitation at the mitral valve, the destructive volume overload effects on the left ventricle can be attenuated. The volume overload of mitral regurgitation (MR) relates to the excessive kinetic energy required during isotonic contraction to generate overall stroke volume in an attempt to maintain forward stroke volume and cardiac output. It also relates to the pressure potential energy dissipation of the leaking valve during the most energy-consuming portion of the cardiac cycle, isovolumetric contraction. Additionally, therapies for MR reduction can have the effect of reducing the elevated pressures in the left atrium and pulmonary vasculature reducing pulmonary edema (congestion) and shortness of breath symptomatology. Such therapies for MR reduction may also have a positive effect on the filling profile of the left ventricle (LV) and the restrictive LV physiology that can result with MR. These pathophysiologic issues indicate the potential benefits of MR therapy, but also indicate the complexity of the system and the need for a therapy to focus beyond the MR level or grade.

Some therapies for treating MR may worsen other (non-MR) existing pathologic conditions or create new pathologic conditions. One of the conditions to be managed is mitral stenosis or creation of an inflow gradient. That is, if a prosthetic valve system is used that does not allow for sufficient LV inflow without elevated filling pressures, then some benefits of MR reduction may be dissipated or lost. An additional condition to be managed is left ventricular outflow tract (LVOT) obstruction or creation of high LVOT pressure gradients. That is, if a prosthetic valve system is used that does significantly obstructs the LVOT, then some benefits of MR reduction may be dissipated or lost. Also, if the procedure results in damage to atrial tissue at surgery, it can increase the likelihood of the negative physiologic effect of atrial fibrillation. Further, some prosthetic valve systems may increase the risk of higher LV wall stress through an increase in LV size (LV geometry). Due to the integral relationship of the mitral valve with LV geometry through the papillary and chordal apparatus, LV wall stress levels can be directly affected resulting in alterations of LV filling and contraction mechanics. Accordingly, in some circumstances, a prosthetic valve system that worsens the geometry of the LV can counter the benefits of MR reduction because of the alteration of contractile physiology.

SUMMARY

This document describes prosthetic heart valves, such as prosthetic mitral valves that can be implanted using transcatheter techniques. For example, some embodiments of a transcatheter mitral valve delivery system and method described herein can be deployed to interface and anchor in cooperation with the native anatomical structures of a mitral valve. In addition, this document describes prosthetic heart valve systems that interface with native mitral valve structures to create a fluid seal, thereby minimizing MR and paravalvular leaks after implantation. Further, this document describes prosthetic heart valve systems and techniques that, in particular embodiments, are configured to manage blood flow through the left ventricular outflow tract (LVOT) and to thereby reduce the risk of full or partial blockages of the LVOT. In addition, some embodiments of the prosthetic heart valve systems and techniques described herein may be configured to reduce the risk of interference between the prosthetic valves and chordae tendineae of the native mitral valve leaflets, which can advantageously facilitate or preserve the geometry of the LV.

Particular embodiments described herein include a mitral valve replacement system for a heart. The system may include an expandable anchor assembly configured to implant at a native mitral valve, and the expandable anchor assembly may include a first expandable frame that is adjustable from a delivery condition to an expanded condition. The system may also include a first delivery sheath device having a distal end insertable into a left atrium and being configured to express the anchor assembly out from the distal end such that the anchor assembly expands within the left atrium to the expanded condition. Optionally, the system may further include a pusher instrument releasably attachable to the expandable anchor frame and being configured to longitudinally advance the anchor assembly within the left atrium towards an annulus of the native mitral valve while the anchor assembly is in the expanded condition. Also, the system may include an artificial valve assembly comprising a second expandable frame that is adjustable from a compressed condition to a deployed condition to selectively engage with the anchor assembly while the anchor assembly is in the expanded condition.

Some embodiments described herein include a method for deploying a prosthetic mitral valve system within a native mitral valve of a patient. The method may include navigating a first delivery sheath within the patient such that a distal end of the first delivery sheath is positioned within a left atrium. The method may also include expressing an anchor assembly of the prosthetic heart valve system from the distal end of the first delivery sheath such that the anchor assembly at least partially expands while located within the left atrium. Further, the method may include, after expressing the anchor assembly within the left atrium, moving the anchor assembly towards an annulus of the native mitral valve.

Various embodiments described herein include a prosthetic mitral valve system. The system may include a valve assembly, which may include a frame member defining an outer profile and an interior frame member space, and an occluder disposed within the interior frame member space. The occluder may have an open configuration and a closed configuration. The frame member comprises a proximal end frame portion and a distal end frame portion. Optionally, an outer periphery of the distal end frame portion may include a generally flat region and a generally round region, and at least some portions of the generally flat region may extend toward the interior frame member space.

Particular embodiments described herein include a method of using a prosthetic mitral valve system. The method may include advancing a valve assembly of the prosthetic mitral valve system toward an annulus of a native mitral valve. Optionally, the valve assembly may include a frame member defining an outer profile and an interior frame member space, and occluder disposed within the interior frame member space. The frame member may include a proximal end frame portion and a distal end frame portion. An outer periphery of the distal end frame portion may optionally include a generally flat region and a generally round region, and at least some portions of the generally flat region extend toward the interior frame member space. The method may also include anchoring the valve assembly at the native mitral valve such that the generally flat region is adjacent to an anterior native leaflet of the native mitral valve.

Some embodiments described herein include a prosthetic mitral valve system that is implantable at a native mitral valve. The prosthetic mitral valve system may include an anchor assembly defining an interior anchor assembly space and longitudinal axis. The anchor assembly may include an expandable anchor frame including a hub and a sub-annular support arm extending from the hub. The sub-annular support arm may extend to an anchor foot having a surface configured for engagement with a sub-annular gutter of the native mitral valve. The system may further include a valve assembly that includes an expandable valve frame defining an outer profile and an interior frame member space, and an occluder disposed within the interior frame member space. The valve assembly may be releasably engageable with the anchor assembly within the interior anchor assembly space. Optionally, a distance measured parallel to the longitudinal axis from a distal-most end of the anchor assembly to the surface is at least 14 millimeters.

Various embodiments described herein include a method of using a prosthetic mitral valve system. The method may include advancing an anchor assembly of the prosthetic mitral valve system toward an annulus of a native mitral valve. The anchor assembly may an interior anchor assembly space and longitudinal axis, and the anchor assembly may include an expandable anchor frame including a hub and one or more sub-annular support arms extending from the hub. Each of the one or more sub-annular support arm may extend to an anchor foot configured to engage with a sub-annular gutter of the native mitral valve. The method may further include engaging the anchor assembly of the prosthetic mitral valve system with tissue proximate the native mitral valve such that each anchor foot is engaged with the sub-annular gutter, and (optionally) such that the hub is positioned distal of the distal-most area of coaptation between anterior and post leaflets of the native mitral valve.

Particular embodiments described herein include a method of sealing between a prosthetic mitral valve system and native leaflets of a mitral valve. The method may include anchoring an anchor assembly of the prosthetic mitral valve system with tissue proximate to an annulus of a native mitral valve. Optionally, the anchor assembly defines an interior anchor assembly space and longitudinal axis, and the anchor assembly may include an expandable anchor frame including a hub and one or more sub-annular support arms extending from the hub. Each of the one or more sub-annular support arm may extend to an anchor foot that engages with a sub-annular gutter of the native mitral valve. The method may further include delivering a valve assembly of the prosthetic mitral valve system to engage with the anchor assembly. Optionally, the valve assembly may include: an expandable valve frame defining an outer profile and an interior frame member space, a tissue layer disposed over at least a portion of the outer profile, and an occluder disposed within the interior frame member space. The tissue layer of the valve assembly can abut with native leaflets of the mitral valve while each anchor foot of the anchor assembly is engaged with the sub-annular gutter.

Some embodiments described herein include a prosthetic mitral valve system. The system may include an anchor assembly comprising an expandable anchor frame and a set of sub-annular anchor feet configured to engage with a sub-annular gutter of the native mitral valve. The system may further include a valve assembly that includes: an expandable valve frame defining an outer profile and an interior frame member space, a tissue layer disposed over at least a portion of the outer profile, and an occluder mounted within the interior frame member space. Optionally, an outwardly facing periphery of the tissue layer along the valve assembly is positioned to abut native leaflets of the mitral valve when the set of anchor feet of the anchor assembly is engaged with the sub-annular gutter.

Various embodiments described herein include a method for deploying a prosthetic mitral valve system within a native mitral valve of a patient. The method may comprise navigating a delivery sheath such that a distal end of the delivery sheath is positioned within a left atrium of the patient. Also, the method may include expressing, in the left atrium, an anchor assembly of the prosthetic mitral valve system. A distal pusher instrument may be releasably engaged with the anchor assembly. The method may further include engaging the anchor assembly with the native mitral valve while the distal pusher instrument remains engaged with the anchor assembly. The method may also include expressing, in the left atrium, a valve assembly of the prosthetic mitral valve system. Optionally, the valve assembly may slidably engaged with an exterior of the distal pusher instrument. The method may further include moving the valve assembly into an interior space defined by the anchor assembly. The moving may optionally include sliding the valve assembly along the exterior of the distal pusher catheter while the distal pusher catheter remains engaged with to the anchor assembly. The method may also include, after moving the valve assembly, mounting the valve assembly with the anchor assembly. Further, the method may include, after mounting the valve assembly, decoupling the distal pusher instrument from the anchor assembly.

Particular embodiments described herein include an implantable medical device delivery system. The system may include a first deflectable catheter defining a first lumen therethrough, and a distal end portion of the first deflectable catheter may be controllably laterally deflectable. The system may also include a first device delivery sheath slidably disposable within the first lumen, and the first device delivery sheath may define a second lumen therethrough. The system may further include a first device control sheath slidably disposable within the second lumen, and the first device control sheath may define a third lumen therethrough and one or more first device control wire lumens. The system may also include a second deflectable catheter slidably disposable within the third lumen, and the second deflectable catheter may define a fourth lumen therethrough. A distal end portion of the second deflectable catheter may be controllably laterally deflectable. The system may further include a device pusher catheter slidably disposable within the fourth lumen, and the device pusher catheter may define a fifth lumen therethrough. A distal end portion of the device pusher catheter may be configured to releasably couple with a first implantable medical device.

Some embodiments described herein include a method for deploying a prosthetic mitral valve system within a native mitral valve of a patient. The method may include expanding an anchor assembly of the prosthetic heart valve system within a left atrium, while the anchor assembly is releasably secured to a first delivery catheter, such that the anchor assembly at least partially expands while located within the left atrium. The method may optionally include, after expressing the anchor assembly within the left atrium, panning or rotating the anchor assembly within the left atrium by articulating a tip portion of the first delivery catheter.

Various embodiments described herein include a method for deploying a prosthetic mitral valve system within a native mitral valve of a patient. The method may include expressing a valve assembly of the prosthetic heart valve system within a left atrium, while the valve assembly is releasably secured to a valve delivery catheter, such that the valve assembly at least partially expands while located within the left atrium. The method may optionally include, after expressing the valve assembly within the left atrium, panning or rotating the valve assembly within the left atrium by articulating a tip portion of the valve delivery catheter.

Some or all of the embodiments described herein may provide one or more of the following advantages. First, some embodiments of the prosthetic mitral valve systems provided herein can be used in a completely percutaneous/transcatheter mitral replacement procedure that is safe, reliable, and repeatable by surgeons of a variety of different skill levels. For example, in some implementations the prosthetic mitral valve system can establish a reliable and consistent anchor/substrate to which the valve/occluder structure subsequently engages. Thus, the prosthetic mitral valve system can be specifically designed to make use of the geometry/mechanics of the native mitral valve to create sufficient holding capability. In one particular aspect, the anatomical gutter found below a native mitral valve annulus can be utilized as a site for anchoring the prosthetic mitral valve system, yet the anchoring structure can be deployed in a matter that maintains native leaflet function of the mitral valve, thereby providing the ability to completely separate and stage the implantation of the components of the prosthetic mitral valve system. Accordingly, some embodiments of the prosthetic mitral valve systems described herein are configured to be implanted in a reliable, repeatable, and simplified procedure that is broadly applicable to a variety of patients and physicians, while also employing a significantly less invasive method.

Second, some embodiments of the prosthetic mitral valve systems described herein facilitate effective long lasting MR reduction without creating negative physiologic consequences to the cardiopulmonary system (heart, lungs, peripheral vasculature) including stenosis, LV wall stress, and atrial fibrillation. Also, the system may provide a safe and durable anchoring effect at the native mitral valve to provide an effective mitral regurgitation therapy as well as providing structures that provide sealing benefits and avoid significant impairment of the chordal interface of the native mitral valve leaflets.

Third, in particular embodiments, the prosthetic mitral valve system can be delivered to the native mitral valve using a technique in which an expandable frame of the anchor component is at least partially expanded in the left atrium prior to reaching the mitral valve location. As such, in addition to facilitating the delivery of the anchor, the heart surgeon or other user can visualize the expanded component (and its orientation) within the heart before it is advanced to the annulus of the mitral valve (thereby permitting the user the opportunity to laterally pivot (rotate, pan, re-orient) the expanded component prior to reaching the annulus).

Fourth, some embodiments of the prosthetic mitral valve systems described herein can be configured to partially extend into the left ventricle after implantation, yet may include a profile shape that is configured to reduce the likelihood of obstructing blood flow through the LVOT. Accordingly, even though some portions of the prosthetic mitral valve systems extend into the left atrium above the mitral valve annulus (supra-annular) and other portions extend into the left ventricle below the mitral valve annulus (sub-annular), the prosthetic mitral valve system is designed to account for the natural LVOT and thereby reduce the risk of full or partial blockages of the LVOT.

Fifth, in particular embodiments, the prosthetic mitral valve system can include two different expandable components (e.g., an anchor assembly and a valve assembly) that are separately delivered to the implantation site, and both components can abut and engage with native heart tissue at the mitral valve. For example, the first component (e.g., the anchor assembly) can be configured to engage with the heart tissue that is at or proximate to the annulus of the native mitral valve, and the second component (e.g., the valve assembly) can be configured to provide a seal interface with native valve leaflets of the mitral valve.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 37 is a commissural cross-sectional view of a heart showing an anchor assembly of a prosthetic mitral valve engaged in the sub-annular gutter of the native mitral valve. Chordae tendineae in the left ventricle are also depicted.

FIG. 38 is a lateral cross-section of a left ventricle of a heart showing an anchor assembly of a prosthetic mitral valve engaged in the sub-annular gutter of the native mitral valve. Chordae tendineae in the left ventricle are also depicted.

FIG. 41 is a side view of a valve assembly frame showing control wires that are threaded through portions of the valve assembly frame.

FIG. 42 is a schematic diagram of a threading pattern of a proximal control wire corresponding to the valve assembly frame embodiment of FIG. 41.

FIG. 43 is a schematic diagram of a threading pattern of a mid-body control wire corresponding to the valve assembly frame embodiment of FIG. 41.

Like reference symbols in the various drawings indicate like elements.

DETAILED DESCRIPTION OF ILLUSTRATIVE EMBODIMENTS

This disclosure describes embodiments of a prosthetic heart valve system, such as prosthetic mitral valve systems, and transcatheter systems and methods for implanting prosthetic heart valve systems. In some embodiments, the prosthetic mitral valve system can be deployed to interface and anchor in cooperation with the native anatomical structures of a mitral valve (and, optionally, in a manner that permits the continued natural function of the chordae tendineae of the native mitral valve leaflets even after the anchor component is deployed). As described herein, the prosthetic mitral valve system can be deployed in a manner that interfaces with native mitral valve structures to create a fluid seal, thereby minimizing MR and paravalvular leaks after implantation. As described in more detail below, FIGS. 1-17 and 39-43 describe a transcatheter mitral valve delivery system and method by which the prosthetic mitral valve system can be deployed to interface and anchor in cooperation with the anatomical structures of a native mitral valve. Also, in FIGS. 18-32, prosthetic mitral valve features are described by which the prosthetic valves interface with native mitral valve structures to create a fluid seal, thereby reducing the likelihood of MR and paravalvular leaks. In FIGS. 33-36, prosthetic mitral valve features and techniques are described for managing blood flow through the left ventricular outflow tract (LVOT). In FIGS. 37-38, prosthetic mitral valve features and techniques are described for reducing the risk of interference between the prosthetic valves and chordae tendineae.

Figure 1:
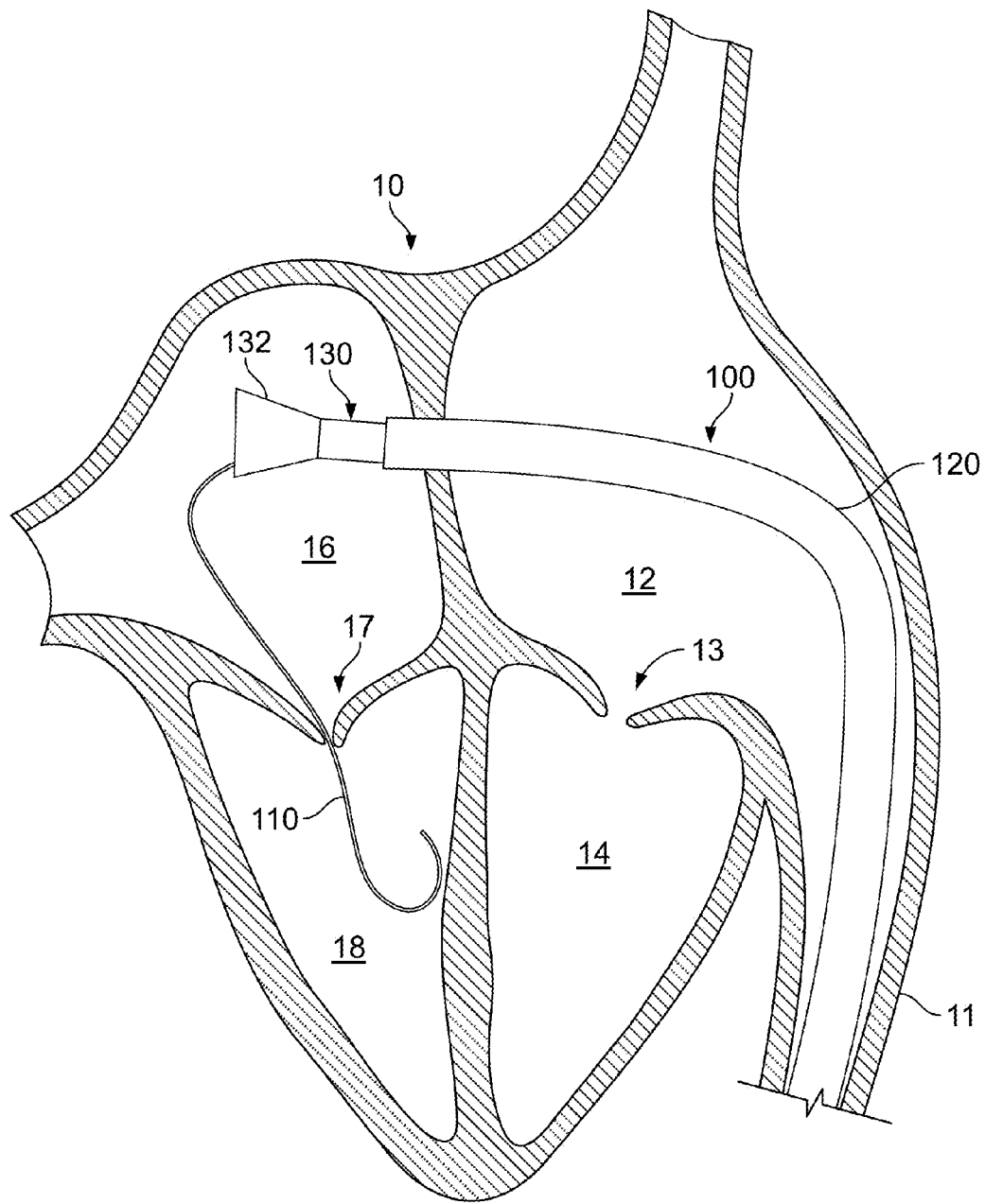
FIG. 1 is a perspective view of a portion of a prosthetic mitral valve deployment system in a cross-sectional view of a native human heart, in accordance with some embodiments.

Referring to FIG. 1, an example transcatheter mitral valve delivery system 100 can be navigated through a patient's vasculature to obtain access to the patient's heart 10. The transcatheter delivery system 100 facilitates implantation of a prosthetic mitral valve in a beating heart 10 using a percutaneous, vessel cutdown, or minimally invasive technique (without open-chest surgery). In some implementations, the transcatheter delivery system 100 is used in conjunction with one or more imaging modalities such as x-ray fluoroscopy, echocardiography, magnetic resonance imaging, computed tomography (CT), and the like.

The heart 10 (depicted in cross-section from a posterior perspective) includes a right atrium 12, a right ventricle 14, a left atrium 16, and a left ventricle 18. A tricuspid valve 13 separates the right atrium 12 from the right ventricle 14. A mitral valve 17 separates the left atrium 16 from the left ventricle 18. An atrial septum 15 separates the right atrium 12 from the left atrium 16. An inferior vena cava 11 is confluent with the right atrium 12. It should be understood that this depiction of the heart 10 is somewhat stylized. The same is true for FIGS. 2-4. FIGS. 1-4 provide general depictions of the approach to the mitral valve 17 that is used in some implementations. But, the commissural cross-sectional views of FIG. 5 and thereafter more accurately depict the orientation of the prosthetic mitral valves in relation to the heart 10.

In the depicted embodiment, the delivery system 100 includes a guidewire 110, a primary deflectable catheter 120, and an anchor delivery sheath 130. Additional components of the delivery system 100 will be described further below. The anchor delivery sheath 130 is slidably (and rotationally) disposed within a lumen of the primary deflectable catheter 120. The guidewire 110 is slidably disposed within a lumen of the anchor delivery sheath 130. In this depiction, the anchor delivery sheath 130 has been partially extended relative to the primary deflectable catheter 120, allowing a flared portion 132 to expand outward, as described further below.

In the depicted implementation, the guidewire 110 is installed into the heart 10 prior to the other components of the delivery system 100. In some embodiments, the guidewire 110 has a diameter of about 0.035 inches (about 0.89 mm). In some embodiments, the guidewire 110 has a diameter in a range of about 0.032 inches to about 0.038 inches (about 0.8 mm to about 0.97 mm). In some embodiments, the guidewire 110 has a diameter smaller than 0.032 inches (about 0.80 mm) or larger than 0.038 inches (about 0.97 mm). In some embodiments, the guidewire 110 is made of materials such as, but not limited to, nitinol, stainless steel, high-tensile-strength stainless steel, and the like, and combinations thereof. The guidewire 110 may include various tip designs (e.g., J-tip, straight tip, etc.), tapers, coatings, covers, radiopaque (RO) markers, and other features.

In some implementations, the guidewire 110 is percutaneously inserted into a femoral vein of the patient. The guidewire 110 is routed to the inferior vena cava 11 and into the right atrium 12. After creating an opening in the atrial septum 15 (e.g., a trans-septal puncture of the fossa ovalis), the guidewire 110 is routed into the left atrium 16. Lastly, the guidewire 110 is routed through the mitral valve 17 and into the left ventricle 18. In some implementations, the guidewire 110 can be installed into the heart 10 along other anatomical pathways. The guidewire 110 thereafter serves as a rail over which other components of the delivery system 100 are passed.

In the depicted implementation, the primary deflectable catheter 120 is installed by pushing it over the guidewire 110. In some implementations, a dilator tip is used in conjunction with the primary deflectable catheter 120 as the primary deflectable catheter 120 is advanced over the guidewire 110. Alternatively, a balloon catheter could be used as the initial dilation means. After the distal end of the primary deflectable catheter 120 reaches the left atrium 16, the dilator tip can be withdrawn. In some embodiments, the distal end portion of the primary deflectable catheter 120 is steerable. Using steering, the distal end portion of the primary deflectable catheter 120 can be oriented as desired in order to navigate the patient's anatomy. For example, the primary deflectable catheter 120 can be angled within the right atrium 12 to navigate the primary deflectable catheter 120 from the inferior vena cava 11 to the atrial septum 15.

In some embodiments, the primary deflectable catheter 120 has an outer diameter of about 28 Fr (about 9.3 mm). In some embodiments, the primary deflectable catheter 120 has an outer diameter in the range of about 26 Fr to about 34 Fr (about 8.7 mm to about 11.3 mm). In some embodiments, the primary deflectable catheter 120 has an outer diameter in the range of about 20 Fr to about 28 Fr (about 6.7 mm to about 9.3 mm).

The primary deflectable catheter 120 can comprise a tubular polymeric or metallic material. For example, in some embodiments the primary deflectable catheter 120 can be made from polymeric materials such as, but not limited to, polytetrafluoroethylene (PTFE), fluorinated ethylene propylene (FEP), HYTREL®, nylon, PICOFLEX®, PEBAX®, TECOFLEX®, and the like, and combinations thereof. In alternative embodiments, the primary deflectable catheter 120 can be made from metallic materials such as, but not limited to, nitinol, stainless steel, stainless steel alloys, titanium, titanium alloys, and the like, and combinations thereof. In some embodiments, the primary deflectable catheter 120 can be made from combinations of such polymeric and metallic materials (e.g., polymer layers with metal braid, coil reinforcement, stiffening members, and the like, and combinations thereof).

The example delivery system 100 also includes the anchor delivery sheath 130. In some implementations, after the primary deflectable catheter 120 is positioned with its distal end in the left atrium 16, the anchor delivery sheath 130 is installed into a lumen of the primary deflectable catheter 120 (over the guidewire 110) and advanced through the primary deflectable catheter 120. As described further below, in some embodiments the anchor delivery sheath 130 is preloaded with a prosthetic valve anchor assembly and other components of the delivery system 100.

In some embodiments, the anchor delivery sheath 130 can be made from the materials described above in reference to the primary deflectable catheter 120. In some embodiments, the anchor delivery sheath 130 has an outer diameter in the range of about 20 Fr to about 28 Fr (about 6.7 mm to about 9.3 mm). In some embodiments, the anchor delivery sheath 130 has an outer diameter in the range of about 14 Fr to about 24 Fr (about 4.7 mm to about 8.0 mm).

In the depicted embodiment, the anchor delivery sheath 130 includes a flared distal end portion 132. In some embodiments, no such flared distal end portion 132 is included. The flared distal end portion 132 can collapse to a lower profile when constrained within the primary deflectable catheter 120. When the flared distal end portion 132 is expressed from the primary deflectable catheter 120, the flared distal end portion 132 can self-expand to the flared shape. In some embodiments, the material of the flared distal end portion 132 includes pleats or folds, may be a continuous flared end or may be separated into sections such as flower pedals, and may include one or more resilient elements that bias the flared distal end portion 132 to assume the flared configuration in the absence of restraining forces (such as from containment within the primary deflectable catheter 120). The flared distal end portion 132 can be advantageous, for example, for recapturing the anchor assembly within the lumen of the anchor delivery sheath 130 after the anchor assembly has been expressed from the flared distal end portion 132.

In some embodiments, the maximum outer diameter of the flared distal end portion 132 is in a range of about 30 Fr to about 34 Fr (about 10.0 mm to about 11.3 mm). In some embodiments, the maximum outer diameter of the flared distal end portion 132 is in a range of about 32 Fr to about 44 Fr (about 10.7 mm to about 14.7 mm). In some embodiments, the maximum outer diameter of the flared distal end portion 132 is in a range of about 24 Fr to about 30 Fr (about 8.0 mm to about 10.0 mm). In some embodiments, the maximum outer diameter of the flared distal end portion 132 is less than about 24 Fr (about 8.0 mm) or greater than about 44 Fr (about 14.7 mm).

Figure 2:
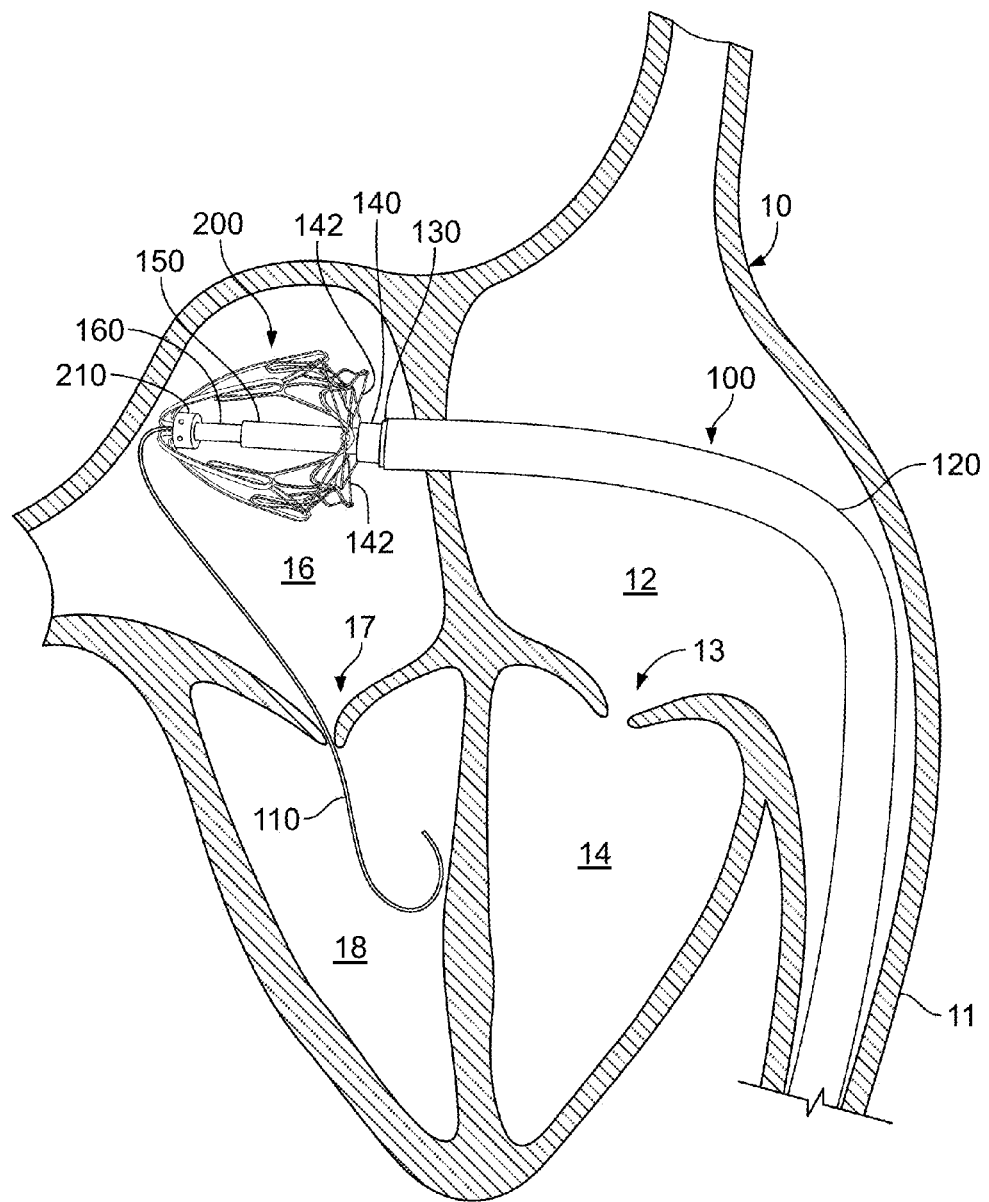
FIG. 2 shows a perspective view of a prosthetic mitral valve anchor assembly in the left atrium of the heart after the anchor assembly has emerged from an anchor delivery sheath of the deployment system of FIG. 1

Referring to FIG. 2, additional components of the example delivery system 100 can include a proximal control sheath 140, a secondary deflectable catheter 150, and a distal pusher catheter 160. The proximal control sheath 140 is slidably disposed within a lumen of the anchor delivery sheath 130. The secondary deflectable catheter 150 is slidably disposed within a lumen of the proximal control sheath 140. The distal pusher catheter 160 is slidably disposed within a lumen of the secondary deflectable catheter 150. These components of the delivery system 100 can be manipulated by a clinician operator to control the position and orientation of an anchor assembly 200. The anchor assembly 200 is slidably disposed over the guidewire 110.

In some implementations of delivery system 100, one or more of the proximal control sheath 140, the secondary deflectable catheter 150, the distal pusher catheter 160, and the anchor assembly 200 have been loaded into the anchor delivery sheath 130 prior to the advancement of the anchor delivery sheath 130 into the primary deflectable catheter 120 as shown in FIG. 1. That is, in some cases the proximal control sheath 140, the secondary deflectable catheter 150, the distal pusher catheter 160, and/or the anchor assembly 200 are already installed in the anchor delivery sheath 130 as the anchor delivery sheath 130 is distally advanced into the primary deflectable catheter 120 to attain the arrangement shown in FIG. 1. In other implementations, one or more of the proximal control sheath 140, the secondary deflectable catheter 150, the distal pusher catheter 160, and the anchor assembly 200 are distally advanced into the anchor delivery sheath 130 after the anchor delivery sheath 130 has been advanced into the primary deflectable catheter 120 to attain the arrangement shown in FIG. 1.

The distal pusher catheter 160 is releasably coupled with a hub 210 of the anchor assembly 200. A proximal end of the anchor assembly 200 is also releasably coupled to the proximal control sheath 140 by one or more control wires 142. While the depicted embodiment includes one control wire 142, in some embodiments two, three, four, five, or more than five control wires are included.

Figure 39:
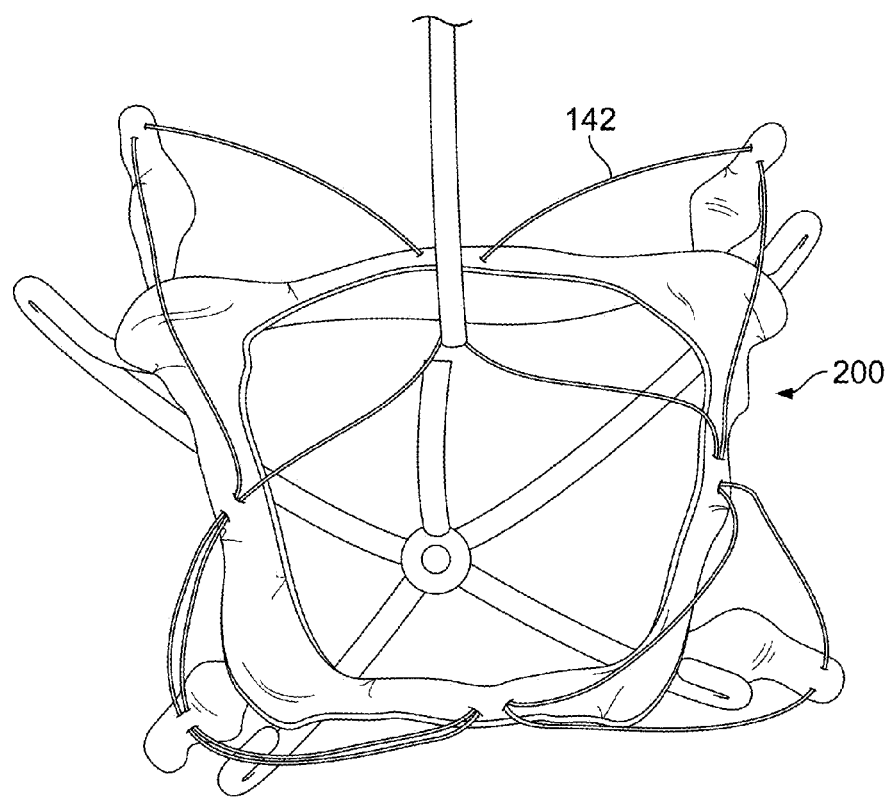
FIG. 39 is a perspective view of an anchor assembly showing control wires that are threaded through portions of the anchor assembly.
Figure 40:
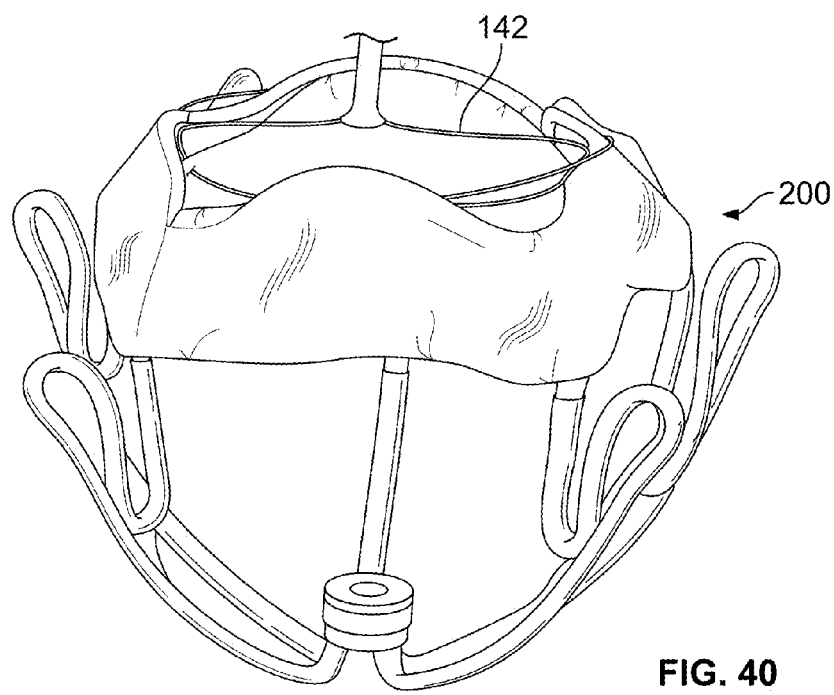
FIG. 40 is another perspective view of an anchor assembly showing control wires that are threaded through portions of the anchor assembly.

Referring to FIGS. 39 and 40, the control wire 142 is shown in an example engagement pattern with the anchor assembly 200. In the depicted embodiment, the control wire 142 is threaded through a plurality of proximal portions of the anchor assembly 200. In the depicted embodiment, the control wire 142 is configured in a lasso arrangement. Accordingly, a tensioning of the control wire 142 will cause at least the proximal end of the anchor assembly 200 to contract. Conversely, a removal of tension from the control wire 142 will allow the anchor assembly 200 to expand. In some embodiments, the control wire 142 is threaded through eyelets that are disposed on various positions on the anchor assembly 200. In some embodiments, the control wire 142 is threaded through attachment features that are disposed on various positions on the covering or frame of the anchor assembly 200. The control wire 142 can be tensioned or relaxed to arrive at a desired extent of expansion of the proximal end of the anchor assembly 200 (e.g., the atrial holding features 240a, 240b, 240c, and 240d, and/or the undulating supra-annular ring 250). Multiple control wires 142 could also be used to achieve asymmetric, controlled expansion of the anchor assembly 300.

Referring again to FIG. 2, the position of the anchor assembly 200 can be controlled by manipulating the positions of the distal pusher catheter 160 and/or the proximal control sheath 140. For example, in the depicted embodiment the anchor assembly 200 can be expressed out from the anchor delivery sheath 130 (as shown in FIG. 2) by moving the distal pusher catheter 160 and/or the proximal control sheath 140 distally in relation to the anchor delivery sheath 130. In some implementations, the expression of the anchor assembly 200 is caused by proximally pulling back the anchor delivery sheath 130 while generally maintaining the positions of the distal pusher catheter 160 and/or the proximal control sheath 140. In some implementations, the expression of the anchor assembly 200 is caused by a combination of proximally pulling back the anchor delivery sheath 130 while distally extending the positions of the distal pusher catheter 160 and/or the proximal control sheath 140.

As the anchor assembly 200 emerges from the confines of the anchor delivery sheath 130, the anchor assembly 200 expands from a low-profile delivery configuration to a partially expanded configuration (as shown in FIG. 2). The extent of expansion of the anchor assembly 200 can be at least partially controlled by the relative positioning of the proximal control sheath 140 in relation to the distal pusher catheter 160. For instance, as the proximal control sheath 140 is moved proximally in relation to the distal pusher catheter 160, the anchor assembly 200 is axially elongated and radially contracted. Conversely, as the proximal control sheath 140 is moved distally in relation to the distal pusher catheter 160, the anchor assembly 200 is axially shortened and radially expanded. In some implementations, this control of the radial size of the anchor assembly 200 is used by a clinician during the process of deploying the anchor assembly 200 within the native mitral valve 17, as described further below. As described further below, the control wire 142 can also be used to control some radial expansion of the anchor assembly 300 (without changing the relative distance of the proximal control sheath 140 in relation to the distal pusher catheter 160).

It should be understood that the prosthetic mitral valves provided herein are comprised of an anchor assembly 200 and a separable valve assembly (e.g., refer to FIGS. 14-20). The anchor assembly 200 is deployed to an arrangement interfacing within the native mitral valve 17 prior to deployment of the valve assembly. Said differently, after implanting the anchor assembly 200 within the native mitral valve 17, the valve assembly can then be deployed within the anchor assembly 200 and within the native mitral valve 17 (as described further below). Therefore, it can be said that the prosthetic mitral valves provided herein are deployed using a staged implantation method. That is, the anchor assembly 200 is deployed in one stage, and the valve assembly is deployed in a subsequent stage. In some implementations, the deployment of the valve assembly takes place right after the deployment of the anchor assembly 200 (e.g., during the same medical procedure). In some implementations, the deployment of the valve assembly takes place hours, days, weeks, or even months after the deployment of the anchor assembly 200 (e.g., during a subsequent medical procedure).

The staged implantation method of the prosthetic mitral valves provided herein is facilitated by the fact that when the anchor assembly 200 itself is implanted within the native mitral valve 17, the native mitral valve 17 continues to function essentially as before the implantation of the anchor assembly 200 without a significant impact on cardiovascular physiology. That is the case because, as described further below, the anchor assembly 200 interfaces and anchors within structural aspects of the native mitral valve 17 without substantially interfering with the leaflets or chordae tendineae of the native mitral valve 17.

Still referring to FIG. 2, in the depicted arrangement the distal end portion of the secondary deflectable catheter 150 is located at least partially internally within the anchor assembly 200. The secondary deflectable catheter 150 can be manipulated by a clinician operator to reversibly bend the distal end portion of the secondary deflectable catheter 150. As the secondary deflectable catheter 150 is bent by the clinician, other components of the delivery system 100 may bend along with the secondary deflectable catheter 150. For example, one or more of the distal pusher 160 and the proximal control sheath 140 may bend in response to the bending of the deflectable catheter 150. Because the anchor assembly 200 is coupled to the distal pusher 160 and the proximal control sheath 140, the anchor assembly 200 can, in turn, be rotated by bending the secondary deflectable catheter 150.

Figure 3:
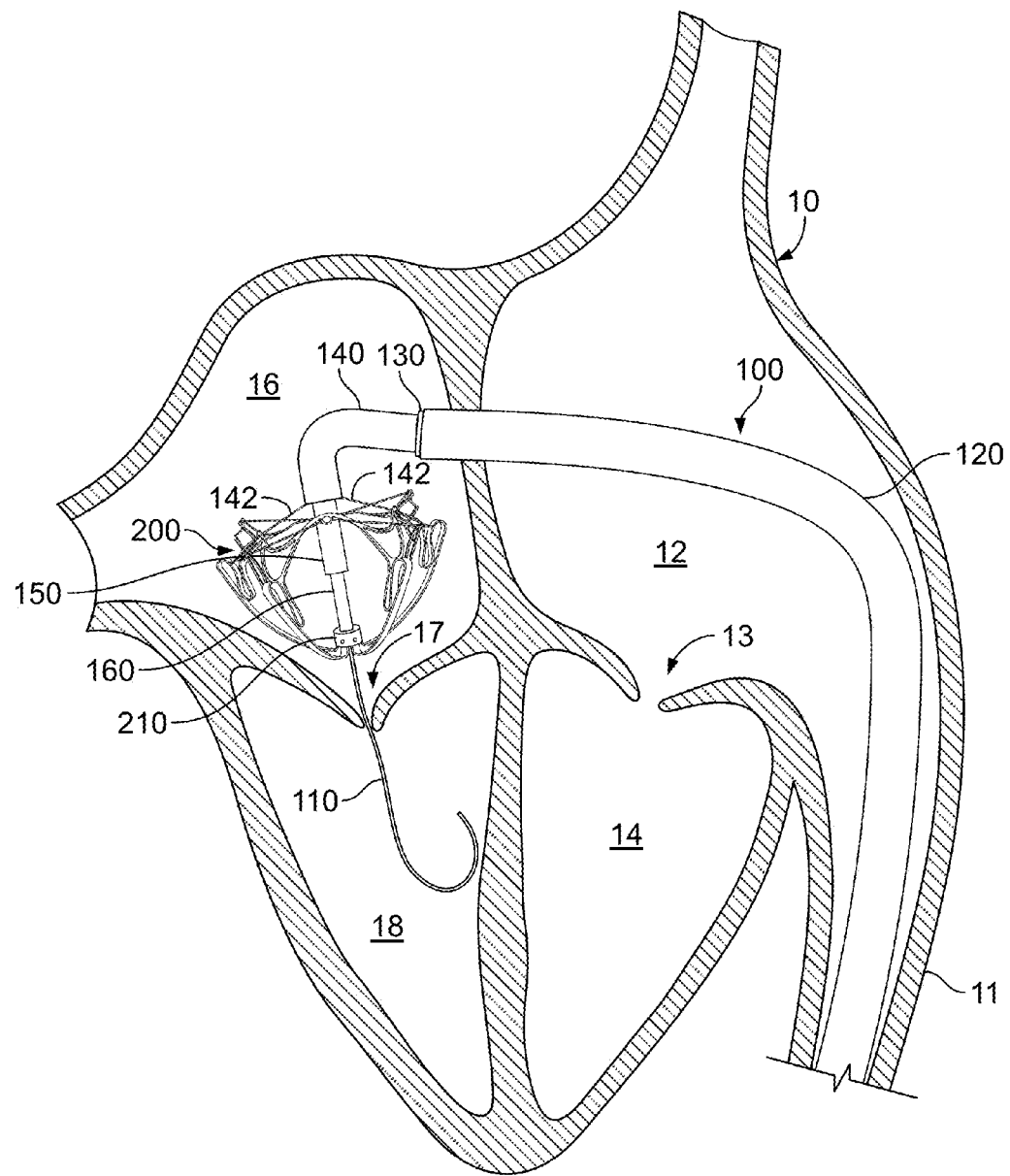
FIG. 3 shows a perspective view of the anchor assembly of FIG. 2 after being rotated in the left atrium so as to orient the anchor assembly generally perpendicular to the native mitral valve.

Referring to FIG. 3, as described above, the secondary deflectable catheter 150 can be articulated (also referred to as steered, deflected, bent, curved, etc.) to pivot laterally (pan, rotate, etc.) the anchor assembly 200 while the anchor assembly 200 is within the left atrium 16. Such rotation of the anchor assembly 200 is advantageous, for example, to orient the anchor assembly 200 in a desired relationship to the native mitral valve 17 in preparation for implanting the anchor assembly 200 within the native mitral valve 17. In some implementations, it is desirable to orient the anchor assembly 200 so that its longitudinal axis is generally perpendicular to the native mitral valve 17. The lateral pivoting of the partially or fully expanded anchor assembly 200 within the atrium 16 may be advantageous versus having to pivot laterally the anchor assembly 200 while it is still constrained within a delivery sheath, as the latter assembly is a relatively large and stiff catheter assembly.

In preparation for engaging the anchor assembly 200 with the native mitral valve 17, the clinician operator may manipulate the radial size of the anchor frame 200 so that the anchor frame 200 can be passed through the native mitral valve 17 without damaging the native mitral valve 17. For example, the clinician can move the proximal control sheath 140 proximally in relation to the distal pusher catheter 160 to radially contract the anchor assembly 200. With the anchor assembly 200 radially contracted, the anchor frame 200 can be safely passed through the native mitral valve 17 without damaging the native mitral valve 17.

Figure 4:
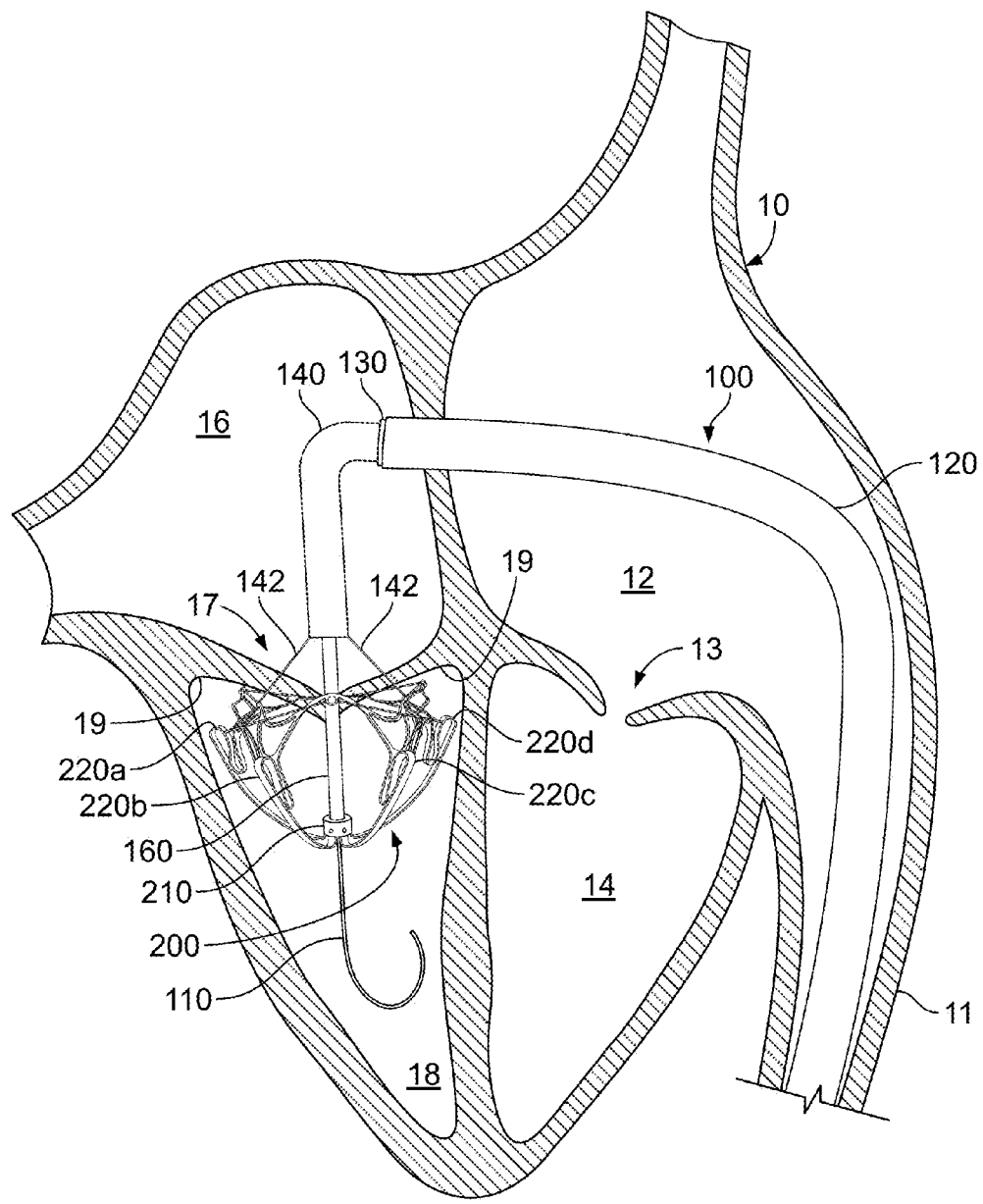
FIG. 4 shows a perspective view of the anchor assembly of FIG. 3 after being partially advanced through the native mitral valve so as to position projections of the anchor assembly below a sub-annular gutter of the native mitral valve.

Referring to FIG. 4, while the secondary deflectable catheter 150 is retained in its bent configuration as described in reference to FIG. 3, the distal pusher catheter 160 and the proximal control sheath 140 can be simultaneously advanced. Because the distal pusher catheter 160 is releasably coupled to the hub 210 of the anchor assembly 200, and because the proximal control sheath 140 is releasably coupled to the proximal end of the anchor assembly 200 via the one or more wires 142a and 142b, simultaneous advancement of the distal pusher catheter 160 and the proximal control sheath 140 results in advancement of the anchor assembly 200. The anchor assembly 200 is advanced such that the distal end of anchor assembly 200 is within the left ventricle 18 while the proximal end of the anchor assembly 200 is within the left atrium 16. Hence, some portions of the anchor assembly 200 are on each side of the native mitral valve 17.

In the depicted embodiment, the anchor assembly 200 includes four anchor feet: a left anterior foot 220a, a left posterior foot 220b, a right posterior foot 220c, and a right anterior foot 220d. In some embodiments, fewer or more anchor feet may be included (e.g., two, three, five, six, or more than six). In some embodiments, the anchor feet 220a, 220b, 220c, and 220d are portions of the anchor assembly 200 that are configured for contact with a sub-annular gutter 19 of the native mitral valve 17, without penetrating tissue of the native mitral valve 17. Accordingly, the anchor feet 220a, 220b, 220c, and 220d have atraumatic surfaces that are generally comparable to feet. However, in some embodiments one or more of the anchor feet 220a, 220b, 220c, and 220d are configured to penetrate tissue and may have anchor features such as barbs, coils, hooks, and the like.

In the arrangement of FIG. 4, the anchor feet 220a, 220b, 220c, and 220d are positioned below the sub-annular gutter 19. In this arrangement, the radial size of the anchor assembly 200 can be increased to align the anchor feet 220a, 220b, 220c, and 220d with the sub-annular gutter 19. For example, the clinician can move the proximal control sheath 140 distally in relation to the distal pusher catheter 160 to radially expand the anchor assembly 200 to align the anchor feet 220a, 220b, 220c, and 220d with the sub-annular gutter 19. Such alignment can be performed in preparation for seating the anchor feet 220a, 220b, 220c, and 220d within the sub-annular gutter 19.

Figure 5:
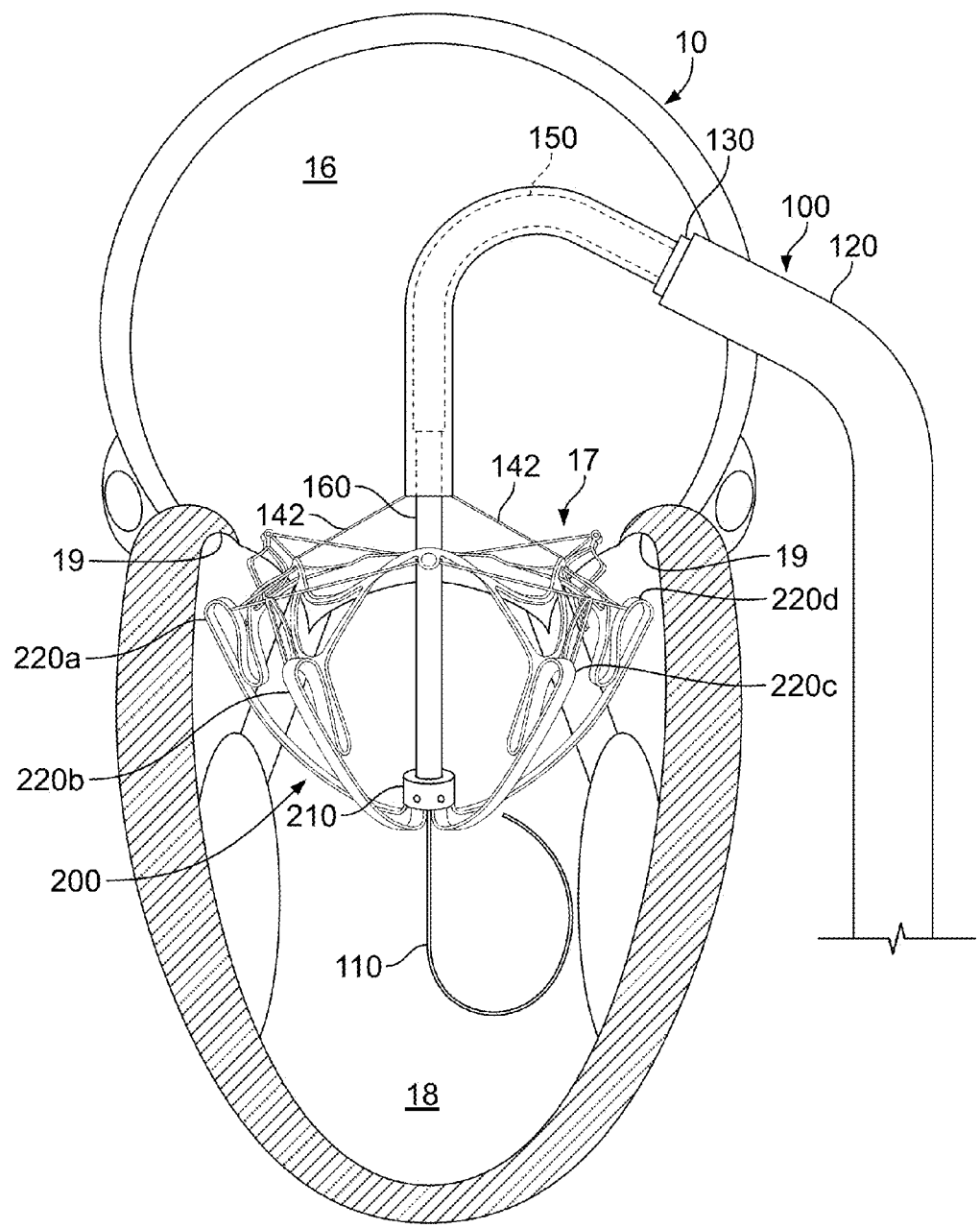
FIG. 5 shows a perspective view of the anchor assembly in a similar arrangement as shown in FIG. 4, but in a commissural cross-sectional view of the heart (from the left side of the heart).

Referring to FIG. 5, a commissural cross-sectional view of the heart 10 provides another perspective of the anchor assembly 200 in the same arrangement in relation to the native mitral valve 17 as shown in FIG. 4. This commissural cross-sectional view of the heart 10 is a cross-sectional view taken through the mitral valve 17 along a plane through the left atrium 16 and left ventricle 18 that is parallel to the line that intersects the two commissures of the mitral valve 17 (as described further in reference to FIG. 8 below). In the following FIGS. 5-7 and 13-17, the commissural cross-sectional view of the heart 10 will be used to describe the delivery system 100 and methods for deploying the prosthetic mitral valves provided herein. The view in FIGS. 5-7 and 13-17 is slightly tilted so that better visualization of the anchor assembly 200 is provided.

The anchor feet 220a, 220b, 220c, and 220d are positioned below the sub-annular gutter 19. In this position, the anchor feet 220a, 220b, 220c, and 220d are positioned under the systolic and diastolic excursions of the leaflets of the native mitral valve 17. In this orientation, the anchor feet 220a, 220b, 220c, and 220d can be aligned with the sub-annular gutter 19 in preparation for seating the anchor feet 220a, 220b, 220c, and 220d within the sub-annular gutter 19.

Figure 6:
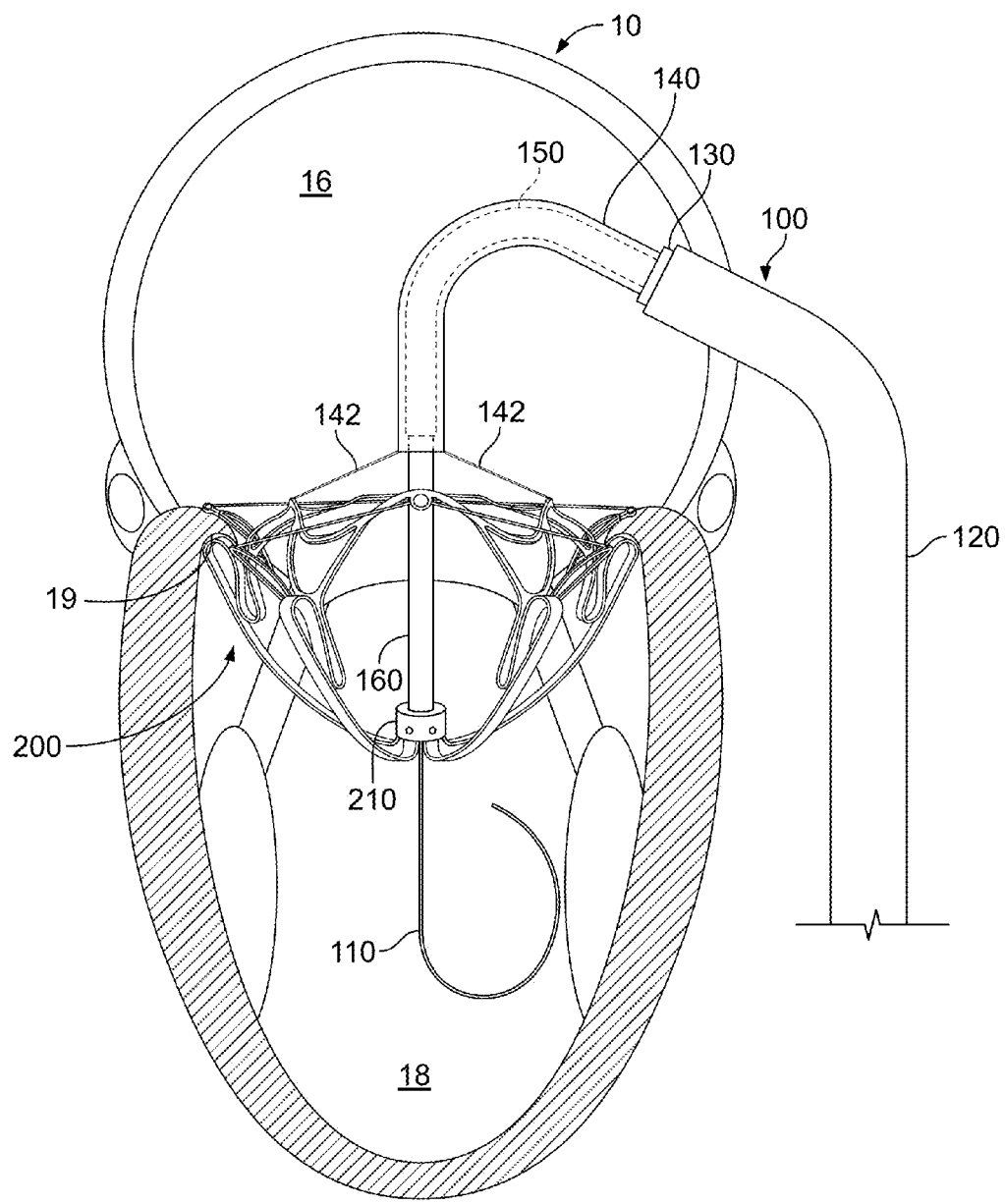
FIG. 6 shows a perspective view of the anchor assembly of FIG. 5 after being retracted so as to position the projections of the anchor assembly in the sub-annular gutter of the native mitral valve.

Referring to FIG. 6, the distal pusher 160 and the proximal control sheath 140 can be simultaneously refracted in relation to the secondary deflectable catheter 150 and the primary deflectable catheter 120. As a result, the anchor feet 220a, 220b, 220c, and 220d become seated in the sub-annular gutter 19. In this position, the anchor feet 220a, 220b, 220c, and 220d are positioned under the systolic and diastolic excursions of the leaflets of the native mitral valve 17, and the other structures of the anchor assembly 200 do not inhibit the movements of the leaflets. Therefore, with the anchor assembly 200 coupled to the structures of the mitral valve 17 as described, the mitral valve 17 can continue to function as it did before the placement of the anchor assembly 200. In addition, the manner in which the anchor assembly 200 interfaces with the native mitral valve 17 does not result in deformation of the native mitral valve 17. Therefore, the native mitral valve 17 can continue to function as it did before the placement of the anchor assembly 200.

Figure 7:
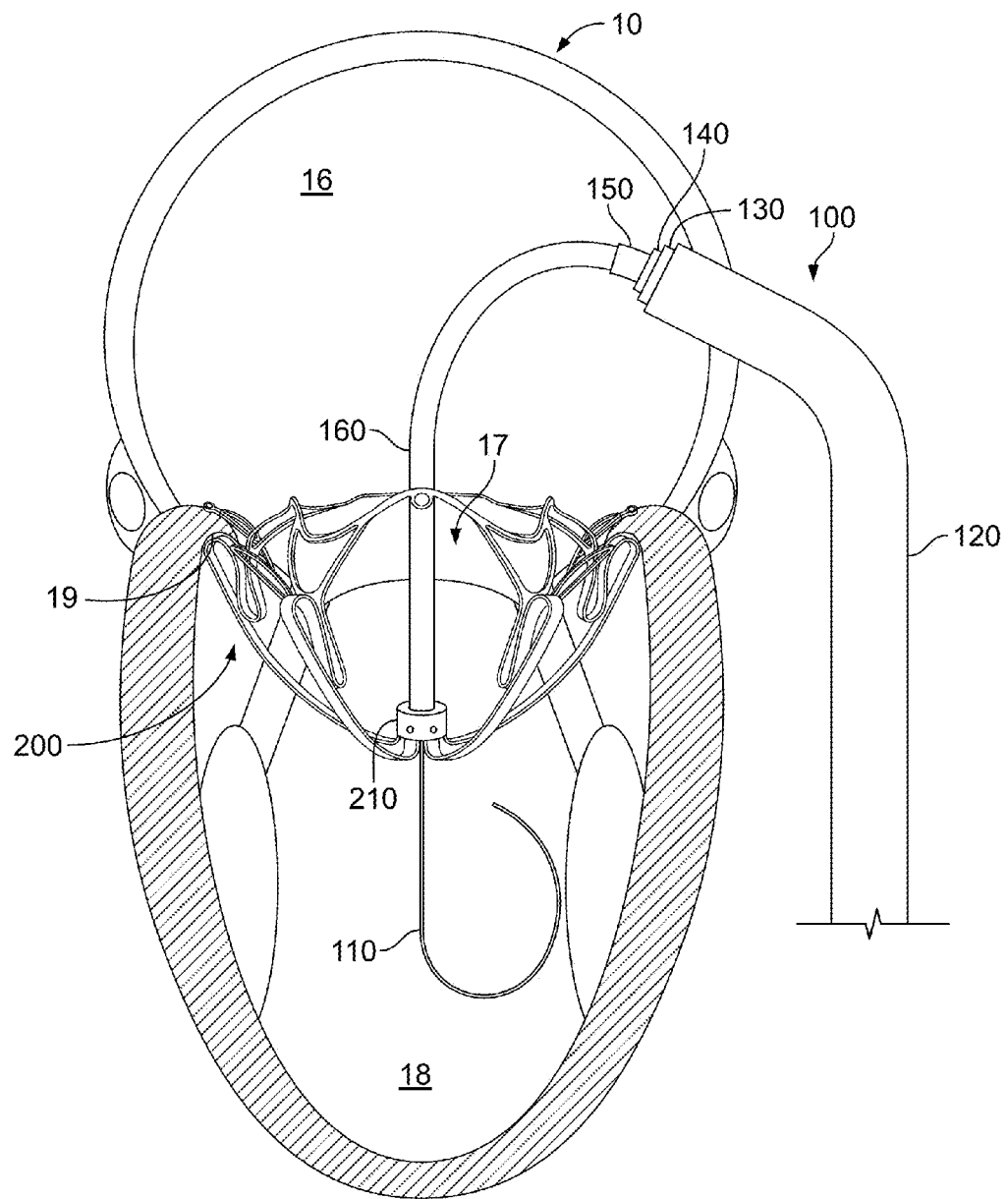
FIG. 7 shows a perspective view of the anchor assembly of FIG. 6 after the retraction of some members of the deployment system.

Referring to FIG. 7, with the anchor assembly 200 engaged within the native mitral valve 17, components of the delivery system 100 can be withdrawn from the anchor assembly 200. For example, the control wire 142 can be detached from the proximal end of the anchor assembly 200. Thereafter, the proximal control sheath 140 can be withdrawn. The secondary deflectable catheter 150 can also be withdrawn. In fact, if so desired, the proximal control sheath 140, the secondary deflectable catheter 150, and the anchor delivery sheath 130 can be completely withdrawn from the primary deflectable catheter 120. In contrast, in some implementations the distal pusher catheter 160 is advantageously left attached to the hub 210 of the anchor assembly 200. As will be described further below, in some implementations the distal pusher catheter 160 can be used as a rail on which a valve assembly is deployed into the interior of the anchor assembly 200. However, in some implementations the anchor assembly 200 is completely detached from the delivery system 100, and the delivery system 100 is removed from the patient. After a period of hours, days, weeks, or months, subsequent to the deployment of the anchor assembly 200, a valve assembly can be installed into the anchor assembly 200 to complete the installation of the prosthetic mitral valve.

Figure 8:
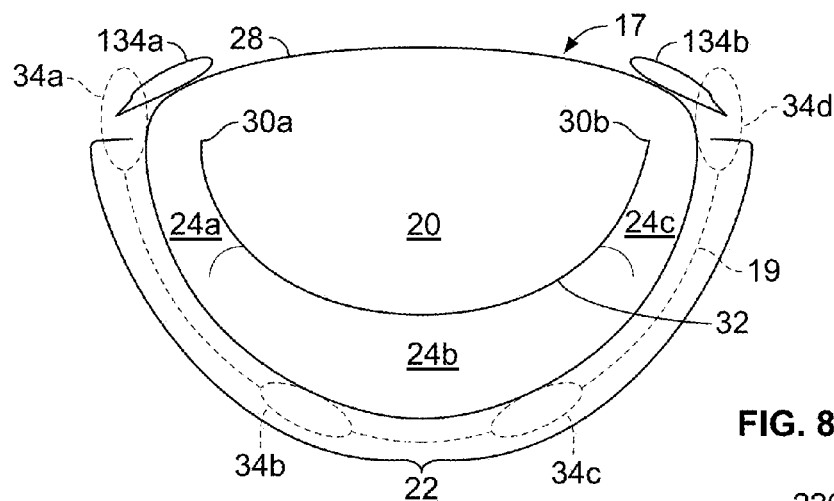
FIG. 8 is a top view of a native mitral valve and depicts a gutter perimeter of the sub-annular gutter of FIG. 7 (without the anchor assembly).
Figure 9:
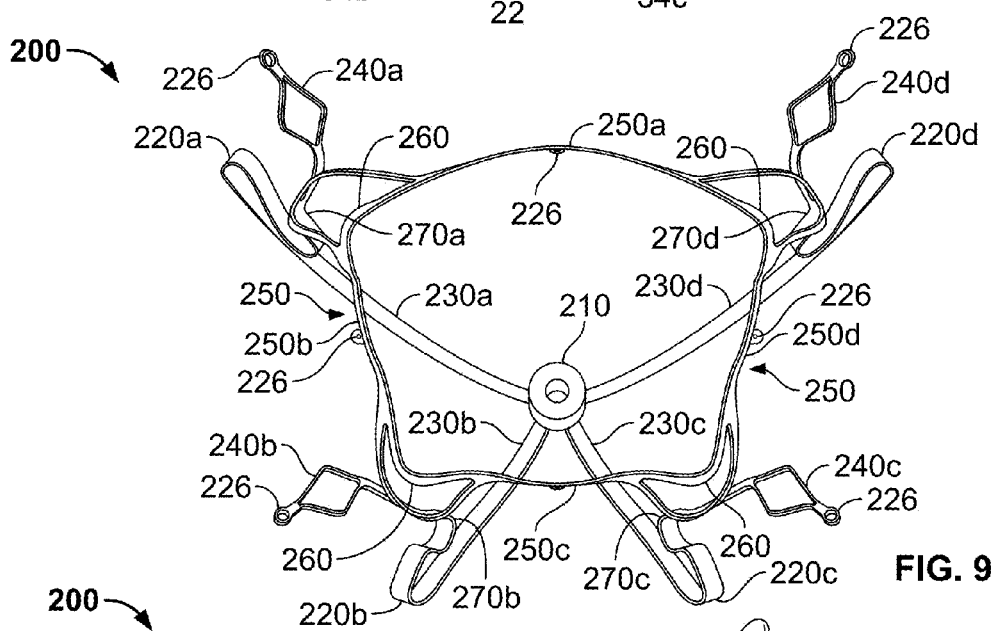
FIG. 9 shows a perspective top view of an example anchor assembly of FIGS. 2-6 in accordance with some embodiments.

Referring to FIGS. 8 and 9, the anatomy of the native mitral valve 17 includes some consistent and predictable structural features across patients that can be utilized for engaging the anchor assembly 200 therewith. For example, the native mitral valve 17 includes the aforementioned sub-annular gutter 19. In addition, the native mitral valve 17 includes a D-shaped annulus 28, an anterolateral commissure 30a, a posteromedial commissure 30b, a left fibrous trigone 134a, and a right fibrous trigone 134b. Further, the native mitral valve 17 includes an anterior leaflet 20 and a three-part posterior leaflet 22. The posterior leaflet 22 includes a lateral scallop 24a, a middle scallop 24b, and a medial scallop 24c. The free edges of the posterior leaflet 22 and the anterior leaflet 20 meet along a coaptation line 32.

The D-shaped annulus 28 defines the structure from which the anterior leaflet 20 and posterior leaflet 22 extend and articulate. The left and right fibrous trigones 134a and 134b are located near the left and right ends of the anterior leaflet 20 and generally adjacent the lateral and medial scallops 24a and 24c of the posterior leaflet 22. The sub-annular gutter 19 runs along the annulus 28 between the left and right fibrous trigones 134a and 134b along the posterior leaflet 22.

The regions at or near the high collagen annular trigones 134a and 134b can generally be relied upon to provide strong, stable anchoring locations. The muscle tissue in the regions at or near the trigones 134a and 134b also provides a good tissue ingrowth substrate for added stability and migration resistance of the anchor assembly 200. Therefore, the regions at or near the trigones 134a and 134b define a left anterior anchor zone 34a and a right anterior anchor zone 34b respectively. The left anterior anchor zone 34a and the right anterior anchor zone 34b provide advantageous target locations for placement of the left anterior foot 220a and the right anterior foot 220d respectively.

The depicted embodiment of the anchor assembly 200 also includes the left posterior foot 220b and the right posterior foot 220c. As previously described, the left posterior foot 220b and the right posterior foot 220c can also be advantageously positioned in the sub-annular gutter 19 in order to provide balanced and atraumatic coupling of the anchor assembly 200 to the native mitral valve 17. Therefore, a left posterior anchor zone 34b and a right anterior anchor zone 34c are defined in the sub-annular gutter 19. The left posterior anchor zone 34b and the right anterior anchor zone 34c can receive the left posterior foot 220b and the right posterior foot 220c respectively. In some implementations, the locations of the left posterior anchor zone 34b and the right anterior anchor zone 34c may vary from the depicted locations while still remaining within the sub-annular gutter 19. It should be understood that the depicted anchor assembly 200 is merely one non-limiting example of the anchor assemblies provided within the scope of this disclosure.

In some embodiments, the anchor assembly 200 includes supra-annular structures and sub-annular structures. For example, the sub-annular structures of the anchor assembly 200 include the aforementioned anchor feet 220a, 220b, 220c, and 220d, and the hub 210. In some embodiments, as described above, the hub 210 functions as a connection structure for the delivery system 100 (e.g., refer to FIG. 2). In addition, the hub 210 can function as a stabilizing structural component from which a left anterior sub-annular support arm 230a, a left posterior sub-annular support arm 230b, a right posterior sub-annular support arm 230c, and a right anterior sub-annular support arm 230d extend to the anchor feet 220a, 220b, 220c, and 220d respectively.

In some embodiments, such as the depicted embodiment, the supra-annular structures of the anchor assembly 200 include: a left anterior atrial holding feature 240a, a left posterior atrial holding feature 240b, a right posterior atrial holding feature 240c, and a right anterior atrial holding feature 240d; an anterior anchor arch 250a, a left anchor arch 250b, a posterior anchor arch 250c, and a right anchor arch 250d; and connection bridges 260. The anterior anchor arch 250a, left anchor arch 250b, posterior anchor arch 250c, and right anchor arch 250d are joined with each other to form an undulating supra-annular ring 250 that acts as a supra-annular structural element for the anchor assembly 200. As will be described further below, the supra-annular ring 250 also defines an opening to a space within the interior of the anchor assembly 200 that is configured to receive and engage with a valve assembly. The atrial holding features 240a, 240b, 240c, and 240d are configured to contact the shelf-like supra-annular tissue surface above the mitral valve annulus, and to thereby stabilize the anchor assembly 200 in supra-annular areas that are generally opposite of the anchor feet 220a, 220b, 220c, and 220d respectively.

In some embodiments, connection bridges 260 provide enhanced stability and fatigue resistance from vertically oriented forces on a companion artificial valve assembly when the valve (not shown) is closed and blocking pressurized blood during systole. The anchor assembly 200 can also include one or more holes 226 in frame portions adjacent the feet, which are additional control points for delivery and retrieval of the assembly, or could be used to secure a positional delivery frame.

In some embodiments, such as the depicted embodiment, the supra-annular structures and sub-annular structures of the anchor assembly 200 are interconnected by a lateral anterior inter-annular connection 270a, a lateral posterior inter-annular connection 270b, a medial posterior inter-annular connection 270c, and a medial anterior inter-annular connection 270d. For example, the lateral anterior inter-annular connection 270a connects the lateral anterior anchor foot 220a with the lateral anterior atrial holding feature 240a. In addition, the lateral anterior inter-annular connection 270a connects the lateral anterior anchor foot 220a with the anterior anchor arch 250a and the left anchor arch 250b. In the depicted embodiment, each of the other inter-annular connections 270b, 270c, and 270d interconnect portions of the supra-annular structures and sub-annular structures in manners analogous to that of the lateral anterior inter-annular connection 270a. For example, the lateral anterior inter-annular connection 270b connects the lateral anterior anchor foot 220b with the left anchor arch 250b and the posterior anchor arch 250c; the lateral anterior inter-annular connection 270c connects the lateral anterior anchor foot 220c with the posterior anchor arch 250c and the right anchor arch 250d; and the lateral anterior inter-annular connection 270d connects the lateral anterior anchor foot 220d with the right anchor arch 250d and the anterior anchor arch 250a.

In some embodiments, the elongate members of the anchor assembly 200 are formed from a single piece of precursor material (e.g., sheet or tube) that is cut, expanded, and connected to the hub 210. For example, some embodiments are fabricated from a tube that is laser-cut (or machined, chemically etched, water-jet cut, etc.) and then expanded and heat-set into its final expanded size and shape. In some embodiments, the anchor assembly 200 is created compositely from multiple elongate members (e.g., wires or cut members) that are joined together with the hub 210 and each other to form the anchor assembly 200.

The elongate members of the anchor assembly 200 can be comprised of various materials and combinations of materials. In some embodiments, nitinol (NiTi) is used as the material of the elongate members of the anchor assembly 200, but other materials such as stainless steel, L605 steel, polymers, MP35N steel, stainless steels, titanium, colbalt/chromium alloy, polymeric materials, Pyhnox, Elgiloy, or any other appropriate biocompatible material, and combinations thereof can be used. The super-elastic properties of NiTi make it a particularly good candidate material for the elongate members of the anchor assembly 200 because, for example, NiTi can be heat-set into a desired shape. That is, NiTi can be heat-set so that the anchor assembly 200 tends to self-expand into a desired shape when the anchor assembly 200 is unconstrained, such as when the anchor assembly 200 is deployed out from the anchor delivery sheath 130. A anchor assembly 200 made of NiTi, for example, may have a spring nature that allows the anchor assembly 200 to be elastically collapsed or "crushed" to a low-profile delivery configuration and then to reconfigure to the expanded configuration as shown in FIG. 9. The anchor assembly 200 may be generally conformable, fatigue resistant, and elastic such that the anchor assembly 200 can conform to the topography of the surrounding tissue when the anchor assembly 200 is deployed in a native mitral valve of a patient.

In some embodiments, the diameter or width/thickness of one or more of the elongate members forming the anchor assembly 200 may be within a range of about 0.008" to about 0.015" (about 0.20 mm to about 0.40 mm), or about 0.009" to about 0.030" (about 0.23 mm to about 0.76 mm), or about 0.01" to about 0.06" (about 0.25 mm to about 1.52 mm), or about 0.02" to about 0.10" (about 0.51 mm to about 2.54 mm), or about 0.06" to about 0.20" (about 1.52 mm to about 5.08 mm). In some embodiments, the elongate members forming the anchor assembly 200 may have smaller or larger diameters or widths/thicknesses. In some embodiments, each of the elongate members forming the anchor assembly 200 has essentially the same diameter or width/thickness. In some embodiments, one or more of the elongate members forming the anchor assembly 200 has a different diameter or width/thickness than one or more of the other elongate members of the anchor assembly 200. In some embodiments, one or more portions of one or more of the elongate members forming the anchor assembly 200 may be tapered, widened, narrowed, curved, radiused, wavy, spiraled, angled, and/or otherwise non-linear and/or not consistent along the entire length of the elongate members of the anchor assembly 200. Such features and techniques can also be incorporated with the valve assemblies of the prosthetic mitral valves provided herein.

In some embodiments, the elongate members forming the anchor assembly 200 may vary in diameter, thickness and/or width so as to facilitate variations in the forces that are exerted by the anchor assembly 200 in specific regions thereof, to increase or decrease the flexibility of the anchor assembly 200 in certain regions, to enhance migration resistance, and/or to control the process of compression (crushability) in preparation for deployment and the process of expansion during deployment of the anchor assembly 200.

In some embodiments, one or more of the elongate members of the elongate members forming the anchor assembly 200 may have a circular cross-section. In some embodiments, one or more of the elongate members forming the anchor assembly 200 may have a rectangular cross-sectional shape, or another cross-sectional shape that is not rectangular. Examples of cross-sectional shapes that the elongate members forming the anchor assembly 200 may have include circular, C-shaped, square, ovular, rectangular, elliptical, triangular, D-shaped, trapezoidal, including irregular cross-sectional shapes formed by a braided or stranded construct, and the like. In some embodiments, one or more of the elongate members forming the anchor assembly 200 may be essentially flat (i.e., such that the width to thickness ratio is about 2:1, about 3:1, about 4:1, about 5:1, or greater than about 5:1). In some examples, one or more of the elongate members forming the anchor assembly 200 may be formed using a center-less grind technique, such that the diameter of the elongate members varies along the length of the elongate members.

The anchor assembly 200 may include features that are directed to enhancing one or more desirable functional performance characteristics of the prosthetic mitral valve devices. For example, some features of the anchor assembly 200 may be directed to enhancing the conformability of the prosthetic mitral valve devices. Such features may facilitate improved performance of the prosthetic mitral valve devices by allowing the devices to conform to irregular tissue topographies and/or dynamically variable tissue topographies, for example. Such conformability characteristics can be advantageous for providing effective and durable performance of the prosthetic mitral valve devices. In some embodiments of the anchor assembly 200, some portions of the anchor assembly 200 are designed to be more conformable than other portions of the same anchor assembly 200. That is, the conformability of a single anchor assembly 200 can be designed to be different at various areas of the anchor assembly 200.

In some embodiments, the anchor assembly 200 includes features for enhanced in vivo radiographic visibility. In some embodiments, portions of the anchor assembly 200, such as one or more of the anchor feet 220a, 220b, 220c, and 220d, may have one or more radiopaque markers attached thereto. In some embodiments, some or all portions of the anchor assembly 200 are coated (e.g., sputter coated) with a radiopaque coating.

Still referring to FIGS. 8 and 9, as described above the anchor feet 220a, 220b, 220c, and 220d are sized and shaped to engage the sub-annular gutter 19 of the mitral valve 17. In some embodiments, the anterior feet 220a and 220d are spaced apart from each other by a distance in a range of about 30 mm to about 45 mm, or about 20 mm to about 35 mm, or about 40 mm to about 55 mm. In some embodiments, the posterior feet 220b and 220c are spaced apart from each other by a distance in a range of about 20 mm to about 30 mm, or about 10 mm to about 25 mm, or about 25 mm to about 40 mm.

In some embodiments, the anchor feet 220a, 220b, 220c, and 220d have a height ranging from about 8 mm to about 12 mm, or more than about 12 mm. In some embodiments, the anchor feet 220a, 220b, 220c, and 220d have a gutter engaging surface area (when fabric covered) ranging from about 6 mm$^2$ to about 24 mm$^2$. In some embodiments, the anchor feet 220a, 220b, 220c, and 220d each have essentially the same gutter engaging surface area. In particular embodiments, one or more of the anchor feet 220a, 220b, 220c, and 220d has a different gutter engaging surface area than one or more of the other anchor feet 220a, 220b, 220c, and 220d. The anchor feet 220a, 220b, 220c, and 220d can have widths ranging within about 1.5 mm to about 4.0 mm or more, and lengths ranging within about 3 mm to about 6 mm or more. The anchor feet 220a, 220b, 220c, and 220d are sized and shaped so that the anchor assembly 200 does not significantly impair the natural function of mitral valve chordae tendineae, the native mitral valve leaflets, and papillary muscles even after the anchor assembly is anchored at the mitral valve site.

As described previously, the anchor assembly 200 is designed to avoid interference with the functioning of the native mitral valve 17. Therefore, the anchor assembly 200 can be implanted within the native mitral valve 17 some time prior to the deployment therein of a replacement valve assembly, without degradation of valve 17 function during the period of time between the anchor implantation and the valve implantation (whether that time is on the order of minutes, or even several days or months). To avoid such interference between the anchor assembly 200 and the native mitral valve 17, the inter-annular connections 270a, 270b, 270c, and 270d pass through the coaptation line 32 approximately. More particularly, the left anterior inter-annular connection 270a passes through the coaptation line 32 adjacent to the anterolateral commissure 30a. In like manner, the right anterior inter-annular connection 270d passes through the coaptation line 32 adjacent to the posteromedial commissure 30b. In some implementations, the left posterior inter-annular connection 270b and right posterior inter-annular connection 270c pass through the native mitral valve 17 in locations that are posteriorly biased from the natural coaptation line 32. The posterior leaflet 22 will tend to compliantly wrap around the left posterior inter-annular connection 270b and right posterior inter-annular connection 270c to facilitate sealing of the mitral valve 17, with the anchor assembly 200 coupled thereto.

Figure 10:
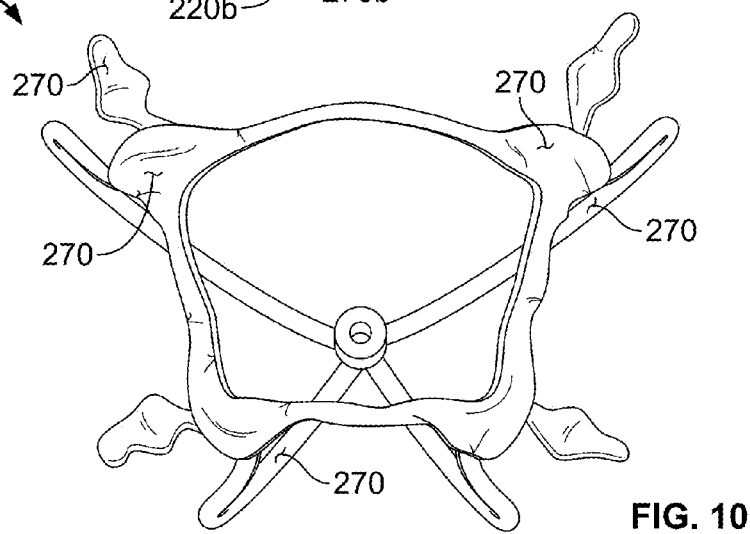
FIG. 10 shows a perspective view of the anchor assembly of FIG. 9 with a covering material disposed on portions of the anchor frame.

In reference to FIG. 10, in some embodiments the anchor assembly 200 includes a covering material 270 disposed on one or more portions of the anchor assembly 200. The covering material 270 can provide various benefits. For example, in some implementations the covering material 270 can facilitate tissue ingrowth and/or endothelialization, thereby enhancing the migration resistance of the anchor assembly 200 and preventing thrombus formation on blood contact elements. In another example, as described further below, the covering material 270 can be used to facilitate coupling between the anchor assembly 200 and a valve assembly that is received therein. The cover material 270 also prevents or minimizes abrasion and/or fretting between the anchor assembly 200 and valve assembly 300. The cover material 270 also prevents valve outer tissue abrasion related wear.

In the depicted embodiment, the covering material 270 is disposed essentially on the entire anchor assembly 200. In some embodiments, the covering material 270 is disposed on one or more portions of the anchor assembly 200, while one or more other portions of the anchor assembly 200 do not have the covering material 270 disposed thereon. While the depicted embodiment includes the covering material 270, the covering material 270 is not required in all embodiments. In some embodiments, two or more portions of covering material 270, which can be separated and/or distinct from each other, can be disposed on the anchor assembly 200. That is, in some embodiments a particular type of covering material 270 is disposed on some areas of the anchor assembly 200 and a different type of covering material 270 is disposed on other areas of the anchor assembly 200.

In some embodiments, the covering material 270, or portions thereof, comprises a fluoropolymer, such as an expanded polytetrafluoroethylene (ePTFE) polymer. In some embodiments, the covering material 270, or portions thereof, comprises a polyester, a silicone, a urethane, ELAST-EON™ (a silicone and urethane polymer), another biocompatible polymer, DACRON®, polyethylene terephthalate (PET), copolymers, or combinations and sub-combinations thereof. In some embodiments, the covering material 270 is manufactured using techniques such as, but not limited to, extrusion, expansion, heat-treating, sintering, knitting, braiding, weaving, chemically treating, and the like. In some embodiments, the covering material 270, or portions thereof, comprises a biological tissue. For example, in some embodiments the covering material 270 can include natural tissues such as, but not limited to, bovine, porcine, ovine, or equine pericardium. In some such embodiments, the tissues are chemically treated using glutaraldehyde, formaldehyde, or triglycidylamine (TGA) solutions, or other suitable tissue crosslinking agents.

In the depicted embodiment, the covering material 270 is disposed on the interior and the exterior of the anchor assembly 200. In some embodiments, the covering material 270 is disposed on the just the exterior of the anchor assembly 200. In some embodiments, the covering material 270 is disposed on the just the interior of the anchor assembly 200. In some embodiments, some portions of the anchor assembly 200 are covered by the covering material 270 in a different manner than other portions of the anchor assembly 200.

In some embodiments, the covering material 270 is attached to at least some portions of the anchor assembly 200 using an adhesive. In some embodiments, FEP (fluorinated ethylene propylene) is used as an adhesive to attach the covering material 270 to the anchor assembly 200, or portions thereof. For example, an FEP coating can be applied to some or all portions of the anchor assembly 200, and the FEP can act as a bonding agent to adhere the covering material 270 to the anchor assembly 200. In some embodiments, wrapping, stitching, lashing, banding, and/or clips, and the like can be used to attach the covering material 270 to the anchor assembly 200. In some embodiments, a combination of techniques are used to attach the covering material 270 to the anchor assembly 200.

In some embodiments, the covering material 270, or portions thereof, has a microporous structure that provides a tissue ingrowth scaffold for durable sealing and/or supplemental anchoring strength of the anchor assembly 200. In some embodiments, the covering material 270 is made of a membranous material that inhibits or reduces the passage of blood through the covering material 270. In some embodiments, the covering material 270, or portions thereof, has a material composition and/or configuration that inhibits or prevents tissue ingrowth and/or endothelialization to the covering material 270.

In some embodiments, the covering material 270 can be modified by one or more chemical or physical processes that enhance certain physical properties of the covering material 270. For example, a hydrophilic coating may be applied to the covering material 270 to improve the wettability and echo translucency of the covering material 270. In some embodiments, the covering material 270 may be modified with chemical moieties that promote or inhibit one or more of endothelial cell attachment, endothelial cell migration, endothelial cell proliferation, and resistance to thrombosis. In some embodiments, the covering material 270 may be modified with covalently attached heparin or impregnated with one or more drug substances that are released in situ.

In some embodiments, covering material 270 is preperforated to modulate fluid flow through the covering material 270 and/or to affect the propensity for tissue ingrowth to the covering material 270. In some embodiments, the covering material 270 is treated to make the covering material 270 stiffer or to add surface texture. For example, in some embodiments the covering material 270 is treated with FEP powder to provide a stiffened covering material 270 or roughened surface on the covering material 270. In some embodiments, selected portions of the covering material 270 are so treated, while other portions of the covering material 270 are not so treated. Other covering material 270 material treatment techniques can also be employed to provide beneficial mechanical properties and tissue response interactions. In some embodiments, portions of the covering material 270 have one or more radiopaque markers attached thereto to enhance in vivo radiographic visualization.

Figure 11A:
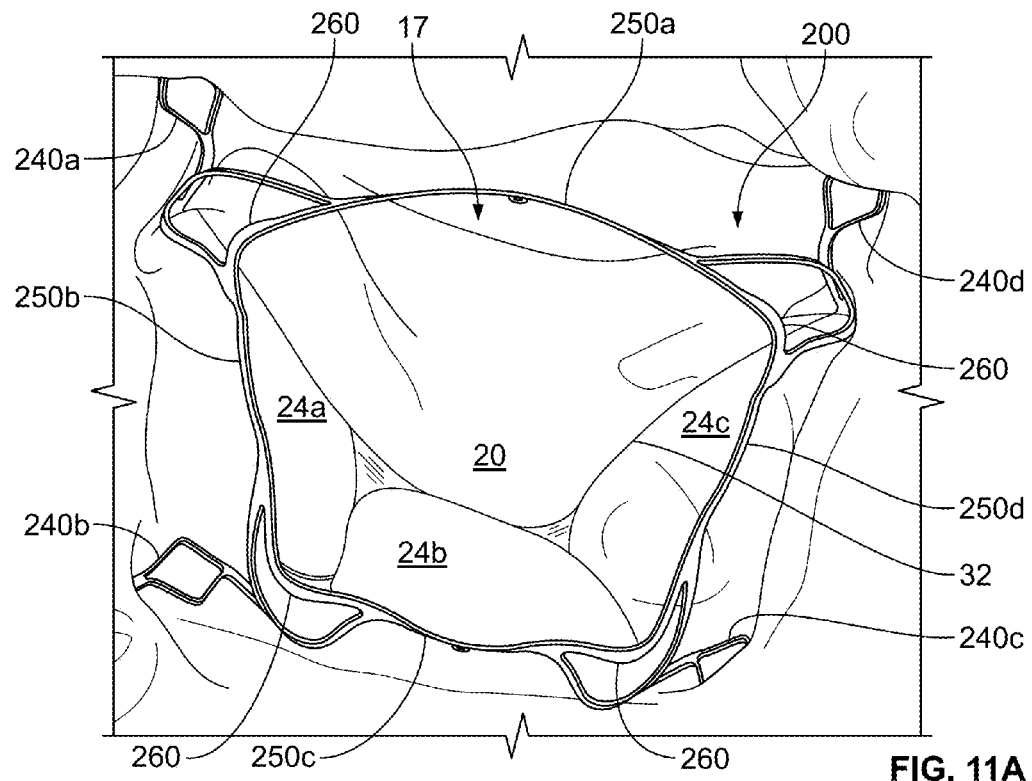
FIG. 11A shows a perspective top view of the anchor assembly of FIG. 9 implanted within a native mitral valve (with the native mitral valve leaflets in a closed state)
Figure 12A:
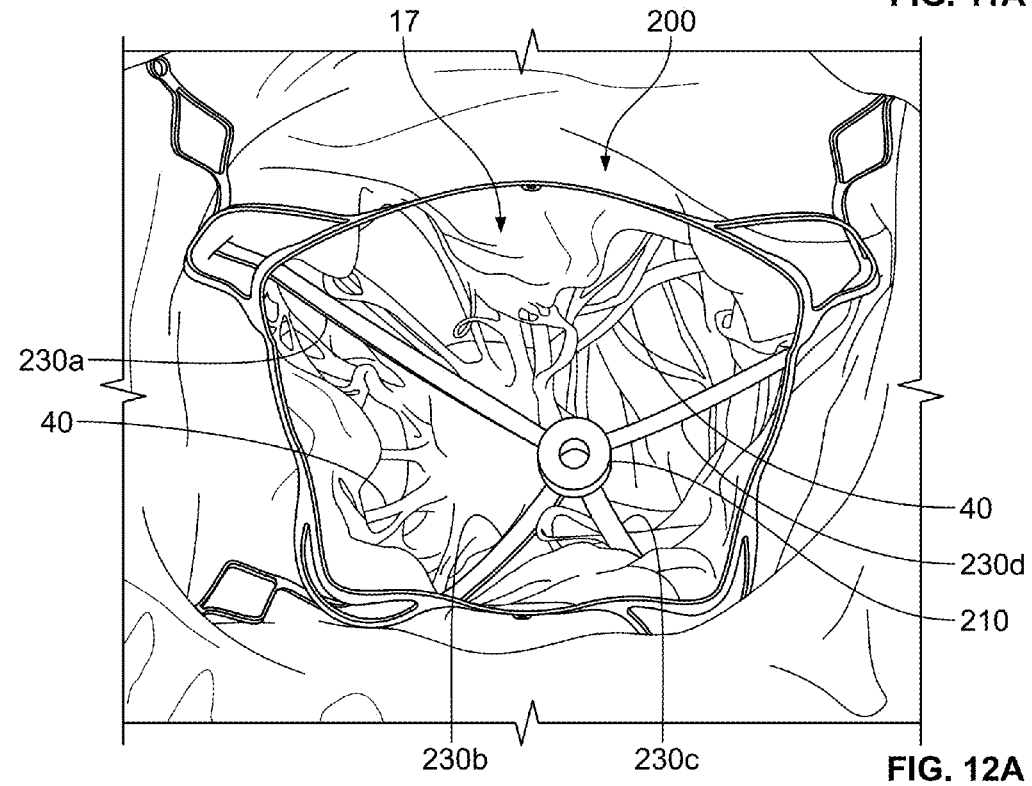
FIG. 12A shows a perspective top view of the anchor assembly of FIG. 9 implanted within the native mitral valve of FIG. 11A (with the native mitral valve leaflets in an open state)
Figure 12B:
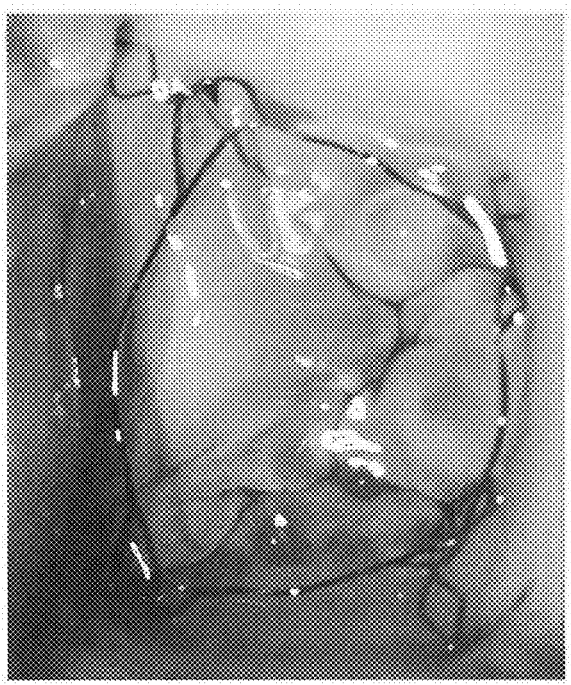
FIG. 12B shows a corresponding anatomical top view of the anchor assembly of FIG. 12A.
Figure 11B:
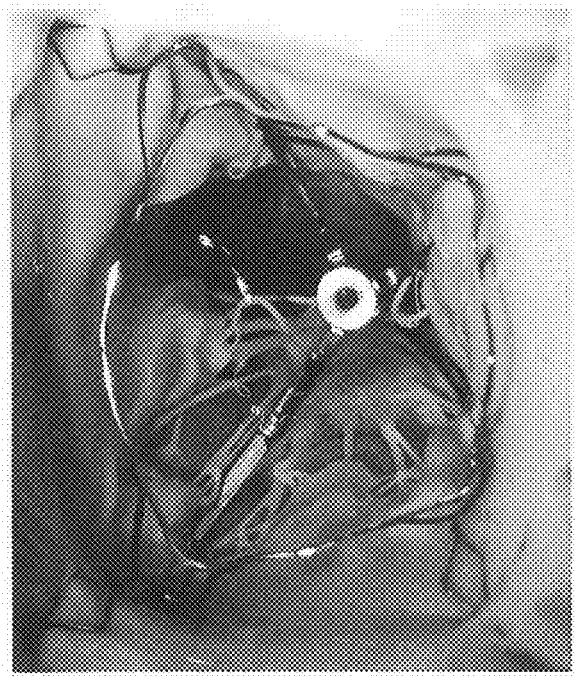
FIG. 11B shows a corresponding anatomical top view of the anchor assembly of FIG. 11A.

Referring now to FIGS. 11A and 12A, the anchor assembly 200 is shown implanted within a native mitral valve 17. FIGS. 11B and 12B are photographs that correspond to FIGS. 11A and 12A respectively. In FIG. 11A, the mitral valve 17 is shown in a closed state. In FIG. 12A, the mitral valve 17 is shown in an open state. These illustrations are from the perspective of the left atrium looking towards the mitral valve 17. For instance, in FIG. 12A chordae tendineae 40 are visible through the open leaflets of the mitral valve 17.

These figures illustrate the supra-annular structures and sub-annular structures of the anchor assembly 200 in their relationships with the native mitral valve 17. For example, the closed state of the native mitral valve 17 in FIG. 11A allows visibility of the supra-annular structures such as the left anterior atrial holding feature 240a, the left posterior atrial holding feature 240b, the right posterior atrial holding feature 240c, and the right anterior atrial holding feature 240d. In addition, the anterior anchor arch 250a, the left anchor arch 250b, the posterior anchor arch 250c, the right anchor arch 250d, and the connection bridges 260 are visible. However, the sub-annular structures are not visible in FIG. 11A because such structures are obstructed from view by the anterior leaflet 20 and the three-part posterior leaflet 24a, 24b, and 24c.

In contrast, in FIG. 12A certain sub-annular structures of the anchor assembly 200 are visible because the native mitral valve 17 is open. For example, sub-annular support arms 230a, 230b, 230c, and 230d and hub 210 are in view through the open mitral valve 17. Nevertheless, the anchor feet 220a, 220b, 220c, and 220d remain out of view because of their location within the sub-annular gutter of the mitral valve 17.

Figure 13:
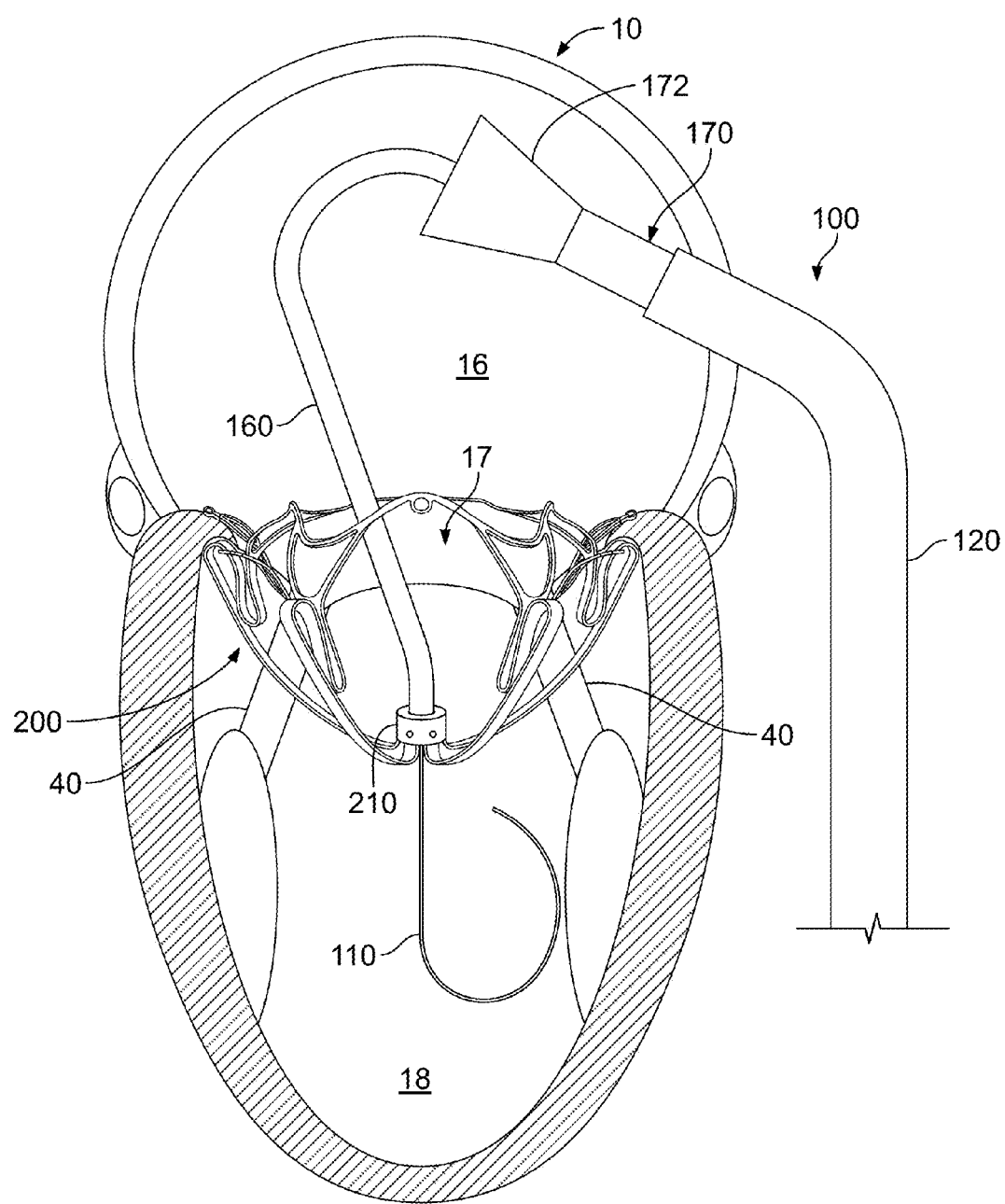
FIG. 13 shows a perspective view of the anchor assembly of FIG. 7 implanted within the native mitral valve and a valve assembly delivery sheath extending into the left atrium.

Referring to FIG. 13, after implantation of the anchor assembly 200 within the native mitral valve 17 (as performed, for example, in accordance with FIGS. 1-7 described above), a valve delivery sheath 170 of the delivery system 100 can be used to deploy a valve assembly within the anchor assembly 200. As described above in reference to FIG. 7, with the distal pusher catheter 160 coupled with the hub 210 of the anchor assembly 200, the distal pusher catheter 160 can be used to guide the valve assembly into the interior of the anchor assembly 200.

In some implementations, with the primary deflectable catheter 120 positioned with its distal end in the left atrium 16, the valve delivery sheath 170 is installed into a lumen of the primary deflectable catheter 120 (over the distal pusher catheter 160) and advanced through the primary deflectable catheter 120. As described further below, in some embodiments the valve delivery sheath 170 is preloaded with a prosthetic valve assembly and other components of the delivery system 100. The primary deflectable catheter 120 may be the same catheter that was used to deliver the anchor assembly 200, or it may be a different catheter (but still referred to here as the primary deflectable catheter 120 for simplicity sake).

In some embodiments, the valve delivery sheath 170 can be made from the materials described above in reference to the primary deflectable catheter 120. In some embodiments, the valve delivery sheath 170 has an outer diameter in the range of about 20 Fr to about 28 Fr (about 6.7 mm to about 9.3 mm). In some embodiments, the valve delivery sheath 170 has an outer diameter in the range of about 14 Fr to about 24 Fr (about 4.7 mm to about 8.0 mm).

In the depicted embodiment, the valve delivery sheath 170 includes a flared distal end portion 172. In some embodiments, no such flared distal end portion 172 is included. The flared distal end portion 172 can collapse to a lower profile when constrained within the primary deflectable catheter 120. When the flared distal end portion 172 is expressed from the primary deflectable catheter 120, the flared distal end portion 172 can self-expand to the flared shape. In some embodiments, the material of the flared distal end portion 172 includes pleats or folds, may be a continuous flared end or may be separated into sections such as flower pedals, and may include one or more resilient elements that bias the flared distal end portion 172 to assume the flared configuration in the absence of restraining forces (such as from containment within the primary deflectable catheter 120). The flared distal end portion 172 can be advantageous, for example, for recapturing the valve assembly within the lumen of the valve delivery sheath 170 after the valve assembly has been expressed from the flared distal end portion 172.

In some embodiments, the maximum outer diameter of the flared distal end portion 172 is in a range of about 30 Fr to about 34 Fr (about 10.0 mm to about 11.3 mm). In some embodiments, the maximum outer diameter of the flared distal end portion 172 is in a range of about 32 Fr to about 44 Fr (about 10.7 mm to about 14.7 mm). In some embodiments, the maximum outer diameter of the flared distal end portion 172 is in a range of about 24 Fr to about 30 Fr (about 8.0 mm to about 10.0 mm). In some embodiments, the maximum outer diameter of the flared distal end portion 172 is less than about 24 Fr (about 8.0 mm) or greater than about 44 Fr (about 14.7 mm).

Figure 14:
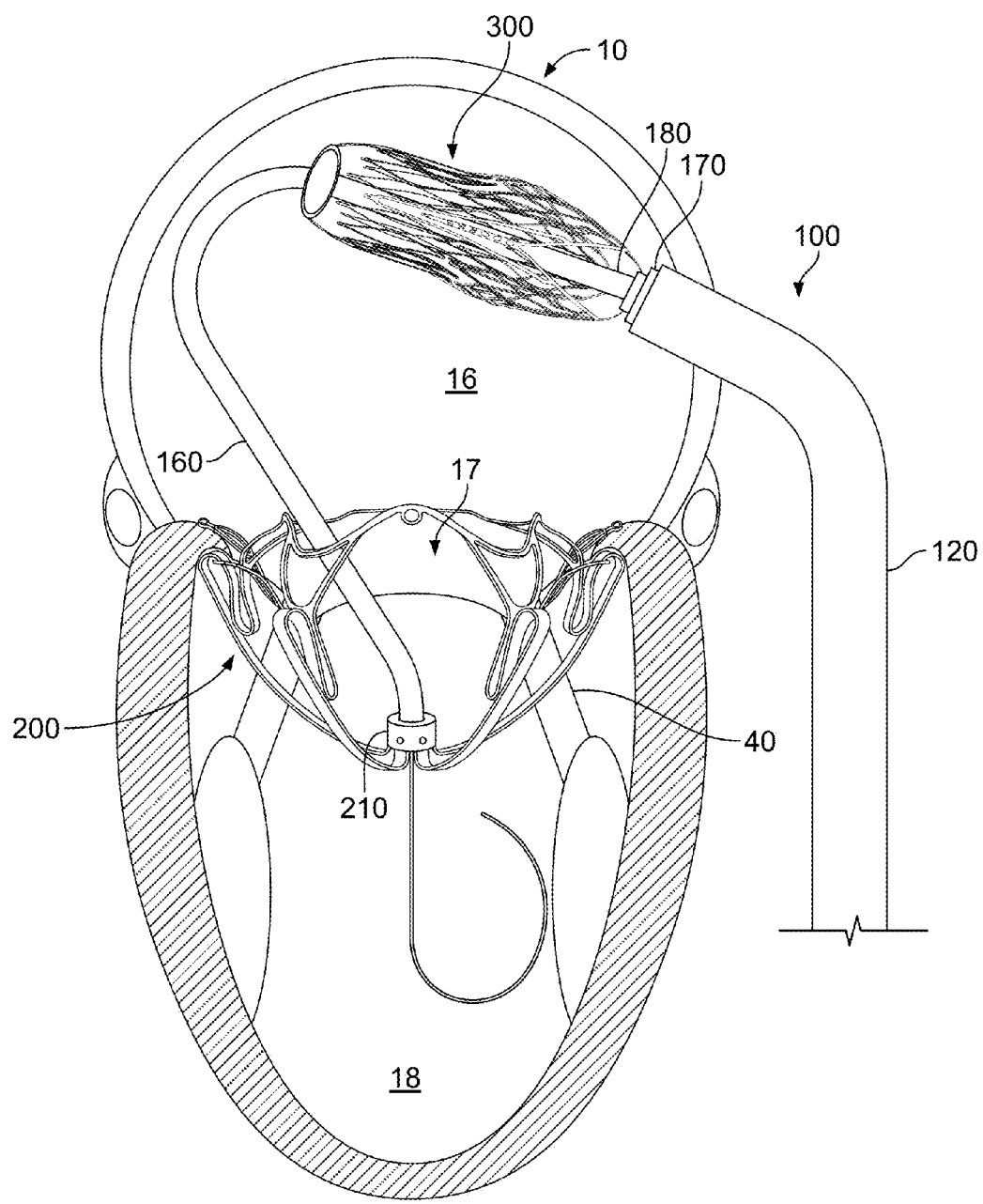
FIG. 14 shows a perspective view of a valve assembly in the left atrium after partial emergence from the valve assembly delivery sheath of FIG. 13. The valve assembly is configured in a first (partially expanded) arrangement.

Referring to FIG. 14, in some implementations the valve delivery sheath 170 can be withdrawn into the primary deflectable catheter 120 while a valve delivery catheter 180 is held substantially stationary to express a valve assembly 300 from a lumen of the valve delivery sheath 170. The valve delivery sheath 170 and the valve delivery catheter 180 are additional components in some embodiments of the example delivery system 100.

The valve assembly 300 can be releasably coupled to the valve delivery catheter 180 and retained in a low-profile configuration. In some embodiments, both the distal and proximal ends of the valve assembly 300 are releasably coupled to the valve delivery catheter 180. In some embodiments, just one of the distal end or the proximal end of the valve assembly 300 is releasably coupled to the valve delivery catheter 180. In particular embodiments, one or more control wires may be included to releasably couple one or more portions of the valve assembly 300 to the valve delivery catheter 180.

Referring to FIGS. 41-43, the valve assembly 300 is releasably coupled to the valve delivery catheter 180 via a proximal control wire 342a and a mid-body control wire 342b. The control wires 342a and 342b are threaded through one or more lumens within the valve delivery catheter 180. The control wires 342a and 342b exit the valve delivery catheter 180 and pass through eyelets on the proximal end and mid-body portions of the valve assembly 300 respectively. The control wires 342a and 342b are then threaded back into the valve delivery catheter 180. By manipulating the control wires 342a and 342b, a clinician operator can control the valve assembly 300. For example, the expansion and contraction of the valve assembly 300 can be controlled, and the detachment of the valve assembly 300 from the valve delivery catheter can be controlled, by manipulating the tension and position of the control wires 342a and 342b within the delivery catheter 180.

Referring again to FIG. 14, a lumen of the valve delivery catheter 180 can slidably surround the distal pusher catheter 160. Therefore, advancement of the valve delivery catheter 180 results in advancement of the valve assembly 300 over the distal pusher catheter 160 towards the anchor assembly 200.

Figure 15:
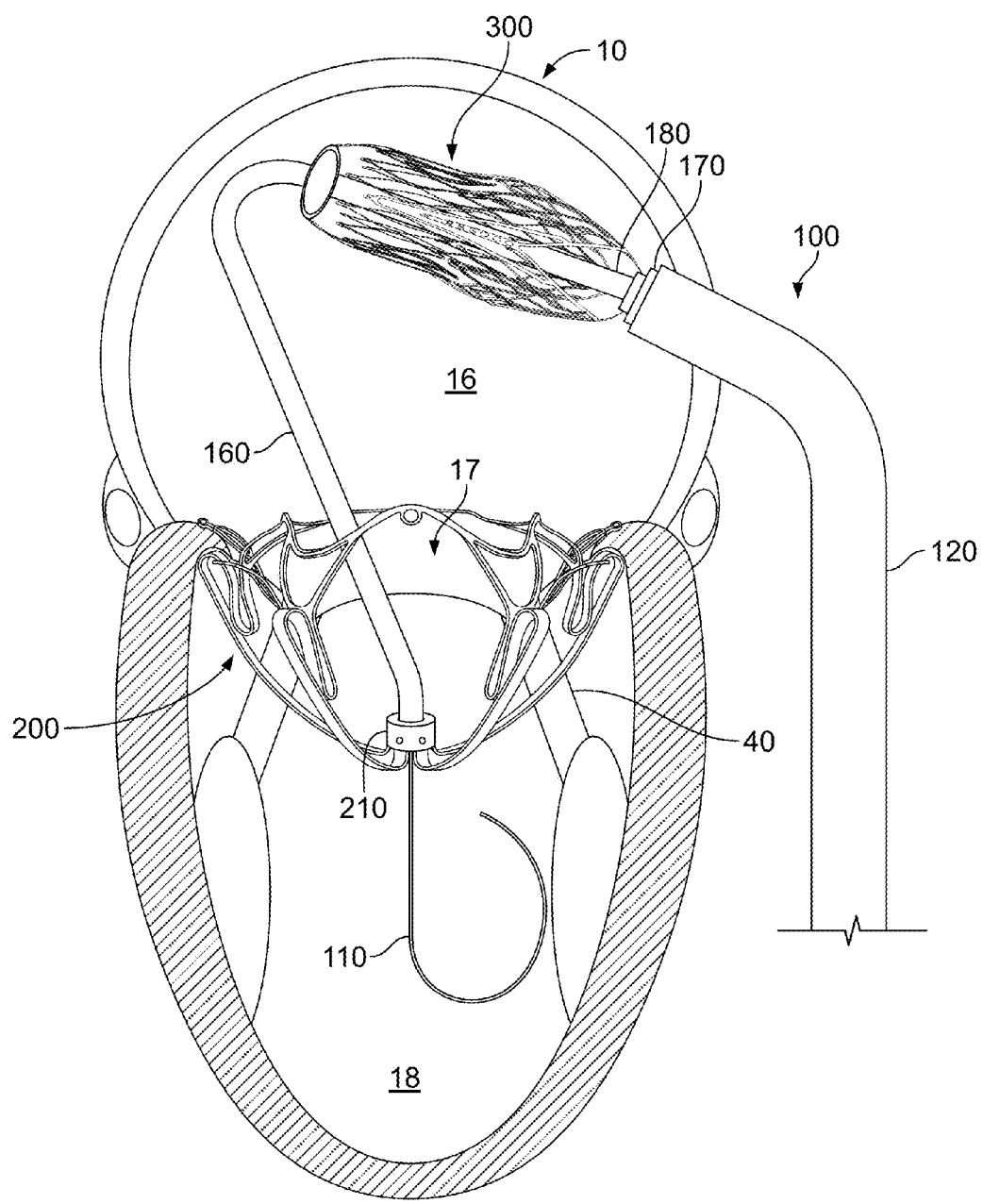
FIG. 15 shows a perspective view of the valve assembly of FIG. 14 with the valve deployment system being manipulated in preparation for the installation of the valve assembly into the anchor assembly.
Figure 16:
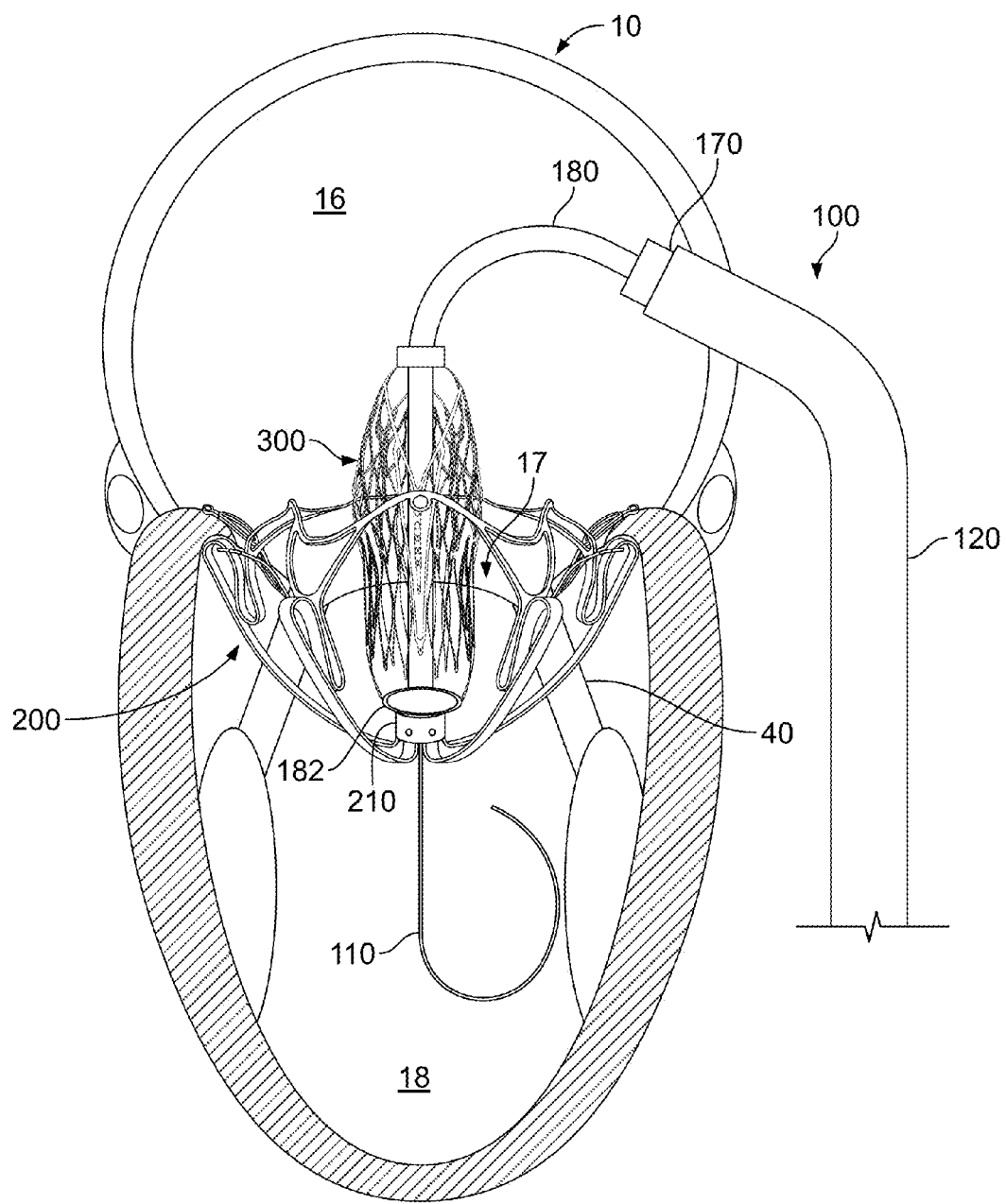
FIG. 16 shows a perspective view of the valve assembly of FIG. 15 (while still in the first (partially expanded) arrangement) being positioned within the anchor assembly.

Referring to FIGS. 15 and 16, the delivery system 100 can be manipulated by a clinician operator to perform a lateral pivot (panning, rotation, etc.) of the valve assembly 300 within the left atrium 16. The rotation of the valve assembly 300 changes the alignment of the valve assembly 300 from being generally axial with the distal end portion of the primary deflectable catheter 120 to being generally axial with the anchor assembly 200 (in preparation for installation of the valve assembly 300 into the interior of the anchor assembly 200).

In some implementations, the aforementioned rotation of the valve assembly 300 can be performed as follows. As shown in FIG. 15, because of the influence from the primary deflectable catheter 120 on the valve delivery catheter 180, the axis of the valve assembly 300 is initially in general alignment with the axis of the distal end portion of the primary deflectable catheter 120. From this arrangement, a simultaneous counter movement between the distal pusher catheter 160 and the valve delivery catheter 180 can be performed by the clinician to rotate the valve assembly 300. That is, as the distal pusher catheter 160 is pulled proximally, the valve delivery catheter 180 is pushed distally. As a result of that counter movement, the valve assembly 300 rotates in a relatively tight radius, as required by the confines of the left atrium 16. Thereafter, the valve delivery catheter 180 can be advanced further so that the valve assembly 300 is coaxially positioned within the interior of the anchor assembly 200 as shown in FIG. 16.

Figure 17:
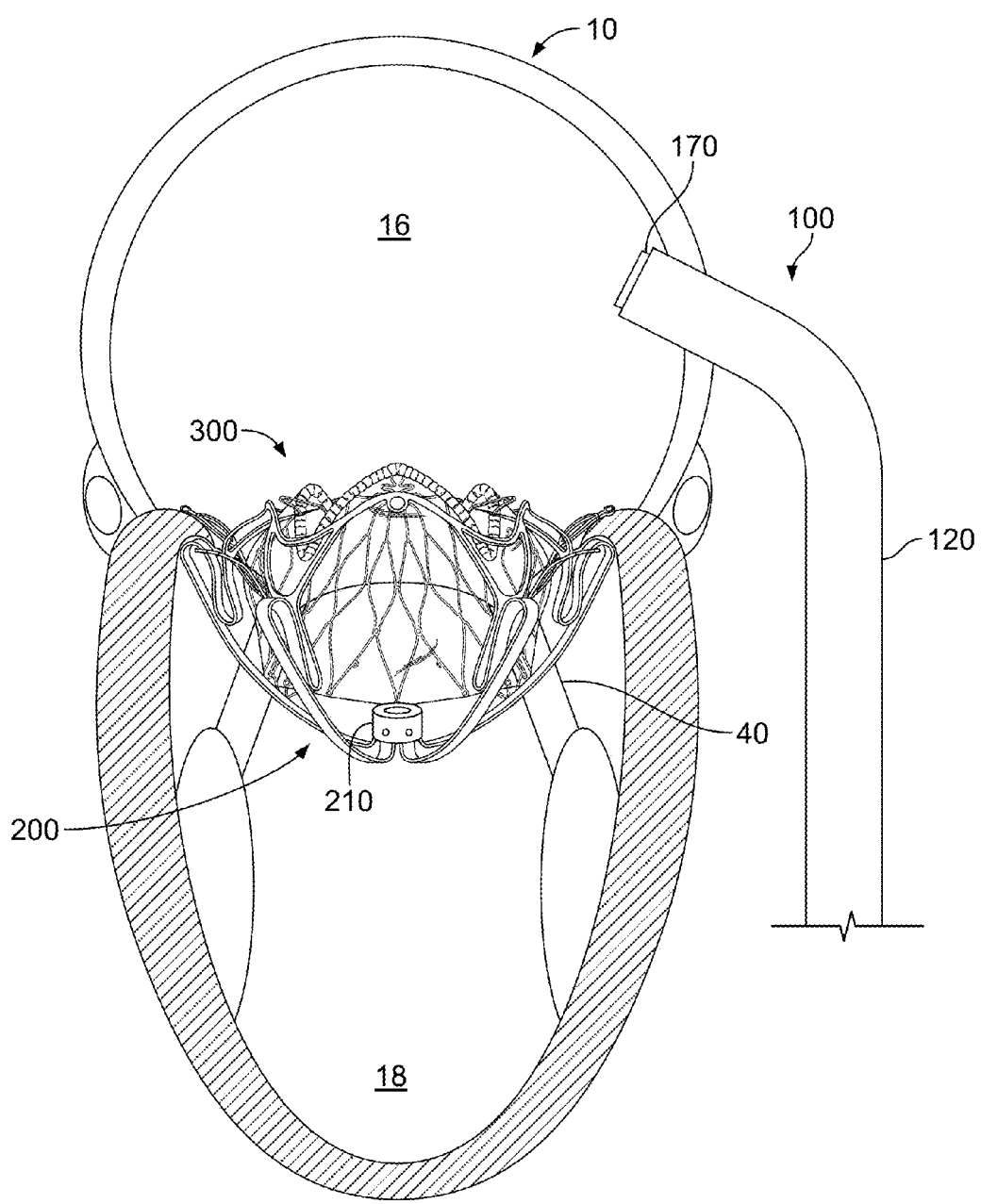
FIG. 17 shows a perspective view of the valve assembly of FIG. 16 the valve assembly expanded within the anchor assembly and detached from the deployment system.

Referring now also to FIG. 17, in some embodiments the valve assembly 300 and the anchor assembly 200 become aligned with each other coaxially, linearly (along their axes), and rotationally prior to or during the expansion of the valve assembly 300, resulting in engagement between the valve assembly 300 and the anchor assembly 200. Thereafter, the delivery system 100 can be withdrawn from the heart 10 and the prosthetic mitral valve can perform its function.

Coaxial alignment between the valve assembly 300 and the anchor assembly 200, as described above, is achieved by virtue of the valve delivery catheter 180 being slidably disposed over the distal pusher catheter 160. Linear alignment between the valve assembly 300 and the anchor assembly 200 can be achieved by the interaction of a distal end feature 182 of the valve delivery catheter 180 and the hub 210 of the anchor assembly 200. For example, in some embodiments an abutting of the distal end feature 182 and the hub 210 can result in proper linear alignment between the valve assembly 300 and the anchor assembly 200.

Relative rotational alignment between the valve assembly 300 and the anchor assembly 200 (about their axes) can be achieved in various manners. For example, in some embodiments the valve delivery catheter 180 is mechanically keyed to the distal pusher catheter 160 to slidably fix a desired rotational alignment between the valve assembly 300 and the anchor assembly 200. In some embodiments, other types of mechanical features (e.g., pins/holes, protrusions/receptacles, etc.) can be included to facilitate a desired rotational/spin alignment between the valve assembly 300 and the anchor assembly 200. Alternatively, or additionally, radiopaque markers can be included on the valve assembly 300 and on the anchor assembly 200 in locations and/or patterns that are indicative of the relative rotational orientation (about their axes) of the valve assembly 300 and the anchor assembly 200. In some embodiments, (e.g., when the valve delivery catheter 180 "torqueable") the valve delivery catheter 180 can be rotated about its axis until the markers are in proper position relative to the anchor assembly 200, prior to final expansion of valve assembly 300. Fluoroscopy can be used to attain a desired relative orientation of the radiopaque markers, and of the valve assembly 300 and the anchor assembly 200 correspondingly.

Figure 18:
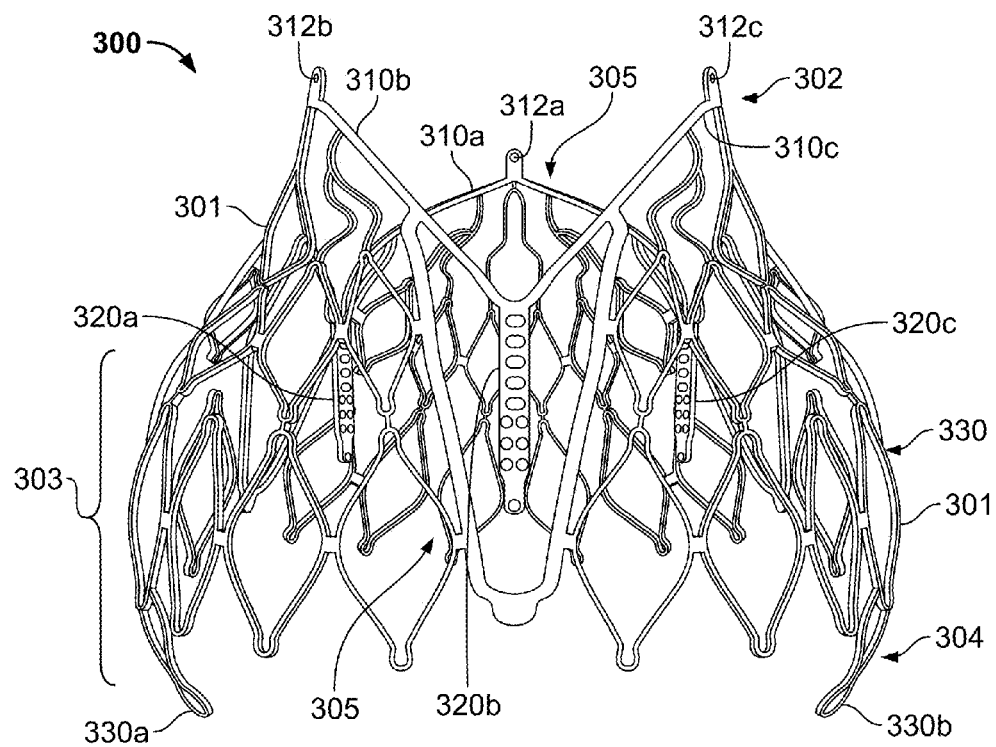
FIG. 18 shows an anterior side view of a valve frame of a valve assembly of FIG. 17, in accordance with some embodiments.
Figure 19:
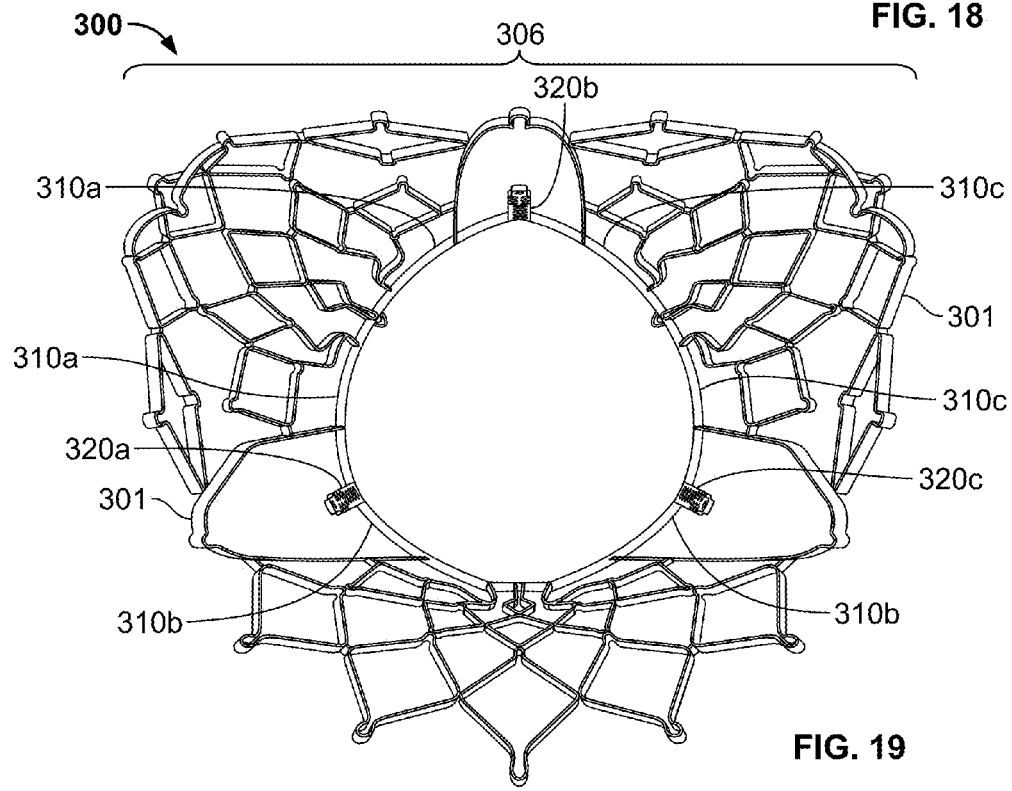
FIG. 19 shows a bottom view of the valve frame of FIG. 18.

Referring to FIGS. 18 and 19, an example valve assembly 300 is shown without any covering or valve/occluder leaflets. Hence, a valve assembly frame 301 of the valve assembly 300 is shown. FIG. 18 shows an anterior side view of the valve assembly frame 301, and FIG. 19 shows a bottom view of the valve assembly frame 301. The valve assembly 300 can be constructed using any of the various materials and manufacturing techniques described above in reference to the anchor frame 200 (e.g., refer to FIG. 9). It should be understood that the depicted valve assembly 300 is merely one non-limiting example of the valve assemblies provided within the scope of this disclosure.

The valve assembly 300 includes a proximal end portion 302 and a distal end portion 304. The valve assembly includes a flared external skirt portion 303 and defines an interior orifice portion 305. When the valve assembly 300 is implanted in a native mitral valve, the proximal end portion 302 is located supra-annular (in the left atrium) and the distal end portion 304 is located sub-annular (in the left ventricle). The proximal end portion 302 defines the generally circular entrance orifice of the valve assembly 300, as described further below.

In the depicted embodiment, the valve assembly 300 generally flares outward along a distal direction. Said differently, the distal end portion 304 is flared outward in comparison to the proximal end portion 302. Accordingly, the proximal end portion 302 defines a smaller outer profile in comparison to the distal end portion 304. However, some regions of the distal end portion 304 bow inwardly. In particular, for example, a posteromedial commissural corner 330a and anterolateral commissural corner 330b of the valve assembly 300 may bow inwardly. It should be understood that the outward flare of the distal end portion 304 in comparison to the proximal end portion 302 is merely one example configuration for a profile of the valve assembly 300. In some embodiments, for example, a shoulder (a portion of the valve assembly 300 having the largest outer periphery) is located proximal of the middle of the valve assembly 300.

The valve assembly 300 also includes an anterior side 306 between the posteromedial commissural corner 330a and anterolateral commissural corner 330b. When the valve assembly 300 is implanted in a native mitral valve, the anterior side 306 faces the anterior leaflet of the native mitral valve. The anterior side 306 of the distal end portion 304 defines a generally flat surface, whereas the other sides of the distal end portion 304 are rounded. Hence, the periphery of the distal end portion 304 is generally D-shaped. The D-shaped periphery of the distal end portion 304 provides the valve assembly 300 with an advantageous outer profile for interfacing and sealing with the native mitral valve. As described further below, sealing is attained by coaptation between the D-shaped periphery of the distal end portion 304 and the leaflets of the native mitral valve, and, in some embodiments, between the D-shaped periphery in the region of the skirt 303 with the native valve annulus.

In the depicted embodiment, the proximal end portion 302 of the valve assembly 300 includes three atrial leaflet arches 310a, 310b, and 310c that together define an undulating ring at the proximal end portion 302. Each of the leaflet arches 310a, 310b, and 310c includes an apex having an attachment hole 312a, 312b, and 312c respectively. In some embodiments, the attachment holes 312a, 312b, and 312c are used for coupling the proximal end of the valve assembly 300 to a delivery catheter (e.g., valve delivery catheter 180 of FIGS. 14-16).

The valve assembly 300 also includes three commissural posts 320a, 320b, and 320c that each extend distally from the intersections of the three leaflet arches 310a, 310b, and 310c. The commissural posts 320a, 320b, and 320c are disposed at about 120° apart from each other. The commissural posts 320a, 320b, and 320c each have a series of holes that can be used for attachment of leaflets, such as by suturing. The three leaflet arches 310a, 310b, and 310c and the three commissural posts 320a, 320b, and 320c are areas on the valve assembly 300 to which three prosthetic valve leaflets become attached to comprise a tri-leaflet occluder (e.g., refer to FIGS. 22-25).

As best seen in FIG. 19, the three leaflet arches 310a, 310b, and 310c and the commissural posts 320a, 320b, and 320c define a generally cylindrical frame for the tri-leaflet occluder construct. As such, the valve assembly 300 provides a proven and advantageous frame configuration for the tri-leaflet occluder. The tri-leaflet occluder provides open flow during diastole and occlusion of flow during systole.

Figure 20:
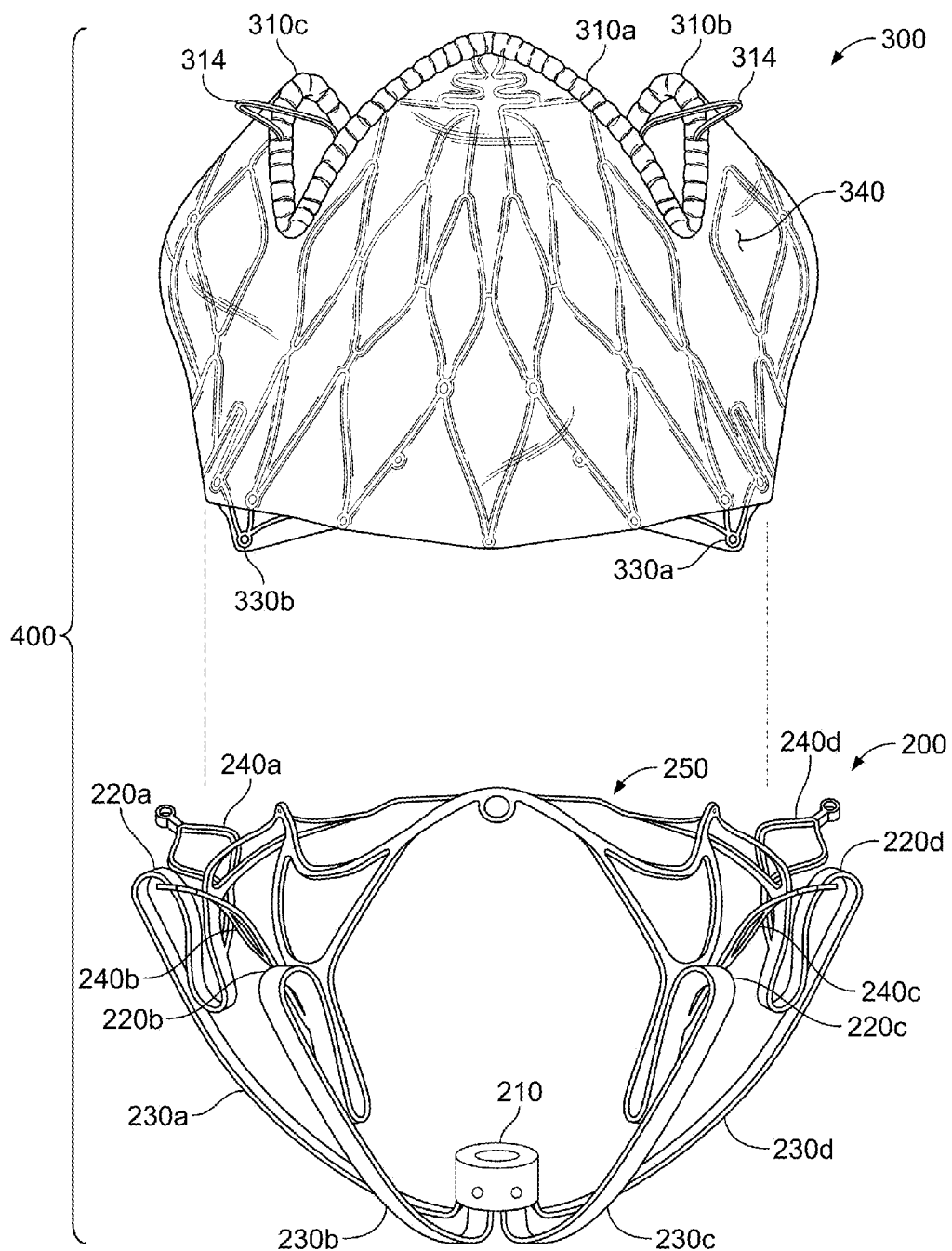
FIG. 20 is an exploded posterior side view of an anchor assembly and valve assembly of FIG. 17, in accordance with some embodiments.

Referring to FIG. 20, an exploded depiction of an example prosthetic mitral valve 400 includes an anchor assembly 200 and a valve assembly 300. This figures provides a posterior side view of the anchor assembly 200 and the valve assembly 300.

The valve assembly 300 includes a covering 340. The covering 340 can be made of any of the materials and constructed using any of the techniques described above in reference to covering 270. Additionally, in some embodiments the covering 340 can comprise natural tissues such as, but not limited to, bovine, porcine, ovine, or equine pericardium. In some such embodiments, the tissues are chemically cross-linked using glutaraldehyde, formaldehyde, or triglycidyl amine solution, or other suitable crosslinking agents.

When the valve assembly 300 and the anchor assembly 200 are coupled together, the valve assembly 300 is geometrically interlocked within the interior of the anchor assembly 200 (e.g., in some embodiments by virtue of the tapered shape of the valve assembly 300 within the supra-annular ring and interior space of the anchor assembly 200). In particular, in some embodiments the valve assembly 300 is contained within the interior space between the supra-annular ring 250 and the sub-annular support arms 230a, 230b, 230c, and 230d. As described above, the interlocked arrangement between the valve assembly 300 and the anchor assembly 200 is accomplished by positioning a valve assembly 300 in a low-profile configuration within the interior of the anchor assembly 200 and then allowing expansion of the valve assembly 300 within the interior of the anchor assembly 200 (e.g., refer to FIGS. 16 and 17).

Figure 21:
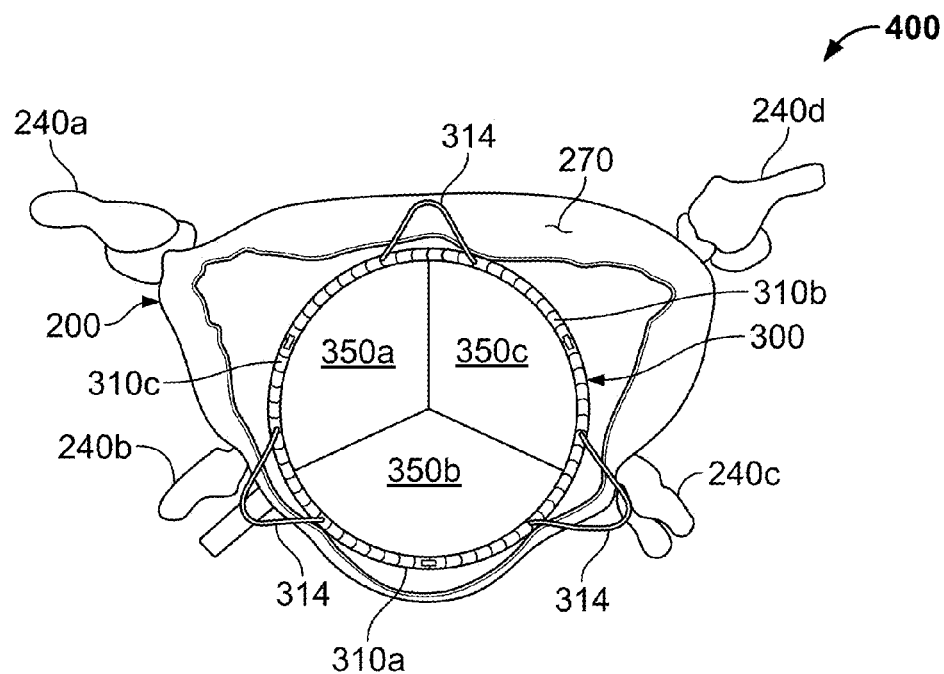
FIG. 21 is a top view of an example prosthetic mitral valve system that includes a valve assembly engaged with an anchor assembly, in accordance with some embodiments.
Figure 22:
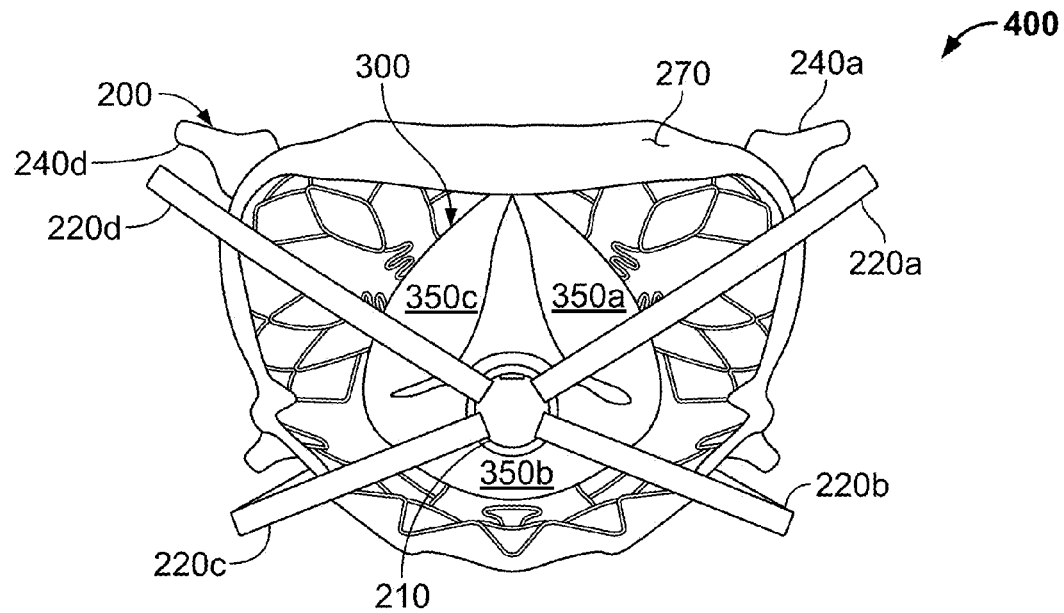
FIG. 22 is a bottom view of the example prosthetic mitral valve system of FIG. 21.

Referring to FIGS. 21 and 22, a deployed configuration of the example prosthetic mitral valve 400 includes the valve assembly 300 engaged within the anchor assembly 200. FIG. 21 shows a top (atrial) view of the prosthetic mitral valve 400, and FIG. 22 shows a bottom (ventricle) view of the prosthetic mitral valve 400.

In some embodiments, such as the depicted embodiment, valve assembly 300 includes three leaflets 350a, 350b, and 350c that perform the occluding function of the prosthetic mitral valve 400. The cusps of the three leaflets 350a, 350b, and 350c are fixed to the three atrial leaflet arches 310a, 310b, and 310c, and to the three commissural posts 320a, 320b, and 320c (refer to FIGS. 18 and 19). The free edges of the three leaflets 350a, 350b, and 350c can seal by coaptation with each other during systole and open during diastole.

The three leaflets 350a, 350b, and 350c can be comprised of natural or synthetic materials. For example, the three leaflets 350a, 350b, and 350c can be comprised of any of the materials described above in reference to the covering 340, including the natural tissues such as, but not limited to, bovine, porcine, ovine, or equine pericardium. In some such embodiments, the tissues are chemically cross-linked using glutaraldehyde, formaldehyde, or triglycidyl amine solution, or other suitable crosslinking agents. In some embodiments, the leaflets 350a, 350b, and 350c have a thickness in a range of about 0.005" to about 0.020" (about 0.13 mm to about 0.51 mm), or about 0.008" to about 0.012" (about 0.20 mm to about 0.31 mm). In some embodiments, the leaflets 350a, 350b, and 350c have a thickness that is less than about 0.005" (about 0.13 mm) or greater than about 0.020" (about 0.51 mm).

In some embodiments, the occluding function of the prosthetic mitral valve 400 can be performed using configurations other than a tri-leaflet occluder. For example, bi-leaflet, quad-leaflet, or mechanical valve constructs can be used in some embodiments.

Figure 23:
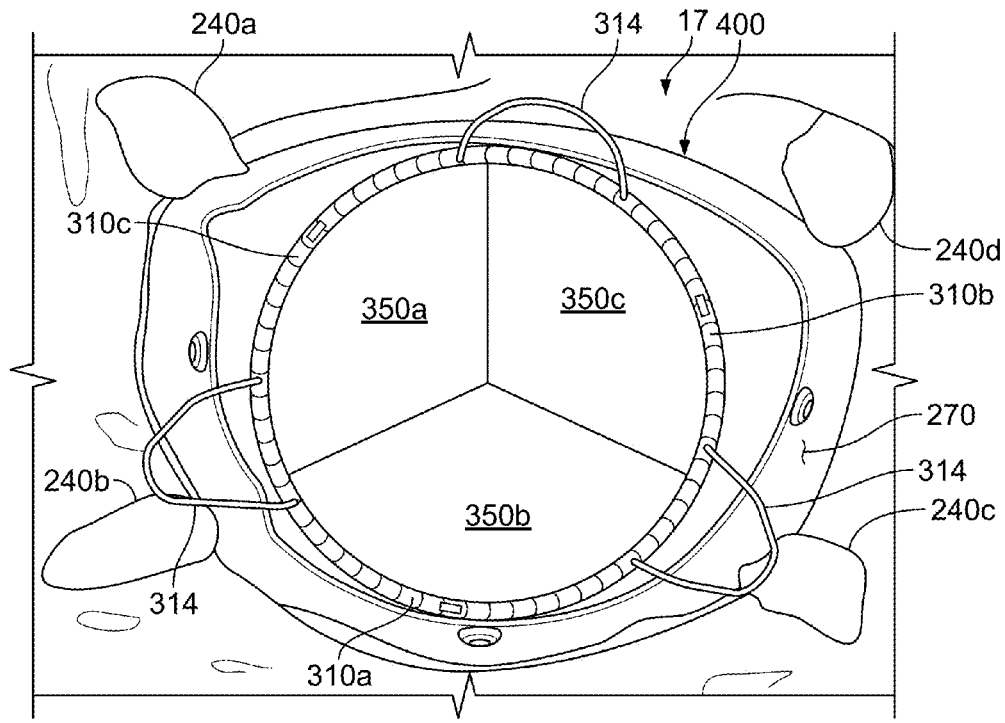
FIG. 23 shows a top view of the prosthetic mitral valve system of FIG. 21 implanted within a native mitral valve. The occluder portion of prosthetic mitral valve system is shown in a closed state.
Figure 24:
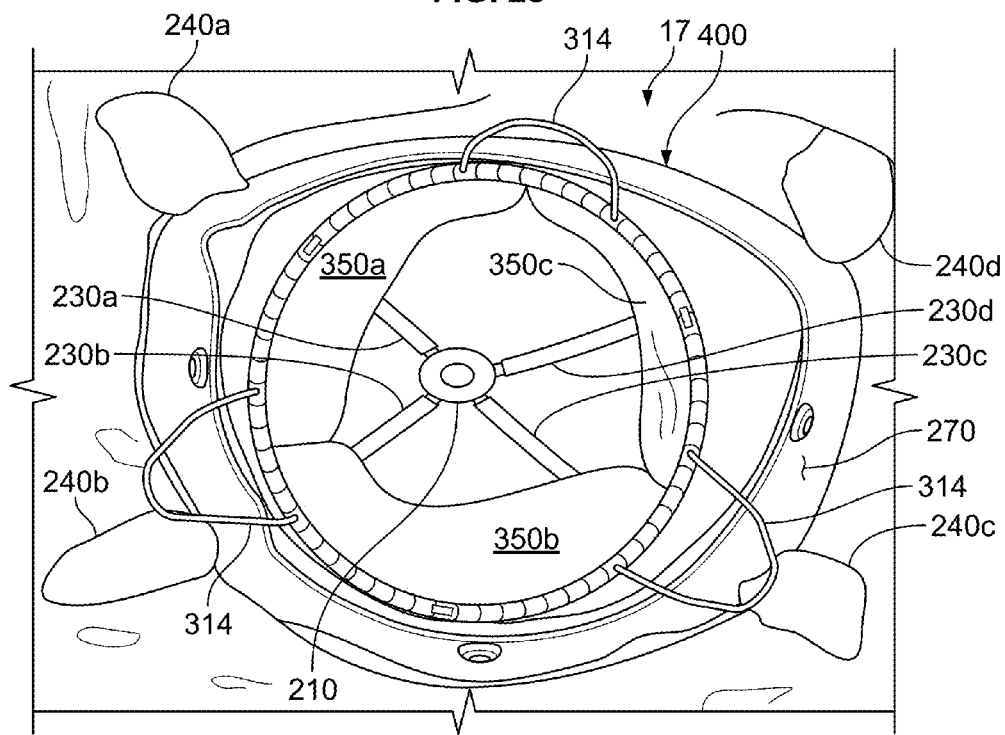
FIG. 24 shows a top view of the prosthetic mitral valve system of FIG. 21 implanted within a native mitral valve. The occluder portion of the prosthetic mitral valve system is shown in an open state.

Referring to FIGS. 23 and 24, the prosthetic mitral valve 400 is shown implanted within a native mitral valve 17. In FIG. 23, the prosthetic mitral valve 400 is shown in a closed state (occluded). In FIG. 24, the prosthetic mitral valve 400 is shown in an open state. These illustrations are from the perspective of the left atrium looking towards the mitral valve 17. For instance, in FIG. 24 the hub 210 and the sub-annular support arms 230a, 230b, 230c, and 230d of the anchor assembly 200 is visible through the open leaflets 350a, 350b, and 350c of the prosthetic mitral valve 400, whereas in FIG. 23 the hub 210 and the sub-annular support arms 230a, 230b, 230c, and 230d are not visible because the closed leaflets 350a, 350b, and 350c block the hub 210 from view.

FIGS. 25-33 describe additional aspects pertaining to sealing between native mitral valve structures and the implantable prosthetic mitral valves described herein. During systole, ventricle-to-atrium sealing is relevant in order to effectively treat MR via implantation of a prosthetic mitral valve. In addition, during diastole, atrium-to-ventricle sealing between native mitral valve structures and the prosthetic mitral valves described herein is relevant for preventing or reducing paravalvular leakage, and for good healing and chronic stability. The prosthetic mitral valves described herein are designed to have various features that provide for effective sealing with the native mitral valve structures.

One feature that enhances the sealing of the prosthetic mitral valves provided herein pertains to the shape of the prosthetic valve framework in relation to the shape of the native mitral valve. As described above, the annulus of a native mitral valve is generally D-shaped (e.g., refer to FIG. 8). In addition, as described above, the distal end portions of the prosthetic mitral valves described herein are D-shaped (e.g., refer to FIG. 19). In other words, the portion of the prosthetic valve that is designed to interface with the native valve annulus has a D-shaped profile that is similar to the shape of the annulus. This similarity of shapes can provide particular sealing efficacy in the areas of the lateral scallop 24a and the medial scallop 24c of the posterior leaflets 22 (refer to FIG. 8).

Another feature that enhances the sealing of the prosthetic mitral valves provided herein pertains to the size of the selected prosthetic valve in relation to the size of the native mitral valve, especially during systole. In some implementations, a selected prosthetic valve will intentionally have an outer profile (when unconstrained) that is equal to or slightly larger than the size of the annulus of the native mitral valve. That is, in the area on the valve surface that is intended to be adjacent to the native valve annulus, the size of the valve may result in a line-to-line fit or a slight interference fit with the native valve annulus. Hence, in some implementations the atrium-to-ventricle sealing during diastole is provided by the line-to-line fit or slight interference fit between the valve and the native valve annulus.

Another feature that enhances the sealing of the prosthetic mitral valves provided herein pertains to the relative geometric orientation of sealing surfaces on the prosthetic valve in relation to the annulus of the native mitral valve. While in some implementations, some sealing is provided by the mechanical fit between the outer profile of the valve and the receiving structure of the native mitral valve, in some implementations substantial sealing is provided by coaptation between the native leaflets and sealing surfaces on the perimeter of the prosthetic valve (to thereby create a contact seal during diastole and a left ventricle pressurized seal during systole). This type of sealing may be referred to herein as a leaflet to valve body seal. As described further below, the prosthetic mitral valves provided herein have sealing surfaces that are geometrically oriented in relation to the native valve annulus so that a leaflet to valve body seal is provided. While the leaflet to valve body seal is not entirely a mechanically compressive type of seal or an attachment onto the native tissue (active fixation) type of seal, in some embodiments such mechanical or attachment type of seals may alternatively or additionally be incorporated.

In some implementations, an effective leaflet to valve body seal (not based entirely on compression or attachment) may necessitate some native leaflet movement to the sealing surface of the valve body. Hence, a valve body shape that mimics the shape of the native mitral valve is advantageous. As described above, in some embodiments the outer periphery of the valve assemblies provided herein have a D-shaped periphery that generally correlates with the D-shaped annulus of native mitral valves. Accordingly, the movement distance of the native valve leaflets to the sealing surface of the valve body can be minimized (or essentially eliminated in some implementations), and sealing can thereby be enhanced.

In addition, an effective leaflet to valve body seal exhibits contiguous coaptation between the native leaflets and prosthetic valve body around the entire periphery of the prosthetic valve body. As described further below, the profiles of the prosthetic mitral valves provided herein are designed to interface with the native leaflets so as to provide contiguous coaptation around the entire periphery of the prosthetic valve. To accomplish this, in some embodiments the profile of some regions of the prosthetic mitral valves are different than the profile of other regions of the same valve (e.g., in correspondence with differing anatomical features in various portions of the native mitral valve).

Figure 25:
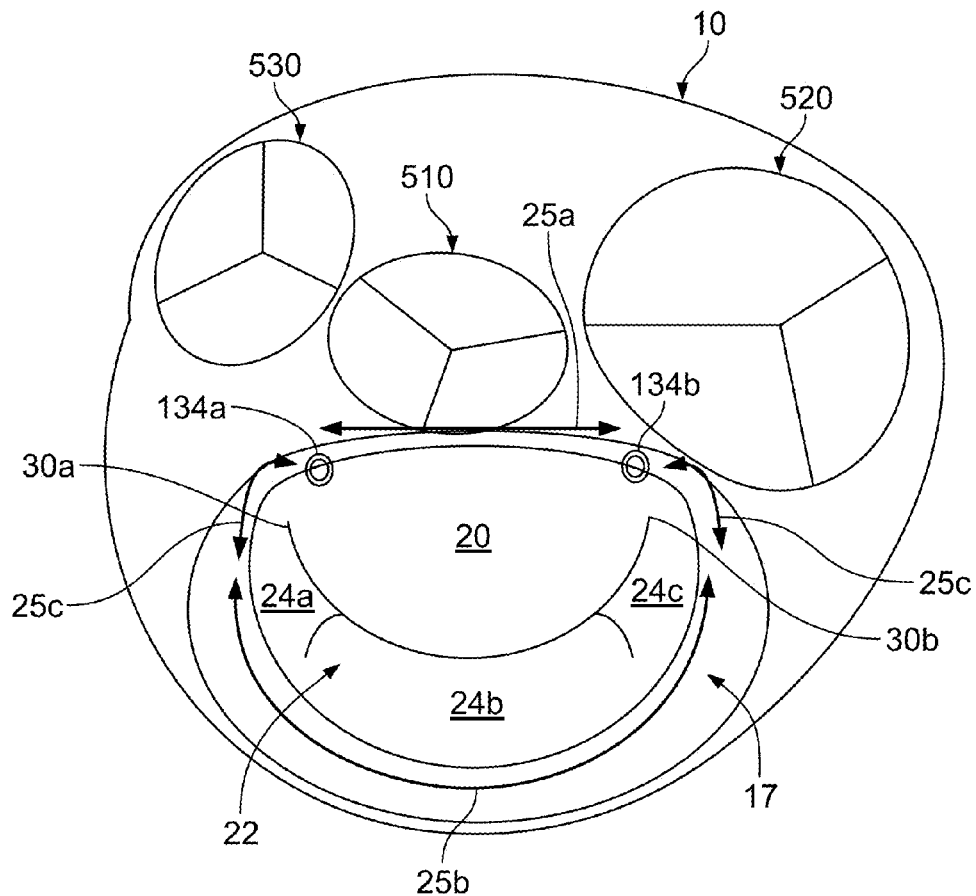
FIG. 25 is a lateral cross-sectional top view of a heart showing the mitral, aortic, tricuspid and pulmonary valves.

Referring to FIG. 25, a lateral cross-sectional atrial view of a heart 10 shows the mitral valve 17, aortic valve 510, tricuspid valve, 520 and pulmonary valve 530. As described above in reference to FIG. 8, the mitral valve 17 includes the anterior leaflet 20, the posterior leaflet 22 (including the medial scallop 24a, the middle scallop 24b, and the lateral scallop 24c), the left fibrous trigone 134a, and the right fibrous trigone 134b.

In regard to sealing between a prosthetic mitral valve and a native mitral valve, the differing anatomical features of various portions of the native mitral valve 17 make it advantageous to consider the mitral valve 17 as having three distinct sealing regions that together comprise the entirety of the mitral valve 17. The three distinct sealing regions are: an anterior region 25a, a posterior region 25b, and two commissural regions 25c. The anterior region 25a extends generally linearly between the left and right trigones 134a and 134b. The posterior region 25b comprises the middle scallop 24b and posterior portions of the lateral scallop 24a and medial scallop 24c. The commissural regions 25c extend between the anterior region 25a and the posterior region 25b. The commissural regions 25c generally encompass the commissures 30a and 30b, and anterior portions of the lateral scallop 24a and medial scallop 24c. These three sealing regions 25a, 25b, and 25c will be referenced again in regard to FIGS. 28-33.

Figure 26:
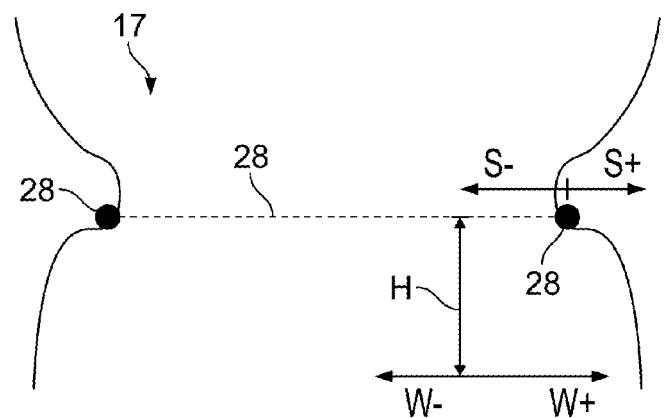
FIG. 26 is a schematic diagram of a cross-section of a native mitral valve including the mitral valve annulus.

Referring to FIG. 26, a schematic diagram of a cross-section of a native mitral 17 valve indicates the location of the mitral valve annulus 28. Three geometric variables (S, W, and H) that can be used to quantify a relative geometric orientation of sealing surfaces on the prosthetic valve in relation to the annulus 28 of the native mitral valve 17 are also indicated. As used herein, the term "sealing surfaces" is defined as surface areas on the prosthetic valve that are intended to make sealing contact with structures of the native mitral valve 17 (especially the leaflets of the native mitral valve 17). Hence, the sealing surfaces are the areas on the prosthetic valve that are used to facilitate the leaflet to valve body seal.

The geometric variable S quantifies the radial distance from the annulus 28 to the adjacent prosthetic valve framework surface. A negative S-value indicates that the annulus 28 and the adjacent prosthetic valve surface are spaced apart from each other. For example, an S-value of negative 2 mm indicates that there is a 2 mm space between the annulus 28 and the adjacent prosthetic valve surface. When S equals zero, it indicates that the annulus 28 and the adjacent prosthetic valve surface are in contact with each other in a line-to-line fit relationship. When S is a positive number, it indicates that the annulus 28 and the adjacent prosthetic valve surface are in an interference fit relationship. In other words, when S is a positive number some compressive force is being applied to the annulus 28 by the adjacent prosthetic valve surface.

The geometric variable H quantifies the distance from the superior limit (upper edge) to the inferior limit (lower edge) of the sealing surface on the prosthetic valve. H-values are measured downward (in reference to the illustration). For example, an H-value of 10 mm indicates that, for a particular sealing region, the sealing surface on the prosthetic valve ends 10 mm below the superior limit of the sealing surface. In another example, when the superior limit is at the annulus 28, an H-value of 7 mm indicates that the inferior limit of the sealing surface is 7 mm below the annulus 28. In general, the superior limit of the sealing surface on the prosthetic valve is either at, slightly above, or slightly below the annulus 28 (e.g., about 2 mm above or about 2 mm below the annulus 28 in some embodiments).

The geometric variable W quantifies the radial distance from the superior limit of the sealing surface to the inferior limit of the sealing surface on the prosthetic valve. A negative W-value indicates that the inferior limit of the sealing surface is positioned radially inward in comparison to the superior limit of the sealing surface (e.g., at least a portion of the sealing surface is flared or bowed inward at the distal end). A positive W-value indicates that the inferior limit of the sealing surface is positioned radially outward in comparison to superior limit of the sealing surface (e.g., at least a portion of the sealing surface is flared or bowed outward at the distal end). A W-value of zero indicates that the inferior limit of the sealing surface is positioned at the same radial position as the superior limit of the sealing surface.

Figure 27:
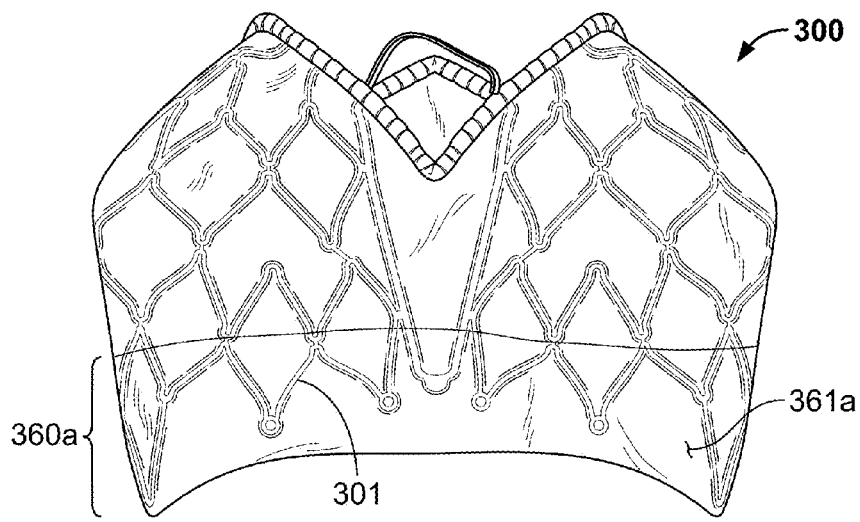
FIG. 27 is an anterior side view of a valve assembly, in accordance with some embodiments. A sealing region of the anterior side of the valve assembly is demarcated on the valve assembly.

Referring to FIG. 27, an anterior side view of a valve assembly 300 includes an anterior sealing surface 360a in accordance with some embodiments. In the depicted embodiment, the anterior sealing surface 360a spans the lower portion of the anterior side of valve assembly 300. The anterior sealing surface 360a comprises the surface area on the anterior side of the prosthetic valve assembly 300 that is intended to make sealing contact with structures of the native mitral valve. The anterior sealing surface 360a consists of structural support from the valve frame 301 as well as a tissue surface 361a. The anterior tissue surface 361a provides sealing interface height (H) but its flexible nature reduces the amount of LVOT obstruction, as will be described later. For example, at least a portion of the anterior sealing surface 360a is intended to make sealing contact with the anterior leaflet of the native mitral valve.

Figure 28:
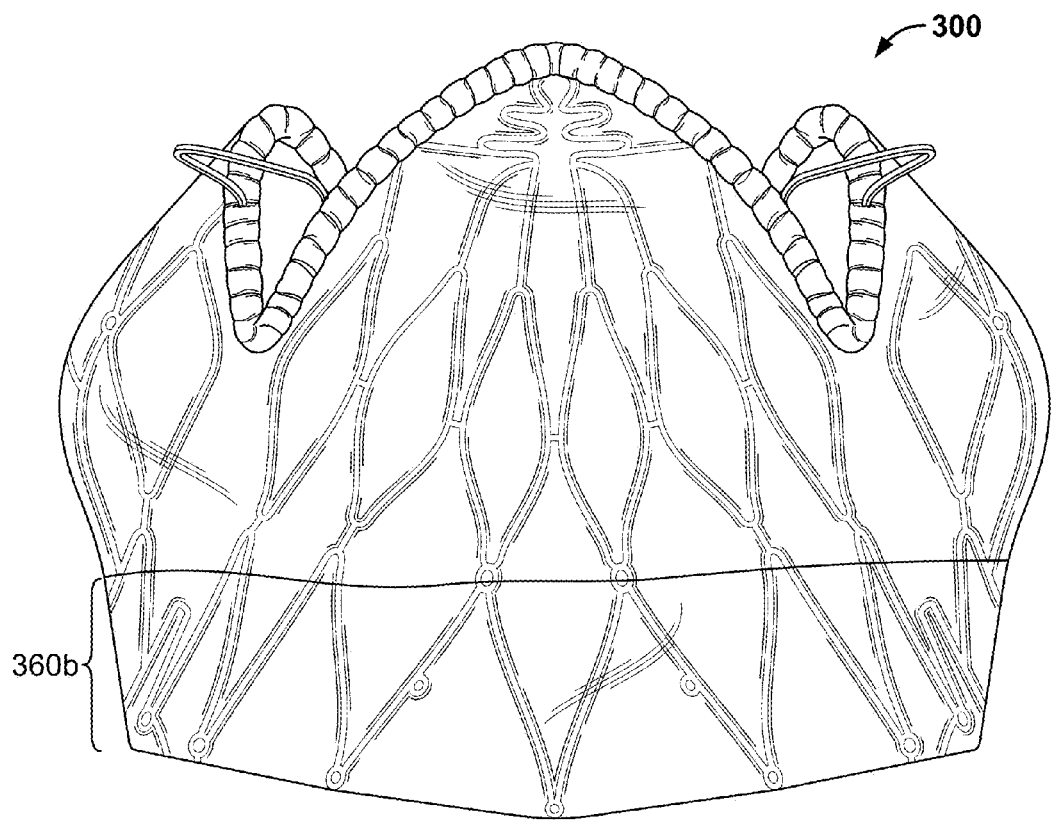
FIG. 28 is a posterior side view of a valve assembly, in accordance with some embodiments. A sealing region of the posterior side of the valve assembly is demarcated on the valve assembly.

Referring to FIG. 28, a posterior side view of a valve assembly 300 includes a posterior sealing surface 360b in accordance with some embodiments. In the depicted embodiment, the posterior sealing surface 360b spans the lower portion of the posterior side of valve assembly 300. The posterior sealing surface 360b comprises the surface area on the posterior side of the prosthetic valve assembly 300 that is intended to make sealing contact with structures of the native mitral valve. For example, at least a portion of the posterior sealing surface 360b is intended to make sealing contact with the posterior leaflet of the native mitral valve.

Figure 29:
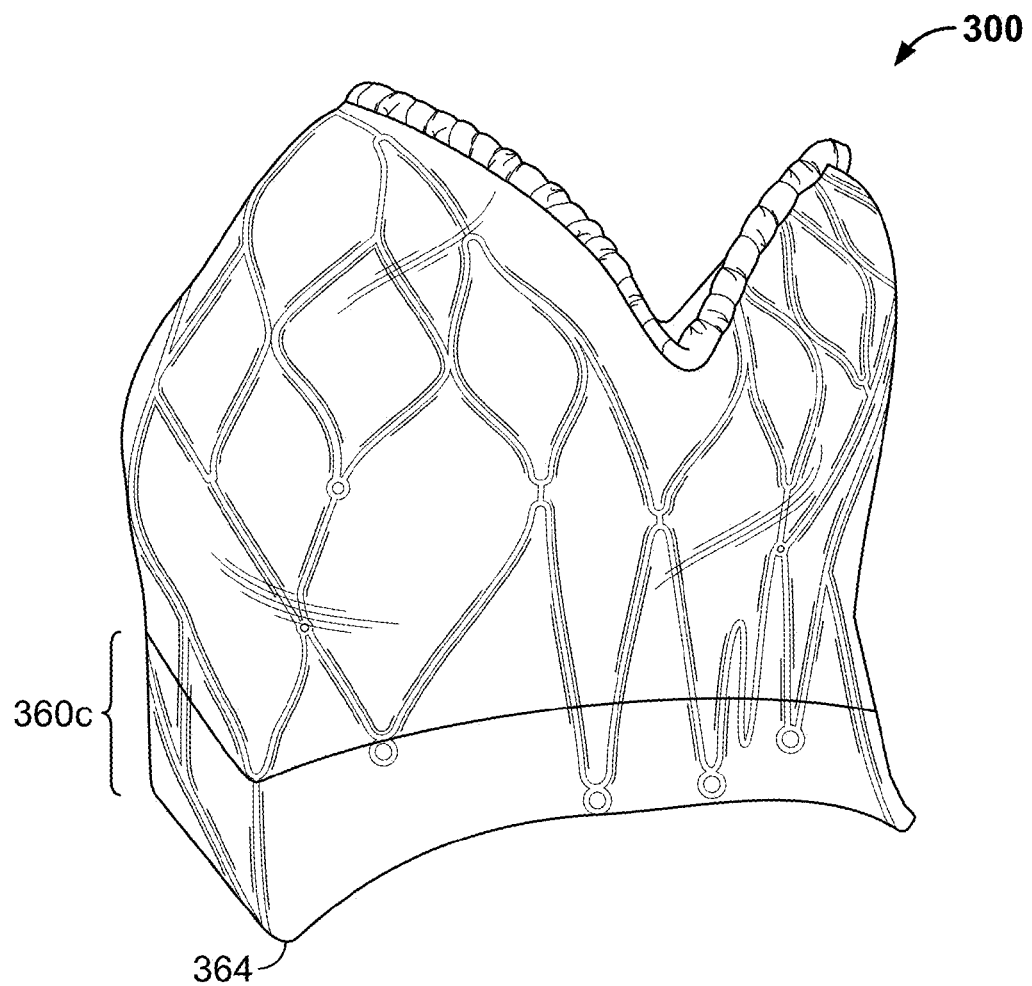
FIG. 29 is a lateral side view of a valve assembly, in accordance with some embodiments. A sealing region of the lateral side of the valve assembly is demarcated on the valve assembly.

Referring to FIG. 29, a commissural (lateral) side view of a valve assembly 300 includes a commissural sealing surface 360c in accordance with some embodiments. This view is slightly biased to the anterior side of the valve assembly 300. In the depicted embodiment, the commissural sealing surface 360c spans the lower portion of the commissural side of valve assembly 300. The commissural sealing surface 360c comprises the surface area on the lateral side of the prosthetic valve assembly 300 that is intended to make sealing contact with structures of the native mitral valve. For example, at least a portion of the commissural sealing surface 360c is intended to make sealing contact with the medial scallop or the lateral scallop of the posterior leaflet of the native mitral valve, and with the leaflet tissue in the commissural regions of the native mitral valve.

Figure 30:
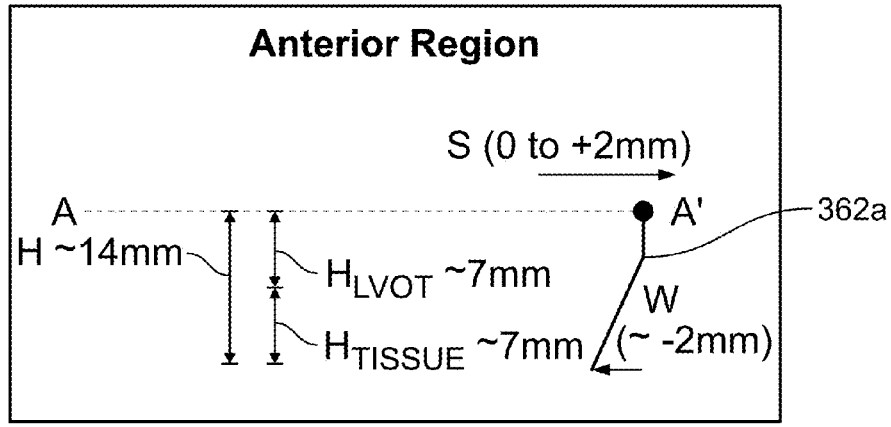
FIG. 30 is a schematic depiction of an anterior portion of a valve assembly in relationship to the annulus of the native mitral valve.

Referring to FIG. 30, the geometric relationship between a native mitral valve annulus and an anterior sealing surface of a prosthetic mitral valve in accordance with some embodiments can be represented by the S, H, and W values as described above in reference to FIG. 26. For example, in some embodiments the S-value of the anterior sealing surface of the prosthetic mitral valve is in a range from about zero millimeters to about positive 2 millimeters. In other words, the S-value of the anterior sealing surface in relation to the native mitral valve annulus is in a range from about line-to-line contact to about 2 millimeters interference. It should be understood that in this context an interference fit does not necessarily mean that the native valve annulus is stretched or deformed as a result of the interference. More likely, rather, the prosthetic valve assembly will be inhibited by the annulus from enlarging to its unconstrained fully expanded size. While in the depicted embodiment the S-value is in a range of about zero millimeters to about positive 2 millimeters, in some embodiments the S-value is in a range of about negative 2 millimeters to about positive 1 millimeter, or about negative 1 millimeter to about positive 3 millimeters, or about zero millimeters to about positive 4 millimeters. In some embodiments, the S-value can be more negative than about negative 2 millimeters or more positive than about positive 4 millimeters.

In some embodiments the H-value of the anterior sealing surface of the prosthetic mitral valve is about 14 millimeters. In other words, in some embodiments the distance from the superior edge of the anterior sealing surface to the inferior edge of the anterior sealing surface is about 14 millimeters. More specifically, the H-value of the anterior sealing surface can be divided into two portions: (1) a superior portion, $H_{LVOT}$ and (2) an inferior portion, $H_{TISSUE}$. The $H_{LVOT}$-value generally corresponds to the distance from the superior edge of the anterior sealing surface to the inferior end of the valve frame 301 at various places along the anterior sealing surface 360a (refer to FIG. 27). The $H_{TISSUE}$-value corresponds to the distance from the inferior end of the valve frame 301 at various places along the anterior sealing surface 360a to the inferior end of the anterior tissue surface 361a at those places. While in the depicted embodiment, the $H_{LVOT}$-value and the $H_{TISSUE}$-value are equal to each other, in some embodiments the ratio between the $H_{LVOT}$-value and the $H_{TISSUE}$-value is about 3:1, about 2:1, about 1.5:1, about 1:1.5, about 1:2, or about 3:1.

While in the depicted embodiment the total H-value is about 14 millimeters, in some embodiments the H-value is in a range of about 8 millimeters to about 10 millimeters, or about 10 millimeters to about 12 millimeters, or about 12 millimeters to about 14 millimeters, or about 14 millimeters to about 16 millimeters, or about 13 millimeters to about 15 millimeters. In some embodiments, the H-value can be less than about 8 millimeters or more than about 16 millimeters.

In some embodiments the W-value of the anterior sealing surface of the prosthetic mitral valve is about negative 2 millimeters. In other words, in some embodiments the radial distance from the superior edge of the anterior sealing surface to the inferior edge of the anterior sealing surface on the prosthetic valve is about negative 2 millimeters. A W-value of negative 2 millimeters indicates that the lower edge of the anterior sealing surface is positioned radially inward in comparison to the superior edge of the anterior sealing surface by about 2 millimeters. This also indicates that the sub-annular anterior valve assembly is flared or bowed inward, such as indicated by valve body profile line 362a. While in the depicted embodiment the W-value is about negative 2 millimeters, in some embodiments the W-value is in a range of about negative 6 millimeters to about negative 4 millimeters, or about negative 4 millimeters to about negative 2 millimeters, or about negative 2 millimeters to about zero millimeters, or about zero millimeters to about positive 2 millimeters, or about negative 3 millimeters to about negative 1 millimeter. In some embodiments, the W-value can be more negative than about negative 6 millimeters or more positive than about positive 2 millimeters.

Figure 31:
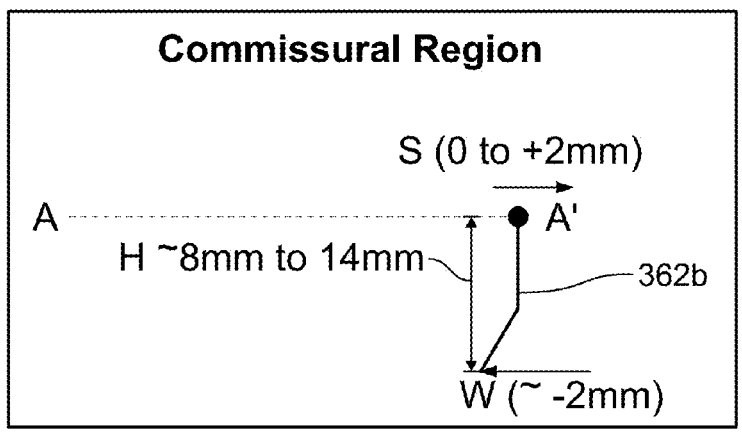
FIG. 31 is a schematic depiction of a commissural region portion of a valve assembly in relationship to the annulus of the native mitral valve.

Referring to FIG. 31, the geometric relationship between a native mitral valve annulus and a commissural sealing surface of a prosthetic mitral valve in accordance with some embodiments can be represented by the S, H, and W values as described above in reference to FIG. 26. For example, in some embodiments the S-value of the commissural sealing surface of the prosthetic mitral valve is in a range from about zero millimeters to about positive 2 millimeters. In other words, the S-value of the commissural sealing surface in relation to the native mitral valve annulus is in a range from about line-to-line contact to about 2 millimeters interference. It should be understood that in this context an interference fit does not necessarily mean that the native valve annulus is stretched or deformed as a result of the interference. More likely, rather, the prosthetic valve assembly will be inhibited by the annulus from enlarging to its fully expanded size. While in the depicted embodiment the S-value is in a range of about zero millimeters to about positive 2 millimeters, in some embodiments the S-value is in a range of about negative 2 millimeters to about positive 1 millimeter, or about negative 1 millimeter to about positive 3 millimeters, or about zero millimeters to about positive 4 millimeters. In some embodiments, the S-value can be more negative than about negative 2 millimeters or more positive than about positive 4 millimeters.

In some embodiments, the H-value of the commissural sealing surface of the prosthetic mitral valve is in a range of about 8 millimeters to about 14 millimeters. In other words, in some embodiments the distance from the native valve annulus to the lower (inferior) edge of the commissural sealing surface is in a range of about 8 millimeters to about 14 millimeters. This range, from about 8 millimeters to about 14 millimeters, is at least partly a result of the shape of a commissural corner 364 (refer to FIG. 29) that comprises part of the commissural sealing surface. Accordingly, the lower edge of the commissural sealing surface varies across the lateral width of the commissural sealing surface just by the nature of the shape of the commissural sealing surface. While in the depicted embodiment the H-value is in a range of about 8 millimeters to about 14 millimeters, in some embodiments the H-value is in a range of about 4 millimeters to about 10 millimeters, or about 6 millimeters to about 12 millimeters, or about 8 millimeters to about 14 millimeters, or about 10 millimeters to about 16 millimeters, or about 7 millimeters to about 15 millimeters. In some embodiments, the H-value can be less than about 4 millimeters or more than about 15 millimeters.

In some embodiments the W-value of the commissural sealing surface of the prosthetic mitral valve is about negative 2 millimeters. In other words, in some embodiments the radial distance from the superior (upper) edge of the commissural sealing surface to the inferior (lower) edge of the commissural sealing surface on the prosthetic valve is about negative 2 millimeters. A W-value of negative 2 millimeters indicates that the lower edge of the commissural sealing surface is positioned radially inward in comparison to the upper edge of the commissural sealing surface by about 2 millimeters. This also indicates that the sub-annular commissural valve assembly is flared or bowed inward, such as indicated by valve body profile line 362b. While in the depicted embodiment the W-value is about negative 2 millimeters, in some embodiments the W-value is in a range of about negative 6 millimeters to about negative 4 millimeters, or about negative 4 millimeters to about negative 2 millimeters, or about negative 2 millimeters to about zero millimeters, or about zero millimeters to about positive 2 millimeters, or about negative 3 millimeters to about negative 1 millimeter. In some embodiments, the W-value can be more negative than about negative 6 millimeters or more positive than about positive 2 millimeters.

Figure 32:
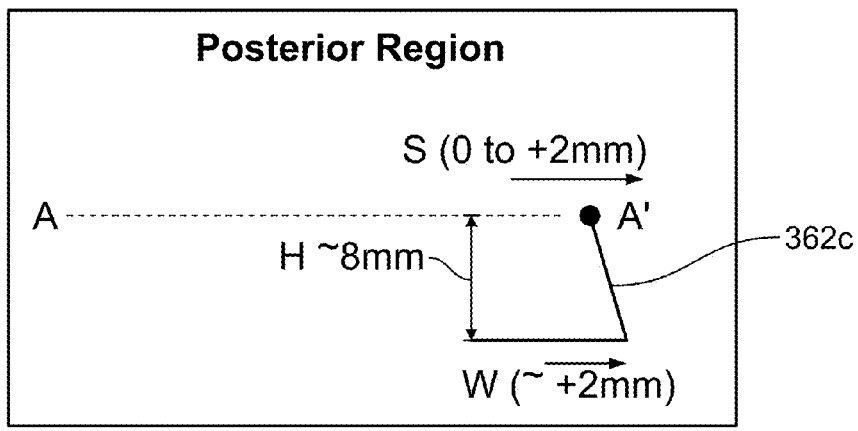
FIG. 32 is a schematic depiction of a posterior portion of a valve assembly in relationship to the annulus of the native mitral valve.

Referring to FIG. 32, the geometric relationship between a native mitral valve annulus and a posterior sealing surface of a prosthetic mitral valve in accordance with some embodiments can be represented by the S, H, and W values as described above in reference to FIG. 26. For example, in some embodiments the S-value of the posterior sealing surface of the prosthetic mitral valve is in a range from about zero millimeters to about positive 2 millimeters. In other words, the S-value of the posterior sealing surface in relation to the native mitral valve annulus is in a range from about line-to-line contact to about 2 millimeters interference. It should be understood that in this context an interference fit does not necessarily mean that the native valve annulus is stretched or deformed as a result of the interference. More likely, rather, the prosthetic valve assembly will be inhibited by the annulus from enlarging to its fully expanded size. While in the depicted embodiment the S-value is in a range of about zero millimeters to about positive 2 millimeters, in some embodiments the S-value is in a range of about negative 2 millimeters to about positive 1 millimeter, or about negative 1 millimeter to about positive 3 millimeters, or about zero millimeters to about positive 4 millimeters. In some embodiments, the S-value can be more negative than about negative 2 millimeters or more positive than about positive 4 millimeters.

In some embodiments, the H-value of the posterior sealing surface of the prosthetic mitral valve is about 8 millimeters. In other words, in some embodiments the distance from the native valve annulus to the lower (inferior) edge of the posterior sealing surface is about 8 millimeters. While in the depicted embodiment the H-value is about 8 millimeters, in some embodiments the H-value is in a range of about 4 millimeters to about 6 millimeters, or about 6 millimeters to about 8 millimeters, or about 8 millimeters to about 10 millimeters, or about 10 millimeters to about 12 millimeters, or about 7 millimeters to about 9 millimeters. In some embodiments, the H-value can be less than about 4 millimeters or more than about 12 millimeters.

In some embodiments, the W-value of the posterior sealing surface of the prosthetic mitral valve is about positive 2 millimeters. In other words, in some embodiments the radial distance from the upper (superior) edge of the posterior sealing surface to the lower (inferior) edge of the posterior sealing surface on the prosthetic valve is about positive 2 millimeters. A W-value of positive 2 millimeters indicates that the lower edge of the posterior sealing surface is positioned radially outward in comparison to the upper edge of the posterior sealing surface by about 2 millimeters. This also indicates that the sub-annular posterior valve assembly is flared or bowed outward, such as indicated by valve body profile line 362c. While in the depicted embodiment the W-value is about positive 2 millimeters, in some embodiments the W-value is in a range of about negative 4 millimeters to about negative 2 millimeters, or about negative 2 millimeters to about zero millimeters, or about zero millimeters to about positive 2 millimeters, or about positive 2 millimeters to about positive 4 millimeters, or about positive 1 millimeter to about positive 3 millimeters. In some embodiments, the W-value can be more negative than about negative 2 millimeters or more positive than about positive 3 millimeters.

Figure 33:
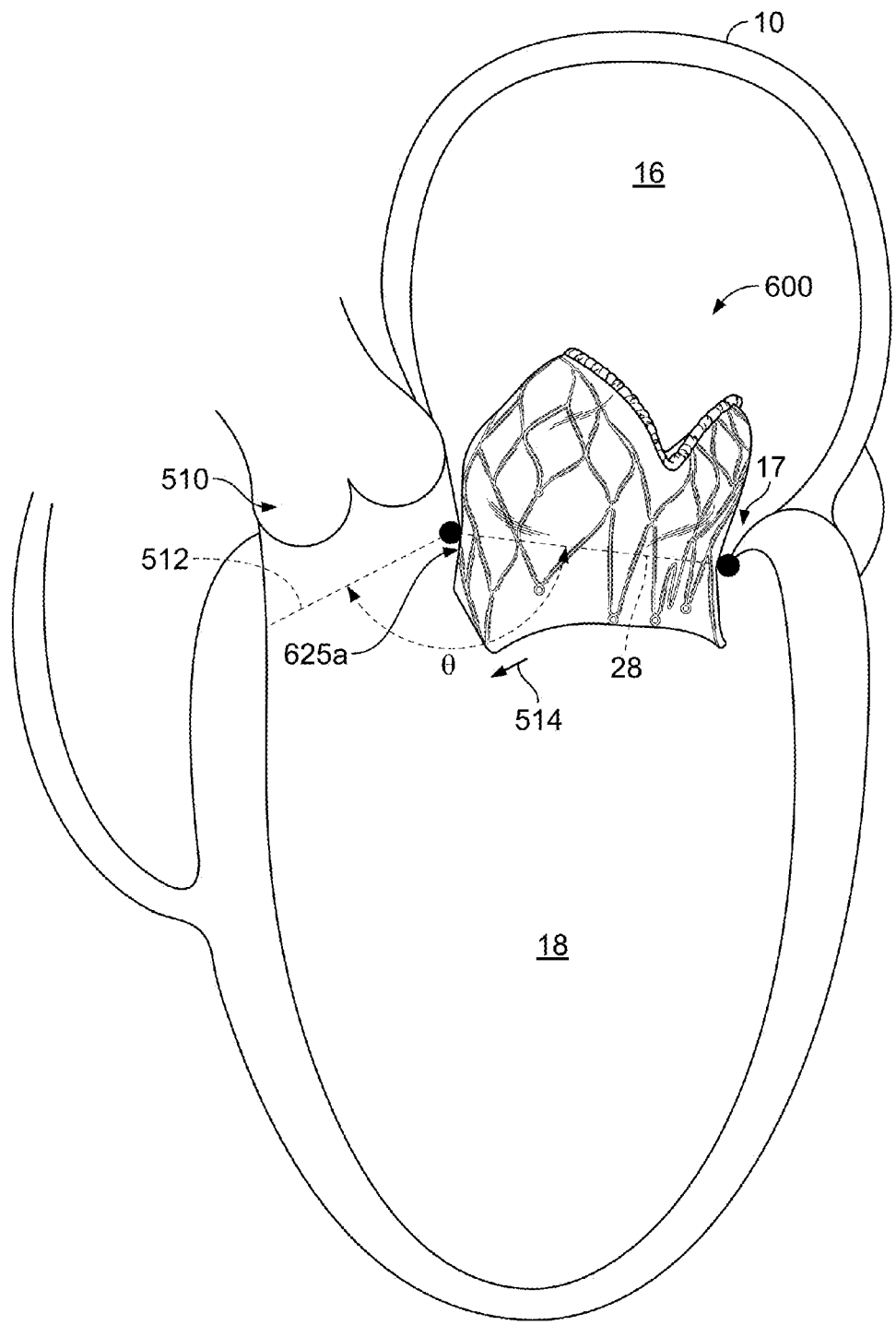
FIG. 33 is a cross-sectional view of the left side of a heart showing an example valve assembly in relationship to the annulus of the native mitral valve and the annulus of the aortic root.

Referring to FIG. 33, during systole the aortic valve 510 receives blood flowing out from the left ventricle 18. The blood flows to the aortic valve 510 via a left ventricular outflow tract (LVOT) 512. In some circumstances, a prosthetic mitral valve 600 (shown without an anchor assembly for simplicity) implanted in the native mitral valve 17 may obstruct the LVOT 512, as represented by an obstruction 514, resulting in reduced ejection of blood from the left ventricle 18. As described herein, the prosthetic mitral valves provided by this disclosure may be configured to reduce or eliminate LVOT obstructions 514.

Figure 34:
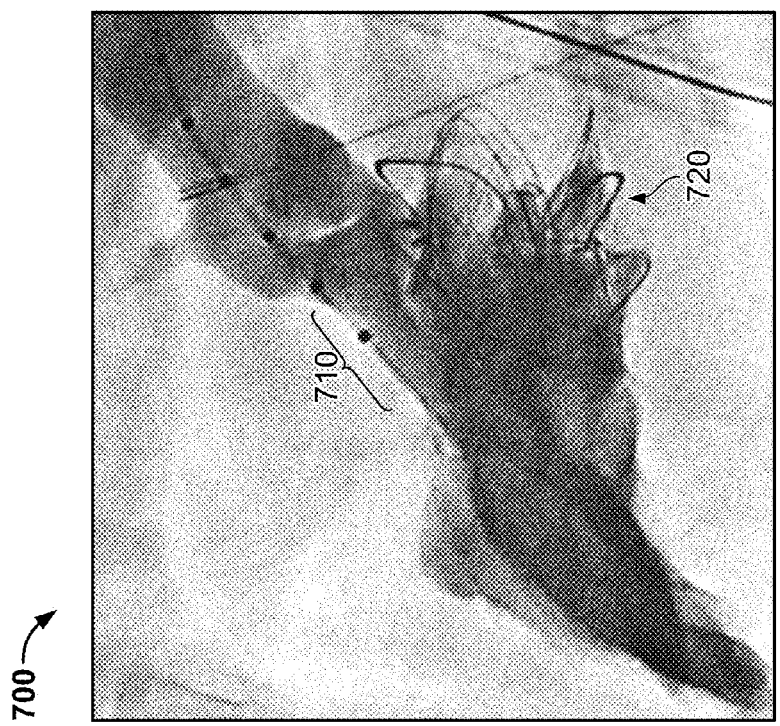
FIG. 34 is a fluoroscopic image of a native mitral valve with an example prosthetic valve therein, an aortic valve, and a left ventricular outflow track of a heart. The image also shows blood flowing from the left ventricle to the aorta through the left ventricular outflow track.
Figure 35:
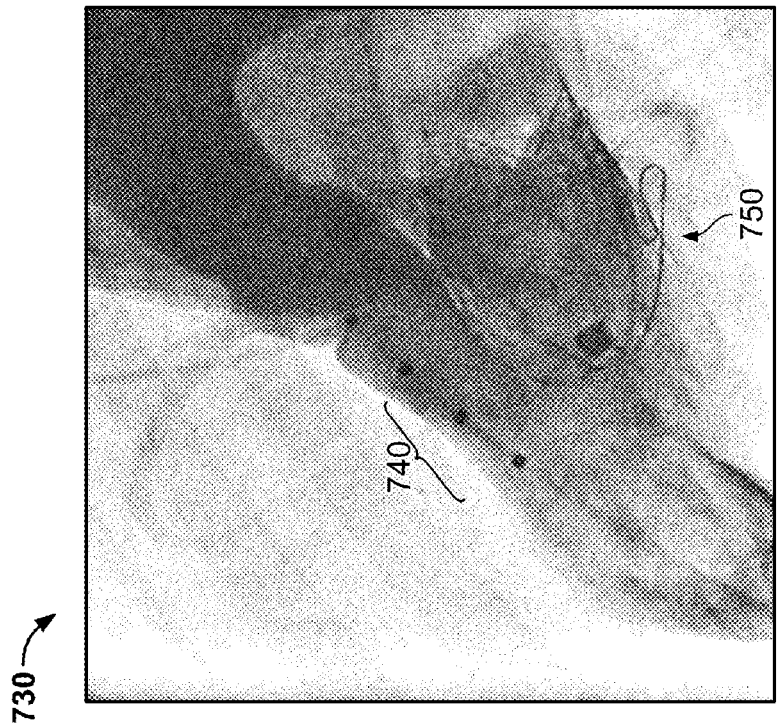
FIG. 35 is another fluoroscopic image of a native mitral valve with an example prosthetic valve therein, an aortic valve, and a left ventricular outflow track of a heart. The image also shows blood flowing from the left ventricle to the aorta through the left ventricular outflow track.

Referring to FIGS. 34 and 35, a first fluoroscopic image 700 and a second fluoroscopic image 730 were obtained after fluoroscopic dye was injected into the left ventricle to enhance visualization of blood flow and blood flow obstructions. The images show blood flowing from the left ventricle to the aorta through the left ventricular outflow track (LVOT).

The first fluoroscopic image 700 illustrates an area of reduced blood flow 710 caused by an LVOT obstruction from a prosthetic mitral valve 720. The second fluoroscopic image 730 illustrates improved blood flow 740 through the LVOT. The improved blood flow 740 can be a result of less obstruction attributable to the prosthetic mitral valve 750. For example, in some embodiments the prosthetic mitral valve 750 can be positioned or designed so that less structure of the valve 750 is below the native mitral valve annulus, resulting in less structure of the valve 750 within the LVOT. Additionally, the prosthetic mitral valve 750 can be positioned or designed so that less structure of the valve 750 is within the LVOT such as by tapering, bowing, or shaping the structure away from the LVOT.

Referring again to FIG. 33, the portion of the prosthetic mitral valve 600 that faces the aortic valve 510 is the anterior sealing surface 625a. Therefore, the geometric orientation of the anterior sealing surface 625a in relation to the LVOT 512 is a factor relating to whether or not the prosthetic mitral valve 600 will cause obstructions 514.

Figure 36:
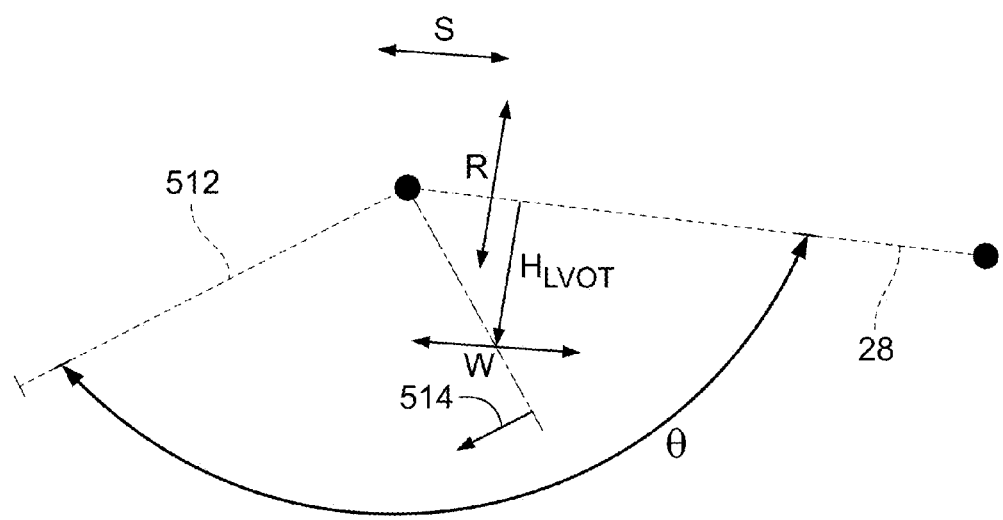
FIG. 36 is a schematic depiction of the annulus of the native mitral valve and the annulus of the aortic root.

Referring also to FIG. 36, the geometric relationships between the LVOT 512, the native mitral valve annulus 28, and the anterior sealing surface variables (S-value, H-value, and W-value, as described in reference to FIGS. 25, 26, and 30) can be used to quantify LVOT obstructions 514. The angle between the LVOT 512 and the native mitral valve annulus 28 is identified as θ. The R-value is a variable that accounts for prosthetic valve positioning variations from the anticipated/ideal location of the prosthetic valve relative to the native valve annulus.

Using geometry, the LVOT obstruction 514 distance (identified as "O" in the equation below) can be calculated using the following equation:

$$O = R\sin\theta + \sqrt{W^2 + H_{LVOT}^2} \sin\left\{\theta - \tan^{-1}\left(\frac{W}{H}\right)\right\} - S\cos\theta \quad \text{Equation \#1}$$

where:
O is the calculated distance of an LVOT obstruction;

R is the distance from the native valve annulus to the top of the anterior sealing surface;

θ is the angle between the mitral valve annulus and the LVOT;

W is the radial distance from the upper edge of the sealing surface to the lower edge of the sealing surface on the prosthetic valve;

$H_{LVOT}$ is the distance from the superior edge of the sealing surface to the lower structural (frame) edge of the sealing surface on the prosthetic valve: and S is the radial distance from the mitral valve annulus to the adjacent prosthetic valve surface.

The following examples are provided to illustrate Equation #1 above.

| Example | R (mm) | S (mm) | $H_{LVOT}$ (mm) | W (mm) | θ° | O (mm) |
|---|---|---|---|---|---|---|
| 1 | 0 | 2 | 8 | −2 | 164 | 2.2 |
| 2 | 0 | 0 | 8 | −2 | 119 | 6.0 |
| 3 | 0 | 2 | 8 | −4 | 119 | 6.0 |
| 4 | 0 | 2 | 5 | −4 | 119 | 3.4 |
| 5 | 0 | 0 | 14 | −2 | 164 | 1.9 |

By comparing Examples #1 and #5, with Examples #2, #3, and #4 it can be ascertained that O (the LVOT obstruction) tends to be less when θ is greater. By comparing Example #3 and Example #4, it is seen that a greater $H_{LVOT}$ tends to result in a higher O. By comparing Example #2 and Example #3, it can be determined that the effect of a greater S-value can be offset by a more negative W-value. In summary, one of ordinary skill in the art can use these teachings to select an R-value, S-value, $H_{LVOT}$-value, and W-value for a given θ (based on patient anatomy) in effort to attain an acceptable O (the LVOT obstruction).

Referring to FIGS. 37 and 38, an anchor assembly 200 can be engaged with a native mitral valve 17 such that the feet 220a, 220b, 220c, and 220d are seated in the sub-annular gutter 19 of the native mitral valve 17, while the leaflets 20 and 22 and chordae tendineae 40 are substantially unhindered by the anchor assembly 200. As described above, the anchor assembly 200 is designed to be implanted within a native mitral valve 17, without substantially interfering with the native valve 17, so that the native valve 17 can continue to function as it did prior to the placement of the anchor assembly 200. To accomplish that, the leaflets 20 and 22 and chordae tendineae 40, especially the chordae tendineae 40 that are attached to the anterior leaflet 20, need to be substantially unhindered by the anchor assembly 200.

In some implementations, the positioning of the hub 210 relative to the anatomical features of the mitral valve 17 is relevant to facilitating substantially unhindered leaflets 20 and 22 and chordae tendineae 40. For example, a depth 810 of the hub 210 in the left ventricle 18 is one relevant consideration. In order to substantially prevent hindrances to the leaflets 20 and 22 and chordae tendineae 40, the depth 810 should be at least slightly below the coaptation depth of the mitral valve 17. The coaptation depth is the greatest vertical distance from the annulus of the mitral valve 17 to an area of coaptation between the native leaflets 20 and 22. Hence, positioning the hub 210 below the coaptation depth will facilitate substantially unhindered leaflets 20 and 22 and chordae tendineae 40. In some implementations, the depth 810 is in a range of about 14 mm to about 20 mm, or about 10 mm to about 16 mm, or about 12 mm to about 18 mm, or about 16 mm to about 22 mm. In some implementations, the depth 810 is less than about 10 mm or greater than about 22 mm.

The positioning of the hub 210 relative to the line of coaptation between the leaflets 20 and 22 (e.g., the line of coaptation 32 shown in FIG. 8) is also relevant to facilitating substantially unhindered leaflets 20 and 22 and chordae tendineae 40. For example, in some implementations positioning the hub 210 generally in vertical alignment with the line of coaptation will serve to substantially prevent hindrances to the leaflets 20 and 22 and the chordae tendineae 40.

In some implementations, the angular positioning of the left anterior sub-annular support arm 230a, the left posterior sub-annular support arm 230b, the right posterior sub-annular support arm 230c, and the right anterior sub-annular support arm 230d in relation to the native mitral valve 17 is relevant to facilitating substantially unhindered leaflets 20 and 22 and chordae tendineae 40. In some implementations, the sub-annular support arms 230a, 230b, 230c, and 230d are arranged symmetrically in relation to a left ventricular long axis (LAX) 840. That is, the LAX 840 bisects an anterior support arm angle 830 and a posterior support arm angle 820.

To minimize disturbances to the anterior leaflet 20 and chordae tendineae 40, the anterior support arms 220a and 220d are positioned essentially between the chordae tendineae 40. In some embodiments, the anterior support arm angle 830 is in a range of about 100° to about 135°, or about 80° to about 120°, or about 120° to about 160°. To minimize disturbances to the posterior leaflet 22 and chordae tendineae 40, in some implementations the posterior support arms 220b and 220b may extend essentially amongst the chordae tendineae 40. In some embodiments, the posterior support arm angle 820 is in a range of about 50° to about 120°, or about 40° to about 80°, or about 60° to about 100°, or about 80° to about 120°, or about 100° to about 140°.

A number of embodiments of the invention have been described. Nevertheless, it will be understood that various modifications may be made without departing from the scope of the invention. Accordingly, other embodiments are within the scope of the following claims.

What is claimed is:

1. A mitral valve replacement system for a heart, comprising:
   an expandable anchor assembly configured to implant at a native mitral valve, the expandable anchor assembly including a first expandable frame that is adjustable from a delivery condition to an expanded condition;
   a first delivery sheath device having a distal end insertable into a left atrium and being configured to express the anchor assembly out from the distal end such that the anchor assembly expands within the left atrium to the expanded condition;
   a pusher instrument releasably attachable to the first expandable frame and being configured to longitudinally advance the anchor assembly within the left atrium towards an annulus of the native mitral valve while the anchor assembly is in the expanded condition; and
   an artificial valve assembly comprising a second expandable frame that is slidably engaged with an exterior of the pusher instrument and adjustable from a compressed condition to a deployed condition to selectively engage with the anchor assembly while the anchor assembly is in the expanded condition.

2. The system of claim 1, wherein the anchor assembly comprises a plurality of sub-annular projections configured to engage tissue proximate to the annulus of the native mitral valve while preserving natural function of anterior and posterior leaflets of the native mitral valve.

3. The system of claim 1, further comprising a second delivery sheath device having a distal end insertable into a left atrium and being configured to express the artificial valve assembly out from the distal end such that the artificial valve assembly at least expands within the left atrium.

4. The system of claim 1, wherein the artificial valve assembly comprises a guide structure to slidably engage with an exterior of the pusher instrument while the pusher instrument is releasably attached to the first expandable frame.

5. The system of claim 1, wherein the second expandable frame of the artificial valve assembly is separately expandable from the anchor assembly and further comprises: a generally D-shaped outer peripheral region, and a circular valve orifice located radially inward from the generally D-shaped outer peripheral region and carrying valve leaflets that define a circular perimeter at the circular valve orifice.

6. The system of claim 1, wherein the artificial valve assembly is releasably coupled to a control catheter that defines a lumen, and wherein the artificial valve assembly is slidably engaged with an exterior of the pusher instrument by slidably disposing the pusher instrument within the lumen of the control catheter.

7. The system of claim 1, further comprising a guidewire slidably disposable within the pusher instrument.

8. A mitral valve replacement system for a heart, comprising:
an expandable anchor assembly configured to implant at a native mitral valve, the expandable anchor assembly including a first expandable frame that is adjustable from a delivery condition to an expanded condition;
a first delivery sheath device having a distal end insertable into a left atrium and being configured to express the anchor assembly out from the distal end such that the anchor assembly expands within the left atrium to the expanded condition;
a pusher instrument releasably attachable to the first expandable frame and being configured to longitudinally advance the anchor assembly within the left atrium towards an annulus of the native mitral valve while the anchor assembly is in the expanded condition;
an anchor assembly control wire slidably disposable within the first delivery sheath device, wherein the anchor assembly control wire is coupled with the anchor assembly; and
an artificial valve assembly comprising a second expandable frame that is adjustable from a compressed condition to a deployed condition to selectively engage with the anchor assembly while the anchor assembly is in the expanded condition.

9. A mitral valve replacement system for a heart, comprising:
an expandable anchor assembly configured to implant at a native mitral valve, the expandable anchor assembly including a first expandable frame that is adjustable from a delivery condition to an expanded condition;
a first delivery sheath device having a distal end insertable into a left atrium and being configured to express the anchor assembly out from the distal end such that the anchor assembly expands within the left atrium to the expanded condition;
a pusher instrument releasably attachable to the first expandable frame and being configured to longitudinally advance the anchor assembly within the left atrium towards an annulus of the native mitral valve while the anchor assembly is in the expanded condition;
a secondary deflectable catheter slidably disposed between the first delivery sheath device and the pusher instrument; and
an artificial valve assembly comprising a second expandable frame that is adjustable from a compressed condition to a deployed condition to selectively engage with the anchor assembly while the anchor assembly is in the expanded condition.

10. The system of claim 9, wherein a distal end portion of the secondary deflectable catheter is controllably laterally deflectable.

11. An implantable medical device delivery system comprising:
a first deflectable catheter defining a first lumen therethrough, wherein a distal end portion of the first deflectable catheter is controllably laterally deflectable;
a first device delivery sheath slidably disposable within the first lumen, the first device delivery sheath defining a second lumen therethrough;
a first device control sheath slidably disposable within the second lumen, the first device control sheath defining a third lumen therethrough and one or more first device control wire lumens;
a second deflectable catheter slidably disposable within the third lumen, the second deflectable catheter defining a fourth lumen therethrough, wherein a distal end portion of the second deflectable catheter is controllably laterally deflectable; and
a device pusher catheter slidably disposable within the fourth lumen, the device pusher catheter defining a fifth lumen therethrough, a distal end portion of the device pusher catheter configured to releasably couple with a first implantable medical device.

12. The delivery system of claim 11, further comprising a guidewire slidably disposable within the fourth lumen.

13. The delivery system of claim 11, further comprising a second device delivery sheath slidably disposable within the first lumen, the second device delivery sheath defining a sixth lumen therethrough.

14. The delivery system of claim 13, further comprising a second device control sheath slidably disposable within the sixth lumen, the second device control sheath defining a seventh lumen therethrough and one or more second device control wire lumens, the distal pusher catheter being slidably disposable within the seventh lumen.

15. The delivery system of claim 14, further comprising a first device control wire slidably disposable within the one or more first device control wire lumens and a second device control wire slidably disposable within the one or more second device control wire lumens.

* * * * *